US008431361B2

(12) United States Patent
Ballard et al.

(10) Patent No.: US 8,431,361 B2
(45) Date of Patent: Apr. 30, 2013

(54) BACTERIAL CELLS, OPTIMIZED NUCLEOTIDE SEQUENCES AND METHODS FOR IMPROVED EXPRESSION OF RECOMBINANT *CLOSTRIDIUM DIFFICILE* TOXIN B

(75) Inventors: Jimmy D. Ballard, Norman, OK (US); Elaine E. Hamm, Oklahoma City, OK (US); Jordi M. Melton, Norman, OK (US)

(73) Assignee: Board of Regents of The University of Oklahoma, Norman, OK (US)

( * ) Notice: Subject to any disclaimer, the term of this patent is extended or adjusted under 35 U.S.C. 154(b) by 237 days.

(21) Appl. No.: 12/885,356

(22) Filed: Sep. 17, 2010

(65) Prior Publication Data

US 2012/0070859 A1 Mar. 22, 2012

(51) Int. Cl.
*C12P 21/06* (2006.01)
*C12N 1/20* (2006.01)
*C07H 21/02* (2006.01)
*C07K 14/00* (2006.01)

(52) U.S. Cl.
USPC ....... 435/69.1; 435/252.3; 536/23.1; 530/350

(58) Field of Classification Search ................. 435/69.1, 435/252.3; 536/23.1; 530/350
See application file for complete search history.

(56) References Cited

U.S. PATENT DOCUMENTS

2007/0231336 A1 10/2007 Thomas et al.
2007/0269861 A1 11/2007 Williams et al.
2009/0087478 A1 4/2009 Hansen et al.
2010/0278868 A1* 11/2010 Gardiner et al. ........... 424/239.1

FOREIGN PATENT DOCUMENTS

WO 2007/146139 * 12/2007
WO WO-2010094970 A1 8/2010

OTHER PUBLICATIONS

Bioclone Inc. 2012; www.bioclone.us/toxin-69-Recombinant-cDNA-C9XKU6-Clostridium-difficile-toxin-B.*
Wang E., GenScript Upgrades OptimumGene Gene Design System, Nov. 3, 2008.

* cited by examiner

*Primary Examiner* — Karen Cochrane Carlson
(74) *Attorney, Agent, or Firm* — Winstead PC

(57) ABSTRACT

In some embodiments, the present invention provides isolated nucleotide sequences that encode *Clostridium difficile* toxin B, wherein the isolated nucleotide sequences have been optimized for improved expression of the toxin B in a bacterial cell. Other embodiments of the present invention pertain to methods of expressing recombinant *Clostridium difficile* toxin B in a bacterial cell from the isolated nucleotide sequences of the present invention. In other embodiments, the present invention pertains to bacterial cells that comprise the isolated nucleotide sequences of the present invention. In further embodiments, the invention pertains to isolated peptides of recombinant *Clostridium difficile* toxin B that were derived from the isolated nucleotide sequences of the present invention.

23 Claims, 16 Drawing Sheets

| | | | |
|---|---|---|---|
| TTT 22.1( 80995) | TCT 10.4( 38027) | TAT 17.5( 63937) | TGT 5.2( 19138) |
| TTC 16.0( 58774) | TCC 9.1( 33430) | TAC 12.2( 44631) | TGC 6.1( 22188) |
| TTA 14.3( 52382) | TCA 8.9( 32715) | TAA 2.0( 7356) | TGA 1.0( 3623) |
| TTG 13.0( 47500) | TCG 8.5( 31146) | TAG 0.3( 989) | TGG 13.9( 50991) |
| CTT 11.9( 43449) | CCT 7.5( 27340) | CAT 12.5( 45879) | CGT 20.0( 73197) |
| CTC 10.2( 37347) | CCC 5.4( 19666) | CAC 9.3( 34078) | CGC 19.7( 72212) |
| CTA 4.2( 15409) | CCA 8.6( 31534) | CAA 14.6( 53394) | CGA 3.8( 13844) |
| CTG 48.4(177210) | CCG 20.9( 76644) | CAG 28.4(104171) | CGG 5.9( 21552) |
| ATT 29.8(109072) | ACT 10.3( 37842) | AAT 20.6( 75436) | AGT 9.9( 36097) |
| ATC 23.7( 86796) | ACC 22.0( 80547) | AAC 21.4( 78443) | AGC 15.2( 55551) |
| ATA 6.8( 24984) | ACA 9.3( 33910) | AAA 35.3(129137) | AGA 3.6( 13152) |
| ATG 26.4( 96695) | ACG 13.7( 50269) | AAG 12.4( 45459) | AGG 2.1( 7607) |
| GTT 19.8( 72584) | GCT 17.1( 62479) | GAT 32.7(119939) | GGT 25.5( 93325) |
| GTC 14.3( 52439) | GCC 24.2( 88721) | GAC 19.2( 70394) | GGC 27.1( 99390) |
| GTA 11.6( 42420) | GCA 21.2( 77547) | GAA 39.1(143353) | GGA 9.5( 34799) |
| GTG 24.4( 89265) | GCG 30.1(110308) | GAG 18.7( 68609) | GGG 11.3( 41277) |

FIG. 1

```
Optimized   ATGAGCCTGGTGAACCGTAAACAGCTGGAAAAAATGGCGAATGTGCGTTTTCGCGTTCAG
Original    ATGAGTTTAGTTAATAGAAAACAGTTAGAAAAAATGGCAAATGTAAGATTTCGTGTTCAG

Optimized   GAAGATGAATACGTTGCGATTCTGGATGCCCTGGAAGAATATCATAACATGAGCGAAAAT
Original    GAAGATGAATATGTAGCAATATTGGATGCTTTAGAAGAATATCATAATATGTCAGAGAAT

Optimized   ACCGTGGTTGAAAAATACCTGAAACTGAAAGATATCAACAGTCTGACCGATATCTACATC
Original    ACTGTAGTCGAAAAATATTTAAAATTAAAAGATATAAATAGTTTAACAGATATTTATATA

Optimized   GATACGTACAAAAAATCTGGCCGCAACAAAGCCCTGAAAAAATTCAAAGAATACCTGGTG
Original    GATACATATAAAAAGTCTGGTAGAAATAAAGCCTTAAAAAAATTTAAGGAATACCTAGTT

Optimized   ACCGAAGTTCTGGAACTGAAAAACAATAACCTGACGCCGGTGGAGAAAAACCTGCACTTT
Original    ACAGAAGTATTAGAGCTAAAGAATAATAATTTAACTCCAGTTGAGAAAAATTTACATTTT

Optimized   GTTTGGATCGGCGGTCAGATCAACGATACCGCAATCAATTACATCAACCAGTGGAAAGAT
Original    GTTTGGATTGGAGGTCAAATAAATGACACTGCTATTAATTATATAAATCAATGGAAAGAT

Optimized   GTGAACTCTGATTACAACGTGAACGTGTTTTATGATAGTAATGCGTTCCTGATTAACACC
Original    GTAAATAGTGATTATAATGTTAATGTTTTTTATGATAGTAATGCATTTTTGATAAACACA

Optimized   CTGAAGAAAACCATCGTTGAAAGCGCCACGAACGATACCCTGGAATCTTTCCGTGAAAAC
Original    TTGAAAAAAACTATAGTAGAATCAGCAACAAATGATACACTTGAATCATTTAGAGAAAAC

Optimized   CTGAATGATCCGCGCTTCGATTACAACAAATTCTACCGTAAACGCATGGAAATCATCTAC
Original    TTAAATGACCCTAGATTTGACTATAATAAATTTTACAGAAAACGTATGGAGATAATCTAT

Optimized   GATAAACAGAAAAACTTCATCAACTACTACAAAACCCAGCGTGAAGAAAACCCGGATCTG
Original    GATAAGCAGAAAAATTTCATAAATTACTATAAAACTCAAAGAGAAGAAAATCCTGACCTT

Optimized   ATCATCGATGATATCGTGAAAATCTACCTGAGTAACGAATACAGCAAAGATATCGATGAA
Original    ATAATTGATGATATTGTAAAGATATATCTTTCAAACGAGTATTCAAAGGATATAGATGAA

Optimized   CTGAACAGCTATATCGAAGAATCTCTGAATAAAGTGACCGAAAACTCTGGCAATGATGTT
Original    CTTAATTCCTATATTGAAGAGTCATTAAATAAAGTTACAGAAAATAGTGGAAATGATGTT

Optimized   CGCAACTTTGAAGAATTCAAAGGCGGTGAAAGTTTTAAACTGTACGAACAGGAACTGGTG
Original    AGAAACTTTGAAGAATTTAAAGGTGGAGAGTCATTCAAATTATATGAACAAGAGTTGGTA

Optimized   GAACGTTGGAATCTGGCGGCCGCAAGTGATATCCTGCGCATTAGCGCGCTGAAAGAAGTG
Original    GAAAGATGGAATTTGGCAGCTGCTTCTGACATATTAAGAATATCTGCCTTAAAAGAAGTT

Optimized   GGCGGTGTTTATCTGGATGTTGATATGCTGCCGGGTATTCAGCCGGATCTGTTCGAAAGC
Original    GGTGGTGTATATTTAGATGTTGATATGTTACCAGGAATACAACCAGACCTATTTGAGTCT

Optimized   ATCGAAAAACCGAGCTCTGTGACCGTTGATTTTTGGGAAATGGTGAAACTGGAAGCAATC
Original    ATAGAGAAACCTAGTTCAGTAACAGTGGATTTTTGGGAAATGGTAAAATTAGAAGCTATA

Optimized   ATGAAATACAAAGAATACATCCCGGGCTATACGAGCGAACACTTCGATATGCTGGATGAA
Original    ATGAAATACAAAGAATACATACCAGGATATACTTCAGAGCATTTTGATATGTTGGATGAA
```

FIG. 2

```
Optimized   GAAGTGCAGAGTAGCTTTGAATCTGTTCTGGCGAGTAAAAGCGATAAAAGTGAAATTTTC
Original    GAAGTTCAAAGTAGTTTTGAATCTGTTCTAGCTTCTAAGTCAGATAAGTCAGAAATATTC

Optimized   TCTAGTCTGGGTGATATGGAAGCGAGCCCGCTGGAAGTTAAAATCGCCTTCAACTCTAAA
Original    TCATCACTTGGCGATATGGAGGCATCACCACTAGAAGTTAAAATTGCATTTAATAGTAAA

Optimized   GGCATCATCAACCAGGGTCTGATCAGTGTGAAAGATTCTTACTGCAGTAACCTGATCGTT
Original    GGTATTATAAATCAAGGACTAATTTCTGTGAAAGACTCATATTGTAGCAATTTAATAGTA

Optimized   AAACAGATCGAAAACCGTTACAAAATCCTGAATAACTCTCTGAACCCGGCCATTAGTGAA
Original    AAACAAATCGAGAACAGATATAAGATATTGAATAATAGTTTAAATCCAGCTATTAGCGAG

Optimized   GATAACGATTTTAATACCACGACCAATGCATTCATCGATAGCATTATGGCCGAAGCAAAC
Original    GATAACGATTTCAATACTACAACGAATGCTTTTATTGATAGTATAATGGCTGAAGCTAAT

Optimized   GCGGATAATGGCCGTTTTATGATGGAACTGGGTAAATATCTGCGCGTGGGCTTTTTCCCG
Original    GCAGATAATGGTAGATTTATGATGGAACTAGGAAAGTATTTAAGAGTTGGTTTCTTCCCA

Optimized   GATGTTAAAACGACCATTAACCTGAGCGGTCCGGAAGCGTACGCGGCAGCATATCAGGAT
Original    GATGTTAAAACTACTATTAACTTAAGTGGCCCTGAAGCATATGCGGCAGCTTATCAAGAT

Optimized   CTGCTGATGTTCAAAGAAGGCAGTATGAATATCCACCTGATTGAAGCGGATCTGCGTAAC
Original    TTATTAATGTTTAAAGAAGGTAGTATGAATATCCATTTGATAGAAGCTGACTTAAGAAAC

Optimized   TTCGAAATCAGCAAAACCAACATCTCTCAGAGTACGGAACAGGAAATGGCCAGCCTGTGG
Original    TTTGAAATCTCTAAAACTAATATTTCTCAATCAACTGAACAAGAAATGGCTAGCTTATGG

Optimized   TCTTTCGATGATGCCCGCGCAAAAGCGCAGTTCGAAGAATACAAGAAAAACTACTTCGAA
Original    TCATTTGACGATGCAAGAGCTAAAGCTCAATTTGAAGAATACAAAAAAAATTACTTTGAA

Optimized   GGCAGCCTGGGTGAAGATGATAATCTGGATTTTTCTCAGAACACCGTGGTTGATAAAGAA
Original    GGTTCTCTTGGAGAAGATGACAATCTTGACTTTTCTCAAAATACAGTAGTTGACAAGGAG

Optimized   TACCTGCTGGAAAAAATCAGCTCTCTGGCGCGTAGTAGCGAACGCGGTTACATCCATTAT
Original    TATCTTTTAGAAAAAATATCTTCATTAGCAAGAAGTTCAGAGAGAGGATATATACACTAT

Optimized   ATTGTGCAGCTGCAGGGCGATAAAATCAGCTACGAAGCGGCCTGCAATCTGTTTGCAAAA
Original    ATTGTTCAGTTACAAGGAGATAAAATTAGTTATGAAGCAGCATGTAACTTATTTGCAAAG

Optimized   ACCCCGTATGATAGTGTGTTCTGTTCCAGAAAAAACATTGAAGATAGCGAAATCGCGTATTAC
Original    ACTCCTTATGATAGTGTACTGTTTCAGAAAAATATAGAAGATTCAGAAATTGCATATTAT

Optimized   TATAATCCGGGCGATGGTGAAATCCAGGAAATCGATAAATACAAAATCCCGAGTATCATC
Original    TATAATCCTGGAGATGGTGAAATACAAGAAATAGACAAGTATAAAATTCCAAGTATAATT

Optimized   AGCGATCGCCCGAAAATTAAACTGACCTTTATCGGCCACGGTAAAGATGAATTTAACACG
Original    TCTGATAGACCTAAGATTAAATTAACATTTATTGGTCATGGTAAAGATGAATTTAATACT

Optimized   GATATTTTCGCGGGCCTGGATGTGGATAGCCTGTCTACCGAAATCGAAACGGCAATTGAT
Original    GATATATTTGCAGGTCTTGATGTAGATTCATTATCCACAGAAATAGAAACAGCAATAGAT
```

FIG. 2 (contd.)

```
Optimized    CTGGCGAAAGAAGATATCTCTCCGAAAAGTATCGAAATCAATCTGCTGGGTTGTAACATG
Original     TTAGCTAAAGAGGATATTTCTCCTAAGTCAATAGAAATAAACTTACTGGGATGTAACATG

Optimized    TTTAGTTACAGCGTGAATGTTGAAGAAACCTATCCGGGCAAACTGCTGCTGCGTGTGAAA
Original     TTTAGCTATTCTGTAAATGTAGAGGAGACTTATCCTGGGAAATTATTACTTAGAGTTAAA

Optimized    GATAAAGTTTCTGAACTGATGCCGTCTATCAGTCAGGATTCTATTATCGTGAGTGCCAAT
Original     GATAAAGTATCAGAATTAATGCCATCTATAAGTCAAGACTCTATTATAGTAAGTGCAAAT

Optimized    CAGTATGAAGTTCGCATTAACAGCGAAGGTCGTCGCGAACTGCTGGATCATAGCGGCGAA
Original     CAATATGAAGTTAGAATAAATAGTGAAGGAAGAAGAGAATTATTGGATCATTCTGGTGAA

Optimized    TGGATCAACAAAGAAGAATCTATCATCAAAGATATCTCTAGTAAAGAATACATCAGCTTC
Original     TGGATAAATAAAGAAGAAAGTATTATAAAGGATATTTCATCAAAAGAATATATATCATTT

Optimized    AACCCGAAAGAAAAACAAAATCATCGTGAAAAGTAAAAACCTGCCGGAACTGAGCACCCTG
Original     AATCCTAAAGAAAAATAAAATTATAGTAAAATCTAAAAATTTACCTGAATTATCTACATTA

Optimized    CTGCAGGAAATCCGTAATAACAGCAATAGCTCTGATATTGAACTGGAAGAAAAAGTGATG
Original     TTACAAGAAATTAGAAACAATTCTAATTCAAGTGATATTGAACTAGAAGAAAAAGTAATG

Optimized    CTGGCAGAATGCGAAATCAACGTTATCTCTAACATCGATACCCAGGTGGTTGAAGGTCGC
Original     TTAGCAGAATGTGAGATAAATGTTATTTCAAATATAGATACACAAGTGGTAGAAGGAAGG

Optimized    ATTGAAGAAGCGAAAAGTCTGACGAGCGATTCTATCAACTACATCAAAAACGAATTCAAA
Original     ATTGAAGAAGCTAAAAGCTTAACTTCTGACTCTATTAATTATATAAAGAATGAATTTAAA

Optimized    CTGATTGAAAGTATCAGCGATGCGCTGTATGATCTGAAACAGCAGAACGAACTGGAAGAA
Original     CTAATAGAATCTATTTCTGATGCACTATACGATTTAAAACAACAGAATGAATTAGAAGAG

Optimized    AGCCACTTTATTTCTTTCGAAGATATCCTGGAAACCGATGAAGGTTTCTCTATCCGTTTC
Original     TCTCATTTTATATCTTTTGAGGATATATTGGAGACTGATGAAGGCTTTAGTATAAGATTT

Optimized    ATCGATAAAGAAACCGGCGAAAGTATTTTTGTGGAAACCGAAAAAGCAATCTTCAGCGAA
Original     ATTGATAAAGAAACTGGAGAATCTATATTTGTAGAAACTGAAAAGGCAATATTCTCTGAA

Optimized    TACGCGAACCATATCACCGAAGAAATCTCTAAAATCAAAGGTACCATCTTTGATACGGTG
Original     TATGCTAATCATATAACTGAAGAGATTTCTAAGATAAAAGGTACTATATTTGATACTGTA

Optimized    AACGGCAAACTGGTGAAAAAAGTTAATCTGGATGCCACCCACGAAGTTAACACGCTGAAT
Original     AATGGTAAGTTAGTAAAAAAAGTAAATTTAGATGCTACACATGAAGTGAATACTTTAAAT

Optimized    GCAGCGTTTTTCATCCAGAGCCTGATTGAATACAACAGTAGCAAAGAATCTCTGAGTAAT
Original     GCTGCATTTTTTATACAATCATTAATAGAATATAATAGTTCTAAAGAATCTCTTAGTAAT

Optimized    CTGAGCGTGGCAATGAAAGTGCAGGTTTATGCGCAGCTGTTTTCTACCGGCCTGAACACG
Original     TTAAGTGTAGCAATGAAAGTTCAAGTTTATGCTCAATTATTTAGTACTGGTTTAAATACT

Optimized    ATTACCGATGCCGCAAAAGTGGTTGAACTGGTTAGCACCGCCCTGGATGAAACGATTGAT
Original     ATTACAGATGCAGCCAAAGTTGTTGAATTAGTATCAACTGCATTAGATGAAACTATAGAT
```

FIG. 2 (contd.)

```
Optimized   CTGCTGCCGACCCTGAGCGAAGGTCTGCCGGTGATCGCAACGATTATCGATGGCGTTTCT
Original    TTACTTCCTACATTATCTGAAGGATTACCTGTAATTGCAACTATCATAGATGGTGTAAGT

Optimized   CTGGGTGCGGCCATTAAAGAACTGAGCGAAACCTCTGATCCGCTGCTGCGTCAGGAAATT
Original    TTAGGTGCAGCAATCAAAGAGCTAAGTGAAACAAGTGACCCATTATTAAGACAAGAAATA

Optimized   GAAGCCAAAATTGGCATCATGGCAGTGAATCTGACCGCAGCGACGACCGCAATTATCACG
Original    GAAGCTAAGATAGGTATAATGGCAGTAAATTTAACAGCAGCTACAACTGCAATCATTACT

Optimized   TCTAGTCTGGGCATTGCGAGTGGTTTTAGCATCCTGCTGGTGCCGCTGGCAGGTATCAGT
Original    TCATCTTTAGGAATAGCTAGTGGATTTAGTATACTTTTAGTTCCTTTAGCAGGAATTTCA

Optimized   GCAGGTATTCCGAGCCTGGTTAATAACGAACTGATCCTGCGCGATAAAGCGACCAAAGTG
Original    GCAGGTATACCAAGTTTAGTAAACAATGAGCTTATCCTAAGAGATAAAGCAACAAAAGTT

Optimized   GTTGATTACTTCTCTCATATCAGTCTGGCGGAAAGCGAAGGTGCCTTTACGTCTCTGGAT
Original    GTAGATTATTTTAGTCATATATCATTAGCTGAGTCTGAAGGAGCATTTACTTCATTAGAT

Optimized   GATAAAATTATGATGCCGCAGGATGATCTGGTGATCAGTGAAATCGATTTCAACAACAAC
Original    GATAAAATAATGATGCCACAAGATGATTTAGTAATATCTGAGATAGACTTTAATAACAAT

Optimized   AGCATTACCCTGGGTAAATGTGAAATCTGGCGTATGGAAGGCGGTAGCGGCCATACGGTT
Original    TCAATAACTTTAGGTAAATGTGAAATCTGGAGAATGGAAGGTGGCTCAGGTCATACTGTA

Optimized   ACCGATGATATCGATCACTTTTTCAGCGCCCCGTCTATTACCTACCGCGAACCGCACCTG
Original    ACTGATGATATAGATCACTTCTTTTCAGCACCATCAATAACATATAGAGAGCCACACTTA

Optimized   AGCATCTATGATGTGCTGGAAGTTCAGAAAGAAGAACTGGATCTGTCTAAAGATCTGATG
Original    TCTATATATGACGTATTGGAAGTACAAAAAGAAGAACTTGATTTGTCAAAAGATTTAATG

Optimized   GTGCTGCCGAACGCGCCGAATCGTGTTTTCGCCTGGGAAACGGGTTGGACCCCGGGTCTG
Original    GTATTACCTAATGCTCCAAATAGAGTATTTGCTTGGGAAACAGGATGGACACCAGGTTTA

Optimized   CGTAGCCTGGAAAACGATGGTACCAAACTGCTGGATCGTATTCGCGATAATTACGAAGGC
Original    AGAAGCTTAGAAAATGATGGCACAAAACTGTTAGACCGTATAAGAGATAACTATGAAGGT

Optimized   GAATTTTACTGGCGTTATTTTGCGTTCATTGCCGATGCACTGATCACGACCCTGAAACCG
Original    GAGTTTTATTGGAGATATTTTGCTTTTATAGCTGATGCTTTAATAACAACATTAAAACCA

Optimized   CGTTATGAAGATACCAACATTCGCATCAATCTGGATAGTAACACGCGTAGCTTCATCGTG
Original    AGATATGAAGATACTAATATAAGAATAAATTTAGATAGTAATACTAGAAGCTTTATAGTC

Optimized   CCGGTTATTACGACCGAATATATTCGCGAAAAACTGAGCTACTCTTTTTATGGCAGCGGC
Original    CCAGTGATAACTACAGAATATATAAGAGAGAAATTATCATATTCTTTTTATGGTTCTGGA

Optimized   GGTACCTACGCCCTGAGTCTGAGCCAGTACAACATGAACATCAACATCGAACTGAACGAA
Original    GGAACTTATGCATTATCTCTTTCTCAATACAATATGAATATAAACATAGAATTAAATGAA

Optimized   AACGATACCCTGGGTGATTGATGTTGATAACGTGGTTCGCGATGTGACGATCGAAAGCGAT
Original    AATGATACTTGGGTTATAGATGTCGACAATGTCGTAAGAGATGTCACTATAGAATCTGAT
```

FIG. 2 (contd.)

```
Optimized     AAAATCAAAAAAGGTGATCTGATCGAAAACATCCTGAGTAAACTGAGCATCGAAGATAAC
Original      AAAATTAAAAAAGGAGATTTAATAGAGAATATTTTATCTAAATTAAGTATTGAAGACAAT

Optimized     AAAATCATCCTGGATAACCATGAAATCAACTTTAGCGGTACCCTGAACGGCGGTAATGGC
Original      AAAATTATTTTAGATAATCATGAAATTAATTTCTCTGGAACATTAAATGGAGGTAATGGA

Optimized     TTTGTTTCTCTGACGTTCAGTATCCTGGAAGGTATTAATGCGGTGATCGAAGTTGATCTG
Original      TTTGTATCTTTAACATTCTCAATCTTAGAAGGAATAAATGCAGTTATAGAAGTTGATTTA

Optimized     CTGTCTAAAAGTTATAAAGTGCTGATTAGCGGCGAACTGAAAACCCTGATGGCCAATAGC
Original      TTATCTAAATCATATAAAGTTCTTATTTCTGGTGAACTAAAAACATTGATGGCAAATTCA

Optimized     AACTCTGTTCAGCAGAAAATTGATTACATCGGTCTGAATAGTGAACTGCAGAAAAACATC
Original      AATTCTGTTCAACAGAAAATAGATTATATAGGATTGAACAGCGAATTACAAAAAAATATA

Optimized     CCGTATAGCTTTATGGATGATAAAGGCAAAGAAAACGGTTTCATCAACTGCAGCACCAAA
Original      CCTTATAGTTTTATGGATGATAAAGGAAAAGAAAATGGATTTATTAATTGTTCTACAAAA

Optimized     GAAGGCCTGTTTGTGTCTGAACTGAGTGATGTGGTTCTGATCTCTAAAGTTTACATGGAT
Original      GAAGGTTTATTTGTATCTGAATTATCTGATGTAGTTCTTATAAGTAAAGTTTATATGGAC

Optimized     AACAGTAAACCGCTGTTTGGCTATTGTAGCAATGATCTGAAAGATGTGAAAGTTATCACC
Original      AATAGTAAACCTCTATTTGGATATTGTAGTAATGATTTGAAAGATGTTAAAGTCATAACT

Optimized     AAAGATGATGTGATCATCCTGACGGGTTACTACCTGAAAGATGATATCAAAATCAGTCTG
Original      AAAGATGACGTTATTATATTAACAGGATATTATTTAAAAGATGATATAAAAATCTCTCTT

Optimized     AGCTTCACCATTCAGGATGAAAATACGATCAAACTGAACGGTGTGTATCTGGATGAAAAC
Original      TCTTTTACTATACAAGATGAAAATACTATAAAATTAAATGGAGTATATTTAGATGAAAAT

Optimized     GGCGTTGCGGAAATCCTGAAATTCATGAACAAAAAAGGCAGCACGAACACCTCTGATAGT
Original      GGAGTAGCTGAAATATTGAAATTTATGAATAAAAAAGGTAGTACAAATACTTCAGATTCT

Optimized     CTGATGAGCTTCCTGGAATCTATGAACATCAAATCTATCTTCATCAATAGCCTGCAGTCT
Original      TTAATGAGCTTTTTAGAAAGTATGAATATAAAAAGTATTTTCATAAATTCCTTACAATCT

Optimized     AACACCAAACTGATCCTGGATACGAATTTCATCATCAGTGGCACGACCAGCATTGGCCAG
Original      AATACTAAGCTTATATTAGATACTAATTTTATAATAAGTGGTACTACTTCTATTGGTCAA

Optimized     TTCGAATTCATCTGCGATAAAGATAACAACATCCAGCCGTACTTCATCAAATTCAACACG
Original      TTTGAGTTTATTTGTGATAAAGATAATAATATACAACCATATTTCATTAAGTTTAATACA

Optimized     CTGGAAACCAAATACACGCTGTATGTGGGTAACCGTCAGAATATGATTGTTGAACCGAAC
Original      CTAGAAACTAAATATACTCTATATGTAGGTAATAGACAAAATATGATAGTAGAACCAAAT

Optimized     TATGATCTGGATGATAGTGGTGATATTAGCTCTACCGTGATCAATTTTAGCCAGAAATAC
Original      TATGATTTAGATGATTCTGGAGATATATCTTCAACTGTCATTAATTTTTCTCAGAAATAC
```

FIG. 2 (contd.)

```
Optimized   CTGTATGGCATCGATTCTTGTGTGAACAAAGTTATCATCAGTCCGAACATCTACACCGAT
Original    CTTTATGGAATAGACAGTTGTGTTAATAAAGTTATAATTTCGCCAAATATATATACAGAT

Optimized   GAAATCAACATCACGCCGATCTACGAAGCGAACAATACCTATCCGGAAGTGATTGTTCTG
Original    GAAATAAACATAACACCTATATATGAAGCAAATAATACTTATCCAGAAGTGATTGTATTA

Optimized   GATACGAACTACATCTCTGAAAAAATCAACATCAACATCAACGATCTGAGTATTCGTTAT
Original    GATACAAATTATATAAGTGAAAAAATCAATATTAATATCAATGATTTATCTATACGATAT

Optimized   GTGTGGTCTAACGATGGCAGTGATTTTATCCTGATGAGCACCGATGAAGAAAACAAAGTG
Original    GTATGGAGTAATGATGGAAGTGATTTTATTCTTATGTCAACTGATGAAGAGAACAAGGTA

Optimized   TCTCAGGTTAAAATCCGCTTCACCAACGTTTTCAAGGGTAACACGATCAGCGATAAAATC
Original    TCACAAGTTAAAATAAGATTTACTAATGTTTTTAAAGGTAATACTATATCAGATAAGATA

Optimized   TCTTTCAACTTCAGTGATAAACAGGATGTGAGCATCAACAAAGTTATCTCTACGTTCACC
Original    TCTTTTAATTTTAGTGATAAGCAAGATGTATCTATAAATAAAGTTATTTCAACATTTACA

Optimized   CCGAGTTACTATGTGGAAGGTCTGCTGAACTACGATCTGGGCCTGATTAGCCTGTACAAC
Original    CCTTCATATTATGTGGAAGGATTACTTAATTATGATTTAGGTCTGATTTCTTTATACAAT

Optimized   GAAAAATTCTACATCAACAACTTCGGCATGATGGTGTCTGGTCTGGTTTACATCAACGAT
Original    GAGAAATTTTATATTAATAACTTTGGAATGATGGTGTCTGGATTAGTATATATTAATGAT

Optimized   AGCCTGTACTACTTCAAACCGCCGATTAAAAATCTGATCACCGGCTTCACGACCATCGGT
Original    TCATTATATTATTTCAAGCCACCAATAAAGAACTTGATAACTGGATTTACAACTATAGGT

Optimized   GATGATAAATACTACTTCAACCCGGATAATGGCGGTGCCGCAAGCGTGGGTGAAACCATC
Original    GATGATAAATACTACTTTAATCCAGATAATGGTGGAGCTGCTTCAGTCGGAGAAACAATA

Optimized   ATCGATGGCAAAAACTACTACTTCAGCCAGAACGGCGTGCTGCAGACCGGTGTGTTTAGC
Original    ATTGATGGCAAAAACTACTACTTCAGCCAAAATGGAGTGTTACAAACAGGTGTATTTAGT

Optimized   ACGGAAGATGGCTTTAAATATTTCGCGCCGGCCGATACCCTGGATGAAAATCTGGAAGGT
Original    ACAGAAGATGGATTTAAATATTTTGCTCCAGCAGATACACTTGATGAAAATCTAGAGGGG

Optimized   GAAGCGATCGATTTCACCGGCAAACTGACGATTGATGAAAACGTGTACTACTTCGGTGAT
Original    GAAGCAATTGATTTTACTGGCAAACTAACTATTGATGAAAATGTTTATTATTTTGGAGAT

Optimized   AACTATCGTGCGGCCATTGAATGGCAGACCCTGGATGATGAAGTTTACTACTTCTCTACG
Original    AATTATAGAGCAGCTATAGAATGGCAAACATTAGATGATGAAGTGTACTATTTTAGTACA

Optimized   GATACCGGCCGCGCCTTCAAAGGTCTGAACCAGATCGGCGATGATAAATTCTACTTCAAC
Original    GATACAGGTAGAGCTTTTAAAGGGCTAAATCAAATAGGTGATGATAAATTCTATTTCAAC

Optimized   AGCGATGGTATCATGCAGAAAGGCTTCGTGAACATCAACGATAAAACCTTCTACTTCGAT
Original    TCTGATGGTATTATGCAAAAAGGATTTGTTAATATAAATGATAAGACATTCTATTTTGAT

Optimized   GATAGCGGTGTTATGAAATCTGGCTATACGGAAATCGATGGCAAATACTTTTATTTCGCG
Original    GATTCTGGTGTGATGAAGTCAGGATATACTGAAATAGATGGAAAATATTTTTACTTTGCT
```

FIG. 2 (contd.)

```
Optimized   GAAAACGGTGAAATGCAGATTGGCGTGTTTAATACCGCCGATGGTTTTAAATACTTCGCA
Original    GAGAATGGAGAAATGCAAATAGGAGTATTTAATACAGCAGATGGATTTAAATATTTTGCT

Optimized   CATCACGATGAAGATCTGGGCAACGAAGAAGGTGAAGCCCTGAGCTACTCTGGCATTCTG
Original    CATCATGATGAAGATTTAGGAAATGAAGAAGGTGAAGCACTTTCATATTCTGGTATACTT

Optimized   AACTTCAACAACAAAATCTACTACTTCGATGATAGTTTCACCGCAGTGGTTGGTTGGAAA
Original    AATTTTAACAATAAGATTTATTATTTTGATGATTCATTTACAGCAGTAGTTGGATGGAAG

Optimized   GATCTGGAAGATGGCAGCAAATACTATTTTGATGAAGATACGGCAGAAGCGTATATCGGT
Original    GATTTAGAAGATGGTTCAAAATATTACTTTGATGAAGATACAGCAGAAGCATATATAGGT

Optimized   ATCTCTATCATCAACGATGGCAAATACTACTTCAACGATAGTGGTATCATGCAGATCGGC
Original    ATCTCAATAATTAATGATGGTAAATATTATTTTAATGATTCTGGAATCATGCAAATTGGA

Optimized   TTCGTGACCATCAACAACGAAGTGTTTTATTTCAGTGATAGCGGTATCGTGGAAAGCGGC
Original    TTTGTCACAATAAATAATGAAGTATTTTATTTCTCTGATTCTGGAATAGTAGAATCTGGA

Optimized   ATGCAGAACATCGATGACAACTACTTCTACATCGATGAAAACGGTCTGGTGCAGATTGGC
Original    ATGCAAAATATAGATGATAATTATTTCTATATAGACGAAAATGGTCTAGTTCAAATTGGT

Optimized   GTTTTCGATACCTCTGATGGTTACAAATACTTCGCCCCGGCAAATACGGTGAACGATAAT
Original    GTATTTGACACTTCAGATGGATATAAATACTTTGCACCAGCTAATACTGTAAATGATAAT

Optimized   ATCTACGGCCAGGCAGTTGAATATAGCGGTCTGGTGCGTGTTGGCGAAGATGTGTACTAT
Original    ATCTATGGACAAGCAGTTGAATATAGTGGTTTAGTTAGAGTTGGTGAAGATGTATATTAT

Optimized   TTTGGTGAAACGTACACCATTGAAACCGGCTGGATCTATGATATGGAAAACGAAAGCGAT
Original    TTTGGAGAAACATATACAATTGAGACTGGTTGGATATATGATATGGAAAATGAAAGTGAT

Optimized   AAATACTACTTCGATCCGGAAACGAAAAAAGCGTACAAAGGCATCAACGTTATCGATGAT
Original    AAATATTATTTCGATCCAGAAACTAAAAAAGCATATAAAGGTATTAATGTAATTGATGAT

Optimized   ATCAAATACTACTTCGATGAAAACGGTATTATGCGCACCGGCCTGATCACGTTCGAAGAT
Original    ATAAAATACTATTTTGATGAGAATGGAATAATGAGAACAGGTCTTATAACATTTGAAGAT

Optimized   AACCATTACTACTTCAACGAAGATGGTATCATGCAGTACGGCTACCTGAACATCGAAGAC
Original    AATCATTACTATTTTAATGAAGATGGTATTATGCAATATGGTTATCTAAATATAGAAGAT

Optimized   AAAACGTTCTACTTCTCTGAAGACGGTATCATGCAGATTGGCGTGTTCAATACCCCGGAT
Original    AAGACGTTCTACTTTAGTGAAGATGGTATTATGCAGATTGGAGTATTTAATACACCAGAT

Optimized   GGTTTTAAATATTTCGCCCACCAGAATACGCTGGATGAAAACTTCGAAGGTGAAAGCATC
Original    GGATTTAAATATTTTGCACATCAAAATACTTTAGATGAGAATTTTGAGGGAGAATCAATA

Optimized   AACTACACCGGCTGGCTGGATCTGGATGAAAAACGCTACTATTTCACCGATGAATATATC
Original    AACTATACTGGTTGGTTAGATTTAGATGAAAAGAGATATTATTTTACAGATGAATATATT

Optimized   GCAGCGACGGGTAGTGTGATTATCGATGGCGAAGAATACTATTTTGATCCGGATACCGCA
Original    GCAGCAACTGGTTCAGTTATTATTGATGGTGAGGAGTATTATTTTGATCCTGATACAGCT

Optimized   CAGCTGGTTATTAGCGAATAA
Original    CAATTAGTGATTAGTGAATAG
```

FIG. 2 (contd.)

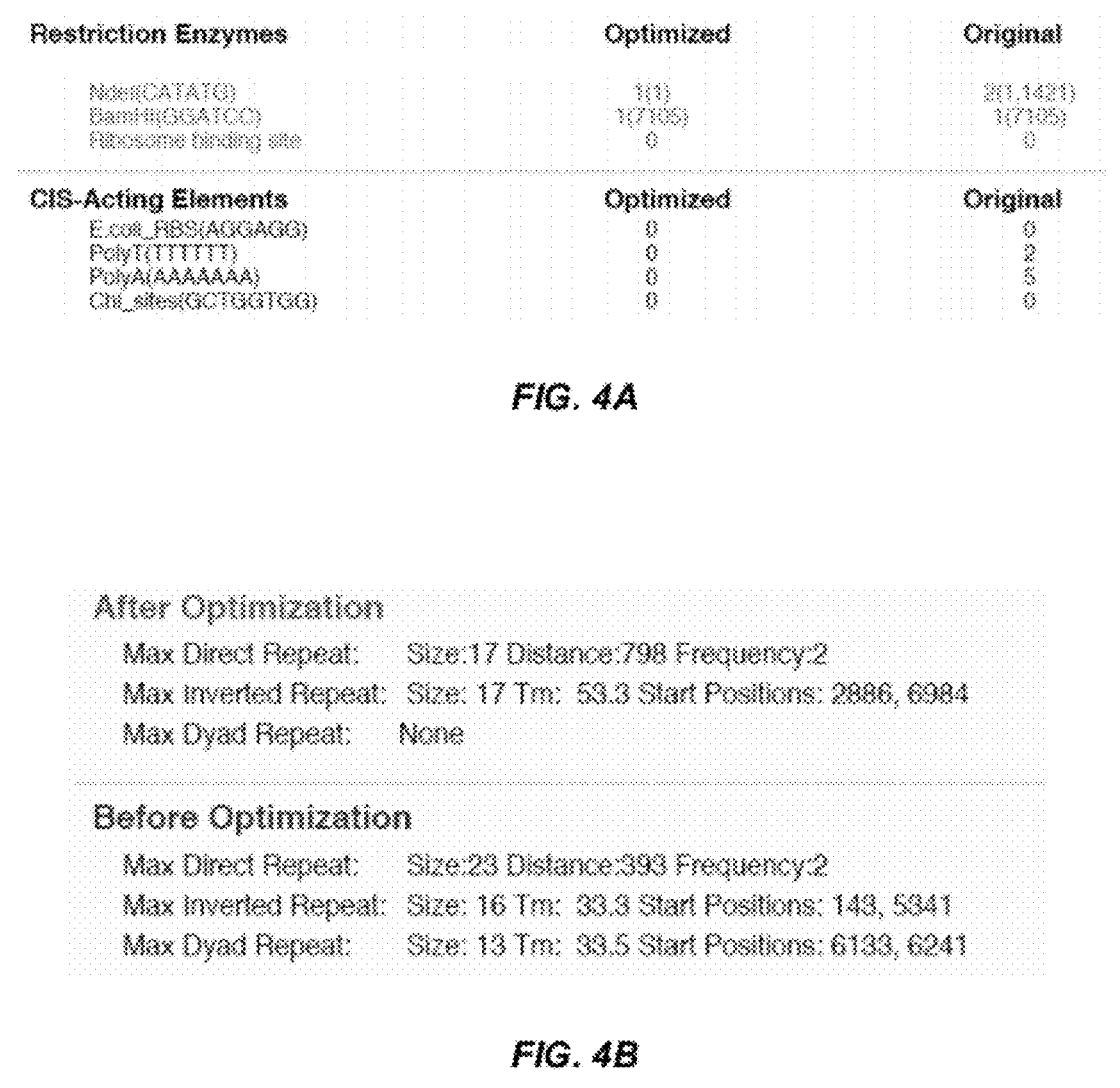

| Restriction Enzymes | Optimized | Original |
|---|---|---|
| NdeI(CATATG) | 1(1) | 2(1,1421) |
| BamHI(GGATCC) | 1(7105) | 1(7105) |
| Ribosome binding site | 0 | 0 |

| CIS-Acting Elements | Optimized | Original |
|---|---|---|
| E.coli_RBS(AGGAGG) | 0 | 0 |
| PolyT(TTTTTT) | 0 | 2 |
| PolyA(AAAAAAA) | 0 | 5 |
| Chi_sites(GCTGGTGG) | 0 | 0 |

*FIG. 4A*

After Optimization

Max Direct Repeat: Size:17 Distance:798 Frequency:2

Max Inverted Repeat: Size: 17 Tm: 53.3 Start Positions: 2886, 6984

Max Dyad Repeat: None

Before Optimization

Max Direct Repeat: Size:23 Distance:393 Frequency:2

Max Inverted Repeat: Size: 16 Tm: 33.3 Start Positions: 143, 5341

Max Dyad Repeat: Size: 13 Tm: 33.5 Start Positions: 6133, 6241

*FIG. 4B*

Optimized MSLVNKKQLEKMANVRFRVQEDEYVAILDALEEYHNMSENTVVEKYLKLKDINSLTDIYI
Original MSLVNKKQLEKMANVRFRVQEDEYVAILDALEEYHNMSENTVVEKYLKLKDINSLTDIYI Optimized DTYKKSGRNKALKKFKEYLVTEVLELKNNNLTPVEKNLHFVWIGGQINDTAINYINQWKD
Original DTYKKSGRNKALKKFKEYLVTEVLELKNNNLTPVEKNLHFVWIGGQINDTAINYINQWKD Optimized VNSDYNVNVFYDSNAFLINTLKKTIVESATNDTLESFRENLNDPRFDYNKFYRKRMEIIY
Original VNSDYNVNVFYDSNAFLINTLKKTIVESATNDTLESFRENLNDPRFDYNKFYRKRMEIIY Optimized DKQKNFINYYKTQREENPDLIIDDIVKIYLSNEYSKDIDELNSYIEESLNKVTENSGNDV
Original DKQKNFINYYKTQREENPDLIIDDIVKIYLSNEYSKDIDELNSYIEESLNKVTENSGNDV Optimized RNFEEFKGGESFKLYEQELVERWNLAAASDILRISALKEVGGVYLDVDMLPGIQPDLFES
Original RNFEEFKGGESFKLYEQELVERWNLAAASDILRISALKEVGGVYLDVDMLPGIQPDLFES Optimized IEKPSSVTVDFWEMVKLEAIMKYKEYIPGYTSEHFDMLDEEVQSSFESVLASKSDKSEIF
Original IEKPSSVTVDFWEMVKLEAIMKYKEYIPGYTSEHFDMLDEEVQSSFESVLASKSDKSEIF Optimized SSLGDMEASPLEVKIAFNSKGIINQGLISVKDSYCSNLIVKQIENRYKILNNSLNPAISE
Original SSLGDMEASPLEVKIAFNSKGIINQGLISVKDSYCSNLIVKQIENRYKILNNSLNPAISE Optimized DNDFNTTTNAFIDSIMAEANADNGRFMMELGKYLRVGFFPDVKTTINLSGPEAYAAAYQD
Original DNDFNTTTNAFIDSIMAEANADNGRFMMELGKYLRVGFFPDVKTTINLSGPEAYAAAYQD Optimized LLMFKEGSMNIHLIEADLRNFEISKTNISQSTEQEMASLWSFDDARAKAQFEEYKRNYFE
Original LLMFKEGSMNIHLIEADLRNFEISKTNISQSTEQEMASLWSFDDARAKAQFEEYKRNYFE Optimized GSLGEDDNLDFSQNTVVDKEYLLEKISSLARSSERGYIHYIVQLQGDKISYEAACNLFAK
Original GSLGEDDNLDFSQNTVVDKEYLLEKISSLARSSERGYIHYIVQLQGDKISYEAACNLFAK Optimized TPYDSVLFQKNIEDSEIAYYYNPGDGEIQEIDKYKIPSIISDRPKIKLTFIGHGKDEFNT
Original TPYDSVLFQKNIEDSEIAYYYNPGDGEIQEIDKYKIPSIISDRPKIKLTFIGHGKDEFNT Optimized DIFAGLDVDSLSTEIETAIDLAKEDISPKSIEINLLGCNMFSYSVNVEETYPGKLLLRVK
Original DIFAGLDVDSLSTEIETAIDLAKEDISPKSIEINLLGCNMFSYSVNVEETYPGKLLLRVK

FIG. 5

| | |
|---|---|
| Optimized | DKVSELMPSISQDSIIVSANQYEVRINSEGRRELLDHSGEWINKEESIIKDISSKEYISF |
| Original | DKVSELMPSISQDSIIVSANQYEVRINSEGRRELLDHSGEWINKEESIIKDISSKEYISF |
| Optimized | NPKENKIIVKSKNLPELSTLLQEIRNNSNSSDIELEEKVMLAECEINVISNIDTQVVEGR |
| Original | NPKENKIIVKSKNLPELSTLLQEIRNNSNSSDIELEEKVMLAECEINVISNIDTQVVEGR |
| Optimized | IEEAKSLTSDSINYIKNEFKLIESISDALYDLKQQNELEESHFISFEDILETDEGFSIRF |
| Original | IEEAKSLTSDSINYIKNEFKLIESISDALYDLKQQNELEESHFISFEDILETDEGFSIRF |
| Optimized | IDKETGESIFVETEKAIFSEYANHITEEISKIKGTIFDTVNGKLVKKVNLDATHEVNTLN |
| Original | IDKETGESIFVETEKAIFSEYANHITEEISKIKGTIFDTVNGKLVKKVNLDATHEVNTLN |
| Optimized | AAFFIQSLIEYNSSKESLSNLSVAMKVQVYAQLFSTGLNTITDAAKVVELVSTALDETID |
| Original | AAFFIQSLIEYNSSKESLSNLSVAMKVQVYAQLFSTGLNTITDAAKVVELVSTALDETID |
| Optimized | LLPTLSEGLPVIATIIDGVSLGAAIKELSETSDPLLRQEIEAKIGIMAVNLTAATTAIIT |
| Original | LLPTLSEGLPVIATIIDGVSLGAAIKELSETSDPLLRQEIEAKIGIMAVNLTAATTAIIT |
| Optimized | SSLGIASGFSILLVPLAGISAGIPSLVNNELILRDKATKVVDYFSHISLAESEGAFTSLD |
| Original | SSLGIASGFSILLVPLAGISAGIPSLVNNELILRDKATKVVDYFSHISLAESEGAFTSLD |
| Optimized | DKIMMPQDDLVISEIDFNNNSITLGKCEIWRMEGGSGHTVTDDIDHFFSAPSITYREPHL |
| Original | DKIMMPQDDLVISEIDFNNNSITLGKCEIWRMEGGSGHTVTDDIDHFFSAPSITYREPHL |
| Optimized | SIYDVLEVQKEELDLSKDLMVLPNAPNRVFAWETGWTPGLRSLENDGTKLLDRIRDNYEG |
| Original | SIYDVLEVQKEELDLSKDLMVLPNAPNRVFAWETGWTPGLRSLENDGTKLLDRIRDNYEG |
| Optimized | EFYWRYFAFIADALITTLKPRYEDTNIRINLDSNTRSFIVPVITTEYIREKLSYSFYGSG |
| Original | EFYWRYFAFIADALITTLKPRYEDTNIRINLDSNTRSFIVPVITTEYIREKLSYSFYGSG |
| Optimized | GTYALSLSQYNMNINIELNESDTWVIDVDNVVRDVTIESDKIKKGDLIENILSKLSIEDN |
| Original | GTYALSLSQYNMNINIELNESDTWVIDVDNVVRDVTIESDKIKKGDLIENILSKLSIEDN |
| Optimized | KIILDNHEINFSGTLNGGNGFVSLTFSILEGINAVIEVDLLSKSYKVLISGELKTLMANS |
| Original | KIILDNHEINFSGTLNGGNGFVSLTFSILEGINAVIEVDLLSKSYKVLISGELKTLMANS |

FIG. 5 (contd.)

| | |
|---|---|
| Optimized | NSVQQKIDYIGLNSELQKNIPYSFMDDKGKENGFINCSTKEGLFVSELSDVVLISKVYMD |
| Original | NSVQQKIDYIGLNSELQKNIPYSFMDDKGKENGFINCSTKEGLFVSELSDVVLISKVYMD |
| | |
| Optimized | NSKPLFGYCSNDLKDVKVITKDDVIILTGYYLKDDIKISLSFTIQDENTIKLNGVYLDEN |
| Original | NSKPLFGYCSNDLKDVKVITKDDVIILTGYYLKDDIKISLSFTIQDENTIKLNGVYLDEN |
| | |
| Optimized | GVAEILKFMNKKGSTNTSDSLMSFLESMNIKSIFINSLQSNTKLILDTNFIISGTTSIGQ |
| Original | GVAEILKFMNKKGSTNTSDSLMSFLESMNIKSIFINSLQSNTKLILDTNFIISGTTSIGQ |
| | |
| Optimized | FEFICDKDNNIQPYFIKFNTLETKYTLYVGNRQNMIVEPNYDLDDSGDISSTVINFSQKY |
| Original | FEFICDKDNNIQPYFIKFNTLETKYTLYVGNRQNMIVEPNYDLDDSGDISSTVINFSQKY |
| | |
| Optimized | LYGIDSCVNKVIISPNIYTDEINITPIYEANNTYPEVIVLDTNYISEKINININDLSIRY |
| Original | LYGIDSCVNKVIISPNIYTDEINITPIYEANNTYPEVIVLDTNYISEKINININDLSIRY |
| | |
| Optimized | VWSNDGSDFILMSTDEENKVSQVKIRFTNVFKGNTISDKISFNFSDKQDVSINKVISTFT |
| Original | VWSNDGSDFILMSTDEENKVSQVKIRFTNVFKGNTISDKISFNFSDKQDVSINKVISTFT |
| | |
| Optimized | PSYYVEGLLNYDLGLISLYNEKFYINNFGMMVSGLVYINDSLYYFKPPIKNLITGFTTIG |
| Original | PSYYVEGLLNYDLGLISLYNEKFYINNFGMMVSGLVYINDSLYYFKPPIKNLITGFTTIG |
| | |
| Optimized | DDKYYFNPDNGGAASVGETIIDGKNYYFSQNGVLQTGVFSTEDGFKYFAPADTLDENLEG |
| Original | DDKYYFNPDNGGAASVGETIIDGKNYYFSQNGVLQTGVFSTEDGFKYFAPADTLDENLEG |
| | |
| Optimized | EAIDFTGKLTIDENVYYFGDNYRAAIEWQTLDDEVYYFSTDTGRAFKGLNQIGDDKFYFN |
| Original | EAIDFTGKLTIDENVYYFGDNYRAAIEWQTLDDEVYYFSTDTGRAFKGLNQIGDDKFYFN |
| | |
| Optimized | SDGIMQKGFVNINDKTFYFDDSGVMKSGYTEIDGKYFYFAENGEMQIGVFNTADGFKYFA |
| Original | SDGIMQKGFVNINDKTFYFDDSGVMKSGYTEIDGKYFYFAENGEMQIGVFNTADGFKYFA |
| | |
| Optimized | HHNEDLGNEEGEALSYSGILNFNNKIYYFDDSFTAVVGWKDLEDGSKYYFDEDTAEAYIG |
| Original | HHNEDLGNEEGEALSYSGILNFNNKIYYFDDSFTAVVGWKDLEDGSKYYFDEDTAEAYIG |
| | |
| Optimized | ISIINDGKYYFNDSGIMQIGFVTINNEVFYFSDSGIVESGMQNIDDNYFYIDENGLVQIG |
| Original | ISIINDGKYYFNDSGIMQIGFVTINNEVFYFSDSGIVESGMQNIDDNYFYIDENGLVQIG |

FIG. 5 (contd.)

```
Optimized      VFDTSDGYKYFAPANTVNDNIYGQAVEYSGLVRVGEDVYYFGETYTIETGWIYDMENESD
Original       VFDTSDGYKYFAPANTVNDNIYGQAVEYSGLVRVGEDVYYFGETYTIETGWIYDMENESD

Optimized      KYYFDPETKKAYKGINVIDDIKYYFDENGIMRTGLITFEDNHYYFNEDGIMQYGYLNIED
Original       KYYFDPETKKAYKGINVIDDIKYYFDENGIMRTGLITFEDNHYYFNEDGIMQYGYLNIED

Optimized      KTFYFSEDGIMQIGVFNTPDGFKYFAHQNTLDENFEGESINYTGWLDLDEKRYYFTDEYI
Original       KTFYFSEDGIMQIGVFNTPDGFKYFAHQNTLDENFEGESINYTGWLDLDEKRYYFTDEYI

Optimized      AATGSVIIDGEEYYFDPDTAQLVISE*
Original       AATGSVIIDGEEYYFDPDTAQLVISE*
```

*FIG. 5 (contd.)*

BACTERIAL CELLS, OPTIMIZED NUCLEOTIDE SEQUENCES AND METHODS FOR IMPROVED EXPRESSION OF RECOMBINANT *CLOSTRIDIUM DIFFICILE* TOXIN B

STATEMENT REGARDING FEDERALLY SPONSORED RESEARCH

This invention was made with government support under grant number HL084489, awarded by the National Institutes of Health. The government has certain rights in the invention.

FIELD OF THE INVENTION

The present invention generally pertains to the field of protein expression. More particularly, but not by way of limitation, the present invention pertains to the field of expression of bacterial toxins, such as the expression of recombinant *Clostridium difficile* toxin B.

BACKGROUND OF THE INVENTION

*Clostridium difficile* (*C. difficile*) toxin B is a critical virulence factor that contributes to numerous illnesses. Accordingly, toxin B is a target for diagnosis and vaccination. In particular, since *C. difficile* is now the leading cause of hospital-acquired illnesses in the world, an abundant supply of toxin B and/or protein fragments of toxin B is needed to develop vaccines and detection systems. However, current protein expression methods and systems do not generate sufficient amounts of toxin B. Thus, there is currently a need for improved systems and methods to express and purify sufficient amounts of recombinant *C. difficile* toxin B.

BRIEF SUMMARY OF THE INVENTION

In some embodiments, the present disclosure provides methods for improved expression of recombinant *C. difficile* toxin B. Such methods generally include the optimization of a nucleotide sequence that encodes *C. difficile* toxin B for improved expression in a bacterial host cell, such as *Escherichia coli*. In some embodiments, the optimization may include the identification of one or more codons in the nucleotide sequence that rarely appear in the bacterial host cell, and the replacement of these rare codons with one or more codons that more frequently appear in the bacterial host cell. Thereafter, the optimized nucleotide sequence can be introduced into the bacterial host cell. This may then be followed by induction of toxin B expression from the nucleotide sequence. Thereafter, the expressed toxin B may be purified by standard protein purification methods.

Other embodiments of the present disclosure pertain to isolated nucleotide sequences that encode *C. difficile* toxin B. In such embodiments, the isolated nucleotide sequences have been optimized for improved expression of toxin B in a bacterial cell, in accordance with the methods of the present disclosure. In various embodiments, the isolated nucleotide sequences of the present disclosure encode an antigenic portion of toxin B or full-length toxin B. In other embodiments, the isolated nucleotide sequences of the present disclosure have been mutagenized to encode an inactive form of *C. difficile* toxin B. In more specific embodiments, the isolated nucleotide sequences of the present disclosure may include one of SEQ ID NOS. 1-11. In further embodiments, the isolated nucleotide sequences of the present disclosure may be flanked by restriction enzyme sites (e.g., SEQ ID NO. 11).

In other embodiments, the isolated nucleotide sequences of the present disclosure may be in an expression vector, such as pET15b.

In further embodiments, the present disclosure pertains to bacterial cells, such as *E. coli*, that include optimized nucleotide sequences of the present disclosure. In additional embodiments, the present disclosure pertains to isolated peptide sequences of recombinant *C. difficile* toxin B that have been derived from the optimized nucleotide sequences of the present disclosure. In more specific embodiments, the isolated peptide sequences may include at least one of SEQ ID NOS. 12-17.

The methods, nucleotide sequences and bacterial cells of the present disclosure have various applications. For instance, in some embodiments, the various aspects of the present disclosure may be applied to vaccine development. Likewise, in other embodiments, the various aspects of the present disclosure may be applied to protein detection and/or diagnostic systems.

BRIEF DESCRIPTION OF THE DRAWINGS

For a more complete understanding of the present disclosure, and the advantages thereof, reference is now made to the following descriptions to be taken in conjunction with the accompanying Figures describing specific embodiments of the disclosure, wherein:

FIG. 1 is a codon frequency table of *Escherichia coli;*

FIG. 2 shows an alignment of an optimized version of the full-length *C. difficile* NAP1 toxin B gene (SEQ ID NO.1) with the native full-length toxin B gene (SEQ ID NO.2);

FIG. 4A summarizes the optimized restriction enzyme sites and cis acting elements in SEQ ID NO.1;

FIG. 4B summarizes the optimized remove repeat sequences in SEQ ID NO.1;

FIG. 5 shows an alignment of the peptide sequence encoded by SEQ ID NO.1 with the peptide sequence encoded by the native full-length toxin B gene (SEQ ID NO.2);

BRIEF DESCRIPTION OF THE SEQUENCE LISTINGS

Figure 3:
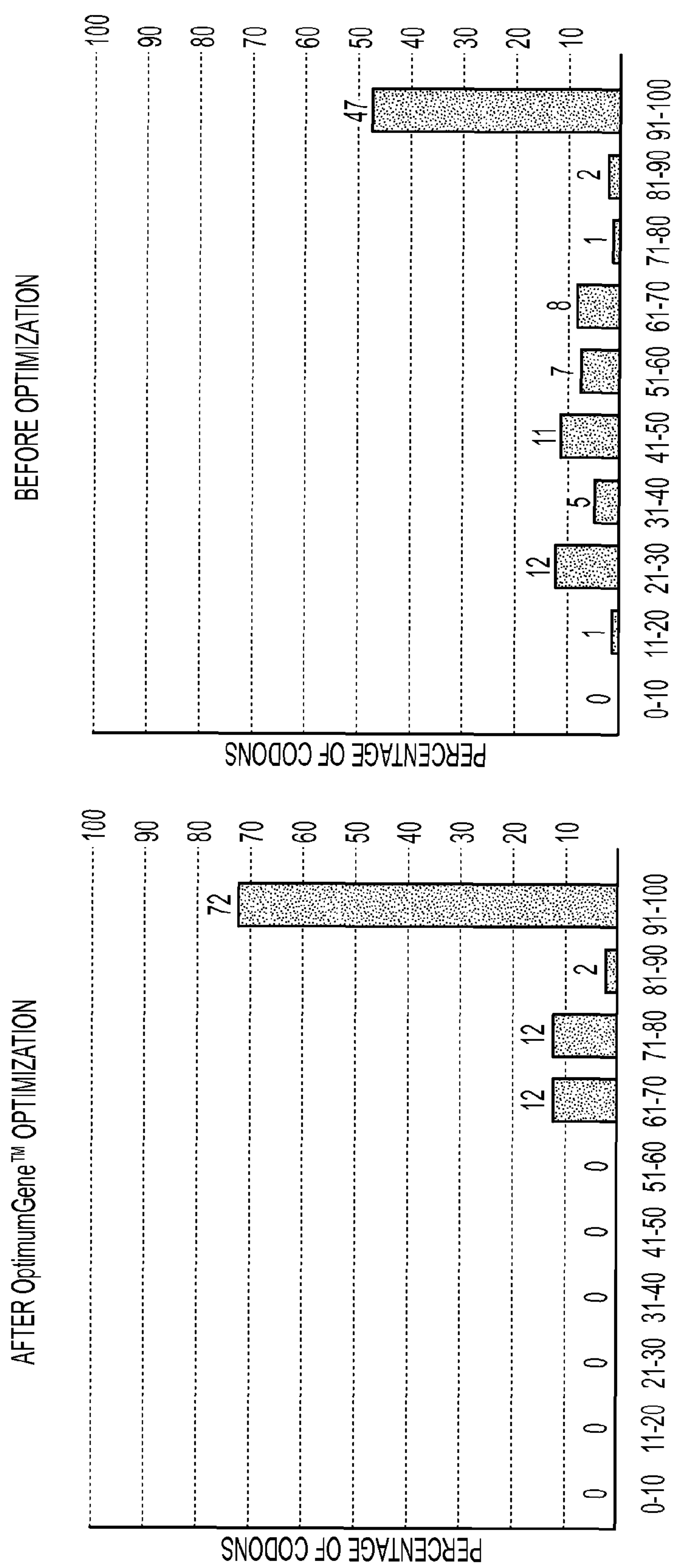
FIG. 3 shows the frequency of optimal codons in SEQ ID NO.1 before and after optimization.

SEQ ID NO.1 is the full length optimized *C. difficle* NAP1 toxin B nucleotide sequence;

SEQ ID NO.2 is the full length native *C. difficle* NAP1 toxin B nucleotide sequence;

SEQ ID NO.3 is the nucleotide sequence of the antigenic portion (C-terminal or receptor-binding domain) of optimized *C. difficle* NAP1 toxin B;

SEQ ID NO.4 is the nucleotide sequence of the antigenic' (C-terminal or receptor-binding domain) portion of native *C. difficle* NAP1 toxin B;

SEQ ID NO.5 is the full length optimized *C. difficle* 10463 toxin B nucleotide sequence;

SEQ ID NO.6 is the nucleotide sequence of the antigenic (C-terminal or receptor-binding domain) portion of native *C. difficle* 10463 toxin B SEQ ID NO.7 is the full length optimized *C. difficle* NAP1 toxin B polypeptide having a point mutation (W102A);

SEQ ID NO.8 is the full length optimized *C. difficle* NAP1 toxin B polypeptide having two point mutations (D286G; D288G);

SEQ ID NO.9 is the full length optimized *C. difficle* 10463 toxin B polypeptide having a point mutation (W102A);

SEQ ID NO.10 is the full length optimized *C. difficle* 10463 toxin B polypeptide having two point mutations (D286G; D288G);

SEQ ID NO.11 is the full length optimized *C. difficle* NAP1 toxin B polynucleotide sequence with restriction sites at each end (NdeI at the 5' end and BamHI at the 3' end);

SEQ ID NO.12 is a polypeptide encoded by SEQ ID NO. 7;

SEQ ID NO.13 is a polypeptide encoded by SEQ ID NO. 8;

SEQ ID NO.14 is a polypeptide encoded by SEQ ID NO. 9;

SEQ ID NO.15 is a polypeptide encoded by SEQ ID NO. 10;

SEQ ID NO.16 is the C-terminal portion of optimized *C. difficle* NAP1 toxin B; and SEQ ID NO.17 which represents the C-terminal portion of optimized *C. difficle* 10463 toxin B.

DETAILED DESCRIPTION OF EXEMPLARY EMBODIMENTS

The particulars shown herein are, by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the Description or Examples below or when application of the meaning renders any construction meaningless or essentially meaningless. In cases where the construction of the term would render it meaningless or essentially meaningless, the definition should be taken from Webster's Dictionary, 3rd Edition.

The present disclosure generally relates to bacterial cells, isolated nucleotide sequences, and methods for expressing recombinant *C. difficile* toxin B, the causative agent of antibiotic-associated diarrhea. Because toxin B contributes to illness, it is a natural target for diagnosis and vaccination. However, the purification of recombinant toxin B (or toxin B fragments) is difficult by current methods. For instance, the use of standard prokaryotic expression systems, such as *E. coli*, yields low amounts of recombinant toxin B protein. Without being bound by theory, it is envisioned that the low expression of recombinant toxin B in such prokaryotic expression systems is the result of the expression of toxin B outside of its original context (i.e. from the original host cell). Particularly, it is envisioned that various parameters can lead to the poor expression of recombinant toxin B in prokaryotic expression systems. Such parameters include, without limitation, codon usage, GC content, CpG dinucleotide content, mRNA secondary structure, repeat sequences, and restriction sites.

By way of background, codon bias is the tendency of an organism to unequally use synonymous codons in a codon family. For instance, FIG. 1 summarizes the codon frequency table for *E. coli*. Codon bias can hinder gene expression because the hyperexpression of a foreign gene using a prokaryotic expression system (such as *E. coli* or similar host) can lead to a depletion of the host cell's endogenous pool of corresponding tRNA. This in turn may profoundly impact protein expression.

To address the above-mentioned problems, the present disclosure provides bacterial cells, nucleotide sequences, and methods for improved expression of recombinant toxin B in bacterial host cells. More specifically, the present disclosure generally pertains to the optimization of an isolated nucleotide sequence that encodes toxin B for improved expression in a bacterial host cell. In other embodiments, the nucleotide sequences of the present disclosure may also be mutagenized to express an inactive form of toxin B. The present disclosure also pertains to the isolation of the optimized polynucleotide sequences, their introduction into the bacterial host cells, their expression in the bacterial cells, and their subsequent purification. The various steps and components of the present disclosure will now be discussed in more detail below.

Optimized Nucleotide Sequences Encoding *Clostridium difficile* Toxin B

As set forth previously, various aspects of the present disclosure pertain to optimized nucleotide sequences that encode *C. difficile* toxin B. The isolated nucleotide sequences of the present disclosure have been optimized to lead to improved expression of toxin B in a host bacterial cell, such as *E. coli*. In some embodiments, the optimized nucleotide sequences of the present disclosure have also been mutagenized to encode an inactive form of *C. difficile* toxin B. Inactive forms of *C. difficile* toxin B are particularly useful in therapeutic applications because they encode a non-toxic, inactive form of toxin B.

Optimization Methods

In the present disclosure, optimization generally occurs by changing one or more codons in a nucleotide sequence encoding *C. difficile* toxin B. In some embodiments, the optimization includes the identification of one or more codons that rarely appear in a bacterial host cell, and the subsequent replacement of the identified codons with one or more codons that more frequently appear in the bacterial cell. Optimal codons may be defined in several ways. These include the basis of availability of tRNA; the nature of the codon-anticodon interaction; and those codons that occur in high-expression genes significantly more frequently than they occur in low expression genes.

In some embodiments, the optimization may be performed manually, such as by manual sequence analysis. In other embodiments, the optimization may be performed automatically, such as by the use of analytical software. In a more specific embodiment, the optimization may be performed by the utilization of the OptimumGene™ algorithm by GenScript. This specific embodiment will be discussed in more detail below. In further embodiments, the optimization may be performed by both automatic and manual methods. FIG. 3 shows the frequency of optimal codons in SEQ ID NO.1 before and after optimization.

Isolation of Optimized Nucleotide Sequences

Upon optimization, the nucleotide sequences of the present disclosure may be isolated by various methods that are well known to persons of ordinary skill in the art. For instance, in some embodiments, the optimized nucleotide sequences may be isolated by in vitro polynucleotide synthesis. Such methods may be automated, manual, or both.

FIG. 2 shows an alignment of an optimized *C. difficle* NAP1 toxin B nucleotide sequence (SEQ ID NO.1) with the native full-length NAP1 toxin B gene (SEQ ID NO.2).

Attributes of Optimized Nucleotide Sequences

In some embodiments, optimized nucleotide sequences of the present disclosure encode full-length *C. difficile* toxin B. In other embodiments, the optimized sequences encode a partial fragment of *C. difficile* toxin B, such as an antigenic region (e.g., the receptor binding domain or the C-terminal region of toxin B). In more specific examples, the optimized nucleotide sequences of *C. difficile* toxin B may include one of SEQ ID NOS.1, 3, and 5-11.

The optimized nucleotide sequences of the present disclosure may be derived from various strains of *C. difficile*. For instance, in various embodiments, the optimized nucleotide sequences of the present disclosure encode *C. difficile* toxin B from various pathogenic strains of *C. difficle* that comprise the toxin B gene.

In some embodiments, the optimized nucleotide sequences of the present disclosure may also be flanked by restriction enzyme sites for convenient insertion of the nucleotide sequence into a suitable expression vector. Such restriction enzyme sites are well known in the art and include, without limitation, restriction enzyme sites for BamHI, EcoRI, NdeI and HindIII. SEQ ID NO.9 provides an example of an optimized and isolated nucleotide sequence of the present disclosure that is flanked by two restriction enzyme sites (BamHI at the 3' end and NdeI at the 5' end).

In more specific embodiments, the optimized nucleotide sequences of the present disclosure may also be mutagenized to encode an inactive form of toxin B. Applicants envision that such mutagenized nucleotide sequences can be used to express inactive forms of toxin B for numerous purposes, such as vaccine development and basic research. In some embodiments, the mutagenesis may occur automatically or manually during optimization. In other embodiments, the mutagenesis may occur before or after optimization. In further embodiments, the mutagenesis may occur by site-directed mutagenesis methods that are well known by persons of ordinary skill in the art. Specific examples of optimized nucleotide sequences that have also been mutagenized include, without limitation, SEQ ID NOS.7-10. These nucleotide sequences will be discussed in greater detail below.

Expression Vectors

In some embodiments, the optimized nucleotide sequences of the present disclosure may be, inserted into an expression vector. For instance, in some embodiments, the optimized nucleotide sequences may be ligated into an *E. coli*-specific expression vector by using suitable restriction enzyme sites on the nucleotide sequence. Suitable expression vectors are well known to persons of ordinary skill in the art. In some embodiments, the expression vectors are IPTG-inducible expression vectors. Non-limiting examples include pET expression vectors (e.g., pET-15b), pGEX expression vectors (e.g., pGEX-6P), and pFlag expression vectors (e.g., pFlag-CMV-6a).

As set forth in more detail below, recombinant toxin B from optimized nucleotide sequences of the present disclosure may be expressed by various methods. In some embodiments, toxin B from optimized nucleotide sequences may be expressed in bacterial host cells, such as *E. coli*. In other embodiments, toxin B may be expressed in vitro, such as by using an in vitro translation system.

Bacterial Cells with Optimized Nucleotide Sequences

Some embodiments of the present disclosure also provide bacterial cells that contain an optimized nucleotide sequence encoding *C. difficile* toxin B. In some embodiments, the optimized nucleotide sequence may be genetically incorporated into the bacterial genome by standard microbial genetic methods that are well known to persons of ordinary skill in the art. In other embodiments, the optimized nucleotide sequences may be introduced into the bacterial cell as part of expression vectors that were previously described. In some embodiments, the optimized nucleotide sequences of the present disclosure may be introduced into the bacterial cells by transformation.

In various embodiments, transformation can be performed by common transformation methods, such as "pore-forming" techniques (e.g., electrical or chemical modification of the host bacterium) that allow for the passage of foreign DNA into the host bacterium. Other suitable transformation methods can also be envisioned by persons of ordinary skill in the art.

Various bacterial host cells may be used to express toxin B from optimized nucleotide sequences of the present disclosure. For instance, in some embodiments, the bacterial cell may be *E. coli*, and more specifically the BL21 strain. In other embodiments, the bacterial cell may be *Salmonella typhimurium* or *Bacillus megaterium*. In other embodiments, the bacterial cell may be any bacteria that is suitable for use as a prokaryotic expression system.

Applicants envision numerous advantages to using the above-mentioned bacterial host cells. Such advantages include, without limitation: (1) easy culture techniques and rapid growth; (2) controlled and inducible expression of proteins; (3) simple subsequent protein purification that often uses commercially available kits and reagents; and (4) protein expression and purification that can be easily scaled up to produce large quantities of recombinant toxin B. This is especially important for pharmaceutical companies that require large amounts of protein for testing and vaccine development.

Toxin B Expression in Bacterial Cells

In some embodiments of the present disclosure, the expression of toxin B in the above described bacterial cells may be induced by exposing the bacterial cells to IPTG. In such embodiments, the optimized nucleotide sequence encoding toxin B may be on an IPTG-inducible expression vector, as previously described. In other embodiments, induction may not be necessary or essential to toxin B expression (e.g., where the nucleotide sequence is incorporated into the bacterial genome without any inducible markers). Thereafter, Toxin B may be purified by various methods.

Purification of Toxin B from Bacterial Cells

Generally, toxin B purification entails a substantial separation of expressed toxin B from the lysates of bacterial host cells. Various methods may be used to purify the expressed toxin B. For instance, where a pET vector is used to express toxin B, the toxin B will have a $His_6$ tag that can be purified by $Ni^{+2}$-based systems, such as Qiagen Ni-NTA beads (e.g., Ni-NTA magnetic agarose beads, Ni-NTA agarose beads, and the like) and/or GE HisTrap HP Columns. Likewise, if a pGEX vector is used to express toxin B, the toxin B will have a gluthathione sepharose transferase (GST) tag that can be purified by suitable gluthathione beads, such as Pierce's gluthathione agarose beads. Similarly, if a pFlag vector is used to express toxin B, the toxin B will have a Flag peptide that can be purified by anti-Flag antibodies. Anion exchange chromatography may also be used in some embodiments of the present disclosure. In further embodiments, the purified proteins may also be desalted by various methods (e.g., by GE PD-10 columns). Other modes of purification can also be envisioned by persons of ordinary skill in the art.

In vitro Translation of Toxin B

In some embodiments, the present disclosure also pertains to in vitro translation systems for expressing toxin B. Such systems generally include an optimized nucleotide sequence that encodes toxin B (as previously described), and additional components that are necessary to implement protein translation. In some embodiments, the in vitro translation systems of the present disclosure are cell-free extract systems, such as bacterial cell lysates. In some embodiments, the bacterial cell lysates may be derived from *E. coli.*

Isolated Peptide Sequences

Various other embodiments of the present disclosure pertain to isolated peptide sequences of recombinant toxin B. In some embodiments, the isolated peptide sequences were expressed or derived from the isolated nucleotide sequences, bacterial cells and methods of the present disclosure. In more specific embodiments, the isolated peptide sequences include one of SEQ ID NOS.12-15 which includes the respective peptide sequences for nucleotide sequences SEQ ID NOS.7-10. In other embodiments, the isolated peptide sequences include SEQ ID NO:16 which represents the C-terminal portion of optimized *C. difficile* NAP1 toxin B and SEQ ID NO:17 which represents the C-terminal portion of optimized *C. difficle* 10463 toxin B.

Applications

A person of ordinary skill in the art will recognize that the bacterial cells, isolated nucleotide sequences, and methods of the present disclosure may be used in various settings and for numerous purposes. For instance, in some embodiments, various aspects of the present disclosure may be used for therapeutic and/or vaccination purposes. Various aspects of the present disclosure may also be used for developing disease detection assays. More particularly, in some embodiments, the optimized nucleotide sequences of the present disclosure may be isolated, inserted into an IPTG-inducible plasmid, transformed into *E. coli*, and expressed by IPTG induction. Thereafter, the expressed toxin B may be purified and used to develop vaccines against toxin B (for such purposes, the nucleotide sequence may also be mutagenized to express an inactive form of toxin B). In similar embodiments, the same methodology may be used to purify recombinant toxin B to develop anti-toxin B antibodies for numerous purposes, such as for diagnostic and/or detection assays.

From the above disclosure, a person of ordinary skill in the art will recognize that the present invention has numerous embodiments and applications. Reference will now be made to more specific embodiments of the present invention and experimental results that provide support for such embodiments. However, Applicants note that the disclosure below is for exemplary purposes only and is not intended to limit the scope of the present invention in any way.

WORKING EXAMPLES

Example 1

Optimization of *C. difficile* NAP1 Toxin B gene (SEQ ID NO.1)

The full-length DNA sequence for the *C. difficile* NAP1 toxin B gene was provided to GenScript for optimization of expression in *E. coli*. Thereafter, GenScript utilized the OptimumGene™ algorithm to optimize a variety of parameters that are relevant to the efficiency of toxin B gene expression in *E. coli*, including, but not limited to: codon usage bias; GC content; CpG dinucleotides content; mRNA secondary structure; cryptic splicing sites; premature PolyA sites; internal chi sites and ribosomal binding sites; negative CpG islands; RNA instability motif (ARE); inhibition sites (INS); repeat sequences (direct repeat, reverse repeat, and Dyad repeat); and restriction sites that may interfere with cloning.

For instance, GenScript utilized the codon frequency table of *E. coli* in FIG. 1 to evaluate codon bias.

The result of the optimization was the generation of SEQ. ID. NO.1. FIG. 2 shows an alignment of this optimized sequence with the native (non-optimized) *C. Difficile* NAP1 Toxin B gene. Likewise, FIG. 3 shows the frequency of optimal codons in SEQ ID NO. 1 before and after optimization. This illustrates the percentage distribution of codons in computed codon quality groups. The value of 100 is set for the codon with the highest usage frequency for a given amino acid in the desired expression organism.

FIGS. 4A-4B summarize the optimization of restriction enzyme sites, cis acting elements, and remove repeat sequences in SEQ ID NO.1. In particular, the Stem-Loop structures, which impact ribosomal binding and stability of mRNA, were broken. In addition, the optimization process screened and modified cis-acting sites.

Finally, FIG. 5 illustrates an alignment of the peptide sequence encoded by optimized SEQ ID NO.1 with the peptide sequence encoded by the native gene (*C. difficile* NAP1 toxin B) (SEQ ID NO.2). As shown, the peptide sequence remained unchanged, despite the optimization.

Example 2

Optimization of the Antigenic Region of *C. difficile*'s NAP1 Toxin B Gene (SEQ ID NO.3)

The same process specified in Example 1 was repeated with the antigenic portion of the NAP1 Toxin B gene. Like SEQ. ID. NO.1 in Example 1, the peptide sequence encoded by optimized SEQ. ID. NO.3 remained unchanged (data not shown).

Example 3

Mutagenesis of Optimized Toxin B Sequences

To create inactive forms of toxin B, the optimized toxin B genes were mutagenized by site directed mutagenesis. The mutagenesis was carried out using Stratagene's QuikChange II XL site directed mutagenesis kit and the manufacturer's protocol This resulted in the generation of various inactive forms of toxin B genes, including SEQ ID NOS.7-10. Table 1 below provides a summary of optimized and mutagenized nucleotide sequences encoding *C. difficile* toxin B:

TABLE 1

| SEQ ID NO. | *C. difficile* Strain | Mutagenized Sites(s) |
|---|---|---|
| 7 | Full-length NAP1 | W102A |
| 8 | Full-length NAP1 | D286G, D288G |
| 9 | Full-length 10463 | W102A |
| 10 | Full-length 10463 | D286G, D288G |

Example 4

Synthesis and Cloning of Toxin B Nucleotide Sequences in a pET Expression Vector The process of synthesis and cloning of the various nucleotide sequences into a pET expression vector was carried out using standard molecular biology techniques.

Example 5

Expression of Recombinant Proteins in *E. Coli*

Figure 6:
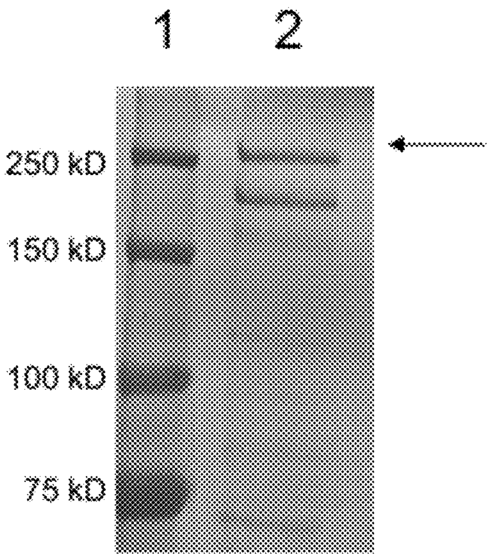
FIG. 6 shows a Coomassie-stained gel containing recombinant full-length NAP-toxin B obtained from SEQ ID NO. 1 expressed in *E. coli* BL 21 cells (rTcdB-NAP1). The product was first isolated from a HisTrap column, followed by purification via anion exchange.
Figure 7:
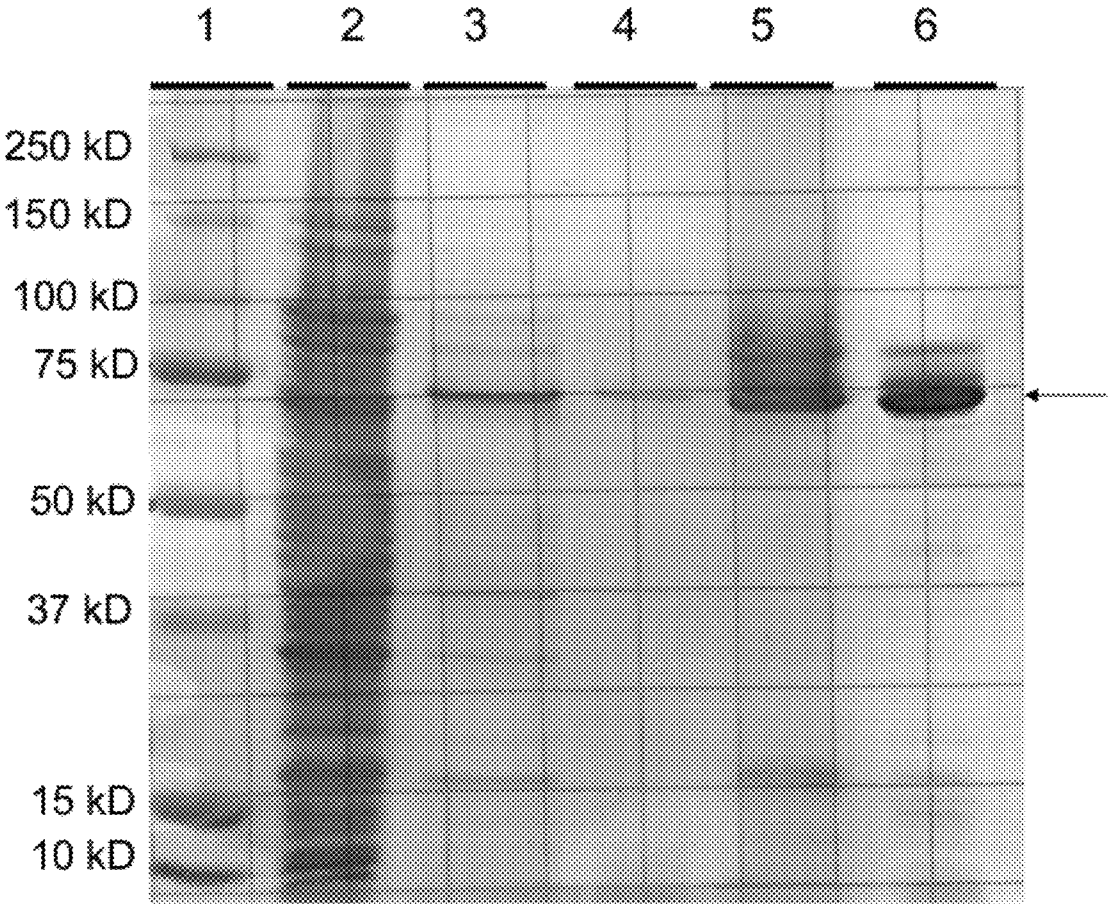
FIG. 7 shows a Coomassie-stained gel containing samples collected during the expression and purification of the rTcdB Receptor Binding Domain of Toxin B 10463 in *E. coli* BL 21 cells.

A pET expression vector containing at least one of sequences SEQ ID NO: 1-11 was transformed into *E. coli* BL21 cells. The transformed cells were subjected to standard recombinant expression protocols in order to express and purify the recombinant protein. FIGS. 6 and 7 illustrate the results of expression and purification of the recombinant proteins of the claimed invention. FIG. 6 shows a Coomassie-stained gel containing recombinant full-length NAP-1 Toxin B obtained from SEQ ID NO. 1 expressed in *E. coli* BL 21 cells (rTcdB-NAP1). The product was first isolated from a HisTrap column, then purified by anion exchange. FIG. 7 shows a Coomassie-stained gel containing samples collected during the expression and purification of the rTcdB Receptor Binding Domain (Antigenic or C-terminal portion) of Toxin B 10463 in *E. coli* BL 21 cells.

The purification of native toxin B from *C. difficile* involves highly specialized techniques that require extensive training and expensive equipment. Prior to the claimed invention, expression of this recombinant toxin B was extremely difficult using standard *E. coli* systems. For instance, while specific regions of Toxin B have been cloned and purified using *E. coli*, only small amounts were obtained due to the inherent complications of purifying *C. difficile* proteins using *E. coli*. The present invention has enabled improved expression and purification of toxin B and its antigenic region using bacterial host cells (such as *E. coli*). Various aspects of the present invention provide faster, easier expression and purification of toxin B using readily available, standard techniques.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. An isolated nucleotide sequence encoding *Clostridium difficile* toxin B, wherein said isolated nucleotide sequence has been optimized for improved expression of said toxin B in a bacterial cell; and wherein said isolated nucleotide sequence comprises at least one of SEQ ID NOS. 1, 5, 6 and 11.

2. The isolated nucleotide sequence of claim 1, wherein said isolated nucleotide sequence is flanked by restriction enzyme sites.

3. The isolated nucleotide sequence of claim 1, wherein said isolated nucleotide sequence is in an expression vector.

4. The isolated nucleotide sequence of claim 1, wherein said bacterial cell is *Escherichia coli.*

5. An isolated nucleotide sequence, wherein said isolated nucleotide sequence is mutagenized to encode an inactive form of *Clostridium difficile* toxin B.

6. The isolated nucleotide sequence of claim 5, wherein said isolated nucleotide sequence comprises at least one of SEQ ID NOS. 7, 8, 9 and 10.

7. An isolated nucleotide sequence encoding a *Clostridium difficile* protein, wherein said isolated nucleotide sequence is optimized for improved expression of the protein in a bacterial cell and is selected from SEQ ID NOS 1, 3, 5, 6, 7, 8, 9, 10 and 11, wherein said optimization comprises the identification of one or more codons that rarely appear in said bacterial cell, and the replacement of said one or more codons with one or more codons that more frequently appear in said bacterial cell.

8. The isolated nucleotide sequence of claim 7, wherein said isolated nucleotide sequence encodes an antigenic portion of toxin B.

9. The isolated nucleotide sequence of claim 7, wherein said isolated nucleotide sequence encodes full length toxin B.

10. The isolated nucleotide sequence of claim 7, wherein said isolated nucleotide sequence is mutagenized to encode an inactive form of *Clostridium difficile* toxin B.

11. A method of expressing recombinant a *Clostridium difficile* protein in a bacterial cell, said method comprising:

optimizing a nucleotide sequence encoding a *Clostridium difficile* toxin B protein, wherein said optimization comprises changing one or more codons in said nucleotide sequence, and wherein said optimization leads to improved protein expression in said bacterial cell;

introducing said nucleotide sequence into said bacterial cell; and inducing an expression of said protein from said nucleotide sequence in said bacterial cell.

12. The method of claim 11, wherein said method further comprises purifying said expressed protein from said bacterial cell.

13. The method of claim 11, wherein said method further comprises mutagenizing said nucleotide sequence to encode an inactive form of *Clostridium difficile* toxin B.

14. The method of claim 11, wherein said optimization further comprises:

the identification of one or more codons in said nucleotide sequence that rarely appear in said bacterial cell; and the replacement of said one or more codons with one or more codons that more frequently appear in said bacterial cell.

15. The method of claim 11, wherein said optimized nucleotide sequence is inserted into an IPTG-inducible expression vector before said introduction into said bacterial cell.

16. The method of claim 15, wherein said induction comprises exposure of said bacterial cell to IPTG.

17. The method of claim 11, wherein said bacterial cell is *Escherichia coli.*

18. A bacterial cell comprising an isolated nucleotide sequence encoding a *Clostridium difficile* protein, wherein said isolated nucleotide sequence has been optimized for improved expression of protein in said bacterial cell; and wherein said isolated nucleotide sequence comprises at least one of SEQ ID NOS.1, 3, 5, 6, 7, 8, 9, 10 and 11.

19. The bacterial cell of claim 18, wherein said bacterial cell is *Escherichia coli.*

20. The bacterial cell of claim 18, wherein said isolated nucleotide sequence in said bacterial cell has been mutagenized to encode an inactive form of *Clostridium difficile* toxin B.

21. A bacterial cell comprising an isolated nucleotide sequence encoding a *Clostridium difficile* protein, wherein said isolated nucleotide sequence has been optimized for improved expression of protein in said bacterial cell, and is selected from SEQ ID NOS 1, 3, 5, 6, 7, 8, 9, 10 and 11, wherein said optimization comprises the identification of one or more codons that rarely appear in said bacterial cell, and the replacement of said one or more codons with one or more codons that more frequently appear in said bacterial cell.

22. The bacterial cell of claim 21, wherein said isolated nucleotide sequence in said bacterial cell has been mutagenized to encode an inactive form of *Clostridium difficile* toxin B.

23. An isolated peptide derived from recombinant *Clostridium difficile* protein, wherein said isolated peptide sequence comprises at least one of SEQ ID NOS. 12, 13, 16 and 17.

* * * * *

SEQUENCE LISTING

```
<160> NUMBER OF SEQ ID NOS: 17

<210> SEQ ID NO 1
<211> LENGTH: 7101
<212> TYPE: DNA
<213> ORGANISM: Clostridium difficile
<220> FEATURE:
<221> NAME/KEY: gene
<222> LOCATION: (1)..(7101)

<400> SEQUENCE: 1

atgagcctgg tgaaccgtaa acagctggaa aaaatggcga atgtgcgttt tcgcgttcag      60

gaagatgaat acgttgcgat tctggatgcc ctggaagaat atcataacat gagcgaaaat     120

accgtggttg aaaaatacct gaaactgaaa gatatcaaca gtctgaccga tatctacatc     180

gatacgtaca aaaaatctgg ccgcaacaaa gccctgaaaa aattcaaaga atacctggtg     240

accgaagttc tggaactgaa aaacaataac ctgacgccgg tggagaaaaa cctgcacttt     300

gtttggatcg gcggtcagat caacgatacc gcaatcaatt acatcaacca gtggaaagat     360

gtgaactctg attacaacgt gaacgtgttt tatgatagta atgcgttcct gattaacacc     420

ctgaagaaaa ccatcgttga aagcgccacg aacgataccc tggaatcttt ccgtgaaaac     480

ctgaatgatc cgcgcttcga ttacaacaaa ttctaccgta aacgcatgga aatcatctac     540

gataaacaga aaaacttcat caactactac aaaacccagc gtgaagaaaa cccggatctg     600

atcatcgatg atatcgtgaa aatctacctg agtaacgaat acagcaaaga tatcgatgaa     660

ctgaacagct atatcgaaga atctctgaat aaagtgaccg aaaactctgg caatgatgtt     720

cgcaactttg aagaattcaa aggcggtgaa agttttaaac tgtacgaaca ggaactggtg     780

gaacgttgga atctggcggc cgcaagtgat atcctgcgca ttagcgcgct gaaagaagtg     840

ggcggtgttt atctggatgt tgatatgctg ccgggtattc agccggatct gttcgaaagc     900

atcgaaaaac cgagctctgt gaccgttgat ttttgggaaa tggtgaaact ggaagcaatc     960

atgaaataca aagaatacat cccgggctat acgagcgaac acttcgatat gctggatgaa    1020
```

-continued

```
gaagtgcaga gtagctttga atctgttctg gcgagtaaaa gcgataaaag tgaaattttc   1080
tctagtctgg gtgatatgga agcgagcccg ctggaagtta aaatcgcctt caactctaaa   1140
ggcatcatca accagggtct gatcagtgtg aaagattctt actgcagtaa cctgatcgtt   1200
aaacagatcg aaaaccgtta caaaatcctg aataactctc tgaacccggc cattagtgaa   1260
gataacgatt ttaataccac gaccaatgca ttcatcgata gcattatggc cgaagcaaac   1320
gcggataatg gccgttttat gatggaactg ggtaaatatc tgcgcgtggg ctttttcccg   1380
gatgttaaaa cgaccattaa cctgagcggt ccggaagcgt acgcggcagc atatcaggat   1440
ctgctgatgt tcaaagaagg cagtatgaat atccacctga ttgaagcgga tctgcgtaac   1500
ttcgaaatca gcaaaaccaa catctctcag agtacggaac aggaaatggc cagcctgtgg   1560
tctttcgatg atgcccgcgc aaaagcgcag ttcgaagaat acaagaaaaa ctacttcgaa   1620
ggcagcctgg gtgaagatga taatctggat ttttctcaga acaccgtggt tgataaagaa   1680
tacctgctgg aaaaaatcag ctctctggcg cgtagtagcg aacgcggtta catccattat   1740
attgtgcagc tgcagggcga taaaatcagc tacgaagcgg cctgcaatct gtttgcaaaa   1800
accccgtatg atagtgttct gttccagaaa aacattgaag atagcgaaat cgcgtattac   1860
tataatccgg gcgatggtga aatccaggaa atcgataaat acaaaatccc gagtatcatc   1920
agcgatcgcc cgaaaattaa actgaccttt atcggccacg gtaaagatga atttaacacg   1980
gatattttcg cgggcctgga tgtggatagc ctgtctaccg aaatcgaaac ggcaattgat   2040
ctggcgaaag aagatatctc tccgaaaagt atcgaaatca atctgctggg ttgtaacatg   2100
tttagttaca gcgtgaatgt tgaagaaacc tatccgggca aactgctgct gcgtgtgaaa   2160
gataaagttt ctgaactgat gccgtctatc agtcaggatt ctattatcgt gagtgccaat   2220
cagtatgaag ttcgcattaa cagcgaaggt cgtcgcgaac tgctggatca tagcggcgaa   2280
tggatcaaca aagaagaatc tatcatcaaa gatatctcta gtaaagaata catcagcttc   2340
aacccgaaag aaaacaaaat catcgtgaaa agtaaaaacc tgccggaact gagcaccctg   2400
ctgcaggaaa tccgtaataa cagcaatagc tctgatattg aactggaaga aaaagtgatg   2460
ctggcagaat gcgaaatcaa cgttatctct aacatcgata cccaggtggt tgaaggtcgc   2520
attgaagaag cgaaaagtct gacgagcgat tctatcaact acatcaaaaa cgaattcaaa   2580
ctgattgaaa gtatcagcga tgcgctgtat gatctgaaac agcagaacga actggaagaa   2640
agccacttta tttctttcga agatatcctg gaaaccgatg aaggtttctc tatccgtttc   2700
atcgataaag aaaccggcga aagtattttt gtggaaacgg aaaaagcaat cttcagcgaa   2760
tacgcgaacc atatcaccga agaaatctct aaaatcaaag gtaccatctt tgatacggtg   2820
aacggcaaac tggtgaaaaa agttaatctg gatgccaccc acgaagttaa cacgctgaat   2880
gcagcgtttt tcatccagag cctgattgaa tacaacagta gcaaagaatc tctgagtaat   2940
ctgagcgtgg caatgaaagt gcaggtttat gcgcagctgt tttctaccgg cctgaacacg   3000
attaccgatg ccgcaaaagt ggttgaactg gttagcaccg ccctggatga aacgattgat   3060
ctgctgccga ccctgagcga aggtctgccg gtgatcgcaa cgattatcga tggcgtttct   3120
ctgggtgcgg ccattaaaga actgagcgaa acctctgatc cgctgctgcg tcaggaaatt   3180
gaagccaaaa ttggcatcat ggcagtgaat ctgaccgcag cgacgaccgc aattatcacg   3240
tctagtctgg gcattgcgag tggttttagc atcctgctgg tgccgctggc aggtatcagt   3300
gcaggtattc cgagcctggt taataacgaa ctgatcctgc gcgataaagc gaccaaagtg   3360
gttgattact tctctcatat cagtctggcg gaaagcgaag gtgcctttac gtctctggat   3420
```

-continued

```
gataaaatta tgatgccgca ggatgatctg gtgatcagtg aaatcgattt caacaacaac   3480
agcattaccc tgggtaaatg tgaaatctgg cgtatggaag gcggtagcgg ccatacggtt   3540
accgatgata tcgatcactt tttcagcgcc ccgtctatta cctaccgcga accgcacctg   3600
agcatctatg atgtgctgga agttcagaaa gaagaactgg atctgtctaa agatctgatg   3660
gtgctgccga acgcgccgaa tcgtgttttc gcctgggaaa cgggttggac cccgggtctg   3720
cgtagcctgg aaaacgatgg taccaaactg ctggatcgta ttcgcgataa ttacgaaggc   3780
gaattttact ggcgttattt tgcgttcatt gccgatgcac tgatcacgac cctgaaaccg   3840
cgttatgaag ataccaacat tcgcatcaat ctggatagta acacgcgtag cttcatcgtg   3900
ccggttatta cgaccgaata tattcgcgaa aaactgagct actcttttta tggcagcggc   3960
ggtacctacg ccctgagtct gagccagtac aacatgaaca tcaacatcga actgaacgaa   4020
aacgatacct gggtgattga tgttgataac gtggttcgcg atgtgacgat cgaaagcgat   4080
aaaatcaaaa aaggtgatct gatcgaaaac atcctgagta aactgagcat cgaagataac   4140
aaaatcatcc tggataacca tgaaatcaac tttagcggta ccctgaacgg cggtaatggc   4200
tttgtttctc tgacgttcag tatcctggaa ggtattaatg cggtgatcga agttgatctg   4260
ctgtctaaaa gttataaagt gctgattagc ggcgaactga aaaccctgat ggccaatagc   4320
aactctgttc agcagaaaat tgattacatc ggtctgaata gtgaactgca gaaaaacatc   4380
ccgtatagct ttatggatga taaaggcaaa gaaaacggtt tcatcaactg cagcaccaaa   4440
gaaggcctgt ttgtgtctga actgagtgat gtggttctga tctctaaagt ttacatggat   4500
aacagtaaac cgctgtttgg ctattgtagc aatgatctga aagatgtgaa agttatcacc   4560
aaagatgatg tgatcatcct gacgggttac tacctgaaag atgatatcaa aatcagtctg   4620
agcttcacca ttcaggatga aaatacgatc aaactgaacg gtgtgtatct ggatgaaaac   4680
ggcgttgcgg aaatcctgaa attcatgaac aaaaaaggca gcacgaacac ctctgatagt   4740
ctgatgagct tcctggaatc tatgaacatc aaatctatct tcatcaatag cctgcagtct   4800
aacaccaaac tgatcctgga tacgaatttc atcatcagtg gcacgaccag cattggccag   4860
ttcgaattca tctgcgataa agataacaac atccagccgt acttcatcaa attcaacacg   4920
ctggaaacca aatacacgct gtatgtgggt aaccgtcaga atatgattgt tgaaccgaac   4980
tatgatctgg atgatagtgg tgatattagc tctaccgtga tcaattttag ccagaaatac   5040
ctgtatggca tcgattcttg tgtgaacaaa gttatcatca gtccgaacat ctacaccgat   5100
gaaatcaaca tcacgccgat ctacgaagcg aacaatacct atccggaagt gattgttctg   5160
gatacgaact acatctctga aaaaatcaac atcaacatca acgatctgag tattcgttat   5220
gtgtggtcta acgatggcag tgattttatc ctgatgagca ccgatgaaga aaacaaagtg   5280
tctcaggtta aaatccgctt caccaacgtt ttcaagggta acacgatcag cgataaaatc   5340
tctttcaact tcagtgataa acaggatgtg agcatcaaca aagttatctc tacgttcacc   5400
ccgagttact atgtggaagg tctgctgaac tacgatctgg gcctgattag cctgtacaac   5460
gaaaaattct acatcaacaa cttcggcatg atggtgtctg gtctggttta catcaacgat   5520
agcctgtact acttcaaacc gccgattaaa aatctgatca ccggcttcac gaccatcggt   5580
gatgataaat actacttcaa cccggataat ggcggtgccg caagcgtggg tgaaaccatc   5640
atcgatggca aaaactacta cttcagccag aacggcgtgc tgcagaccgg tgtgtttagc   5700
acggaagatg gctttaaata tttcgcgccg gccgataccc tggatgaaaa tctggaaggt   5760
gaagcgatcg atttcaccgg caaactgacg attgatgaaa acgtgtacta cttcggtgat   5820
```

-continued aactatcgtg cggccattga atggcagacc ctggatgatg aagtttacta cttctctacg 5880
gataccggcc gcgccttcaa aggtctgaac cagatcggcg atgataaatt ctacttcaac 5940
agcgatggta tcatgcagaa aggcttcgtg aacatcaacg ataaaacctt ctacttcgat 6000
gatagcggtg ttatgaaatc tggctatacg gaaatcgatg gcaaatactt ttatttcgcg 6060
gaaaacggtg aaatgcagat tggcgtgttt aataccgccg atggttttaa atacttcgca 6120
catcacgatg aagatctggg caacgaagaa ggtgaagccc tgagctactc tggcattctg 6180
aacttcaaca acaaaatcta ctacttcgat gatagtttca ccgcagtggt tggttggaaa 6240
gatctggaag atggcagcaa atactatttt gatgaagata cggcagaagc gtatatcggt 6300
atctctatca tcaacgatgg caaatactac ttcaacgata gtggtatcat gcagatcggc 6360
ttcgtgacca tcaacaacga agtgttttat ttcagtgata gcggtatcgt ggaaagcggc 6420
atgcagaaca tcgatgacaa ctacttctac atcgatgaaa acggtctggt gcagattggc 6480
gttttcgata cctctgatgg ttacaaatac ttcgccccgg caaatacggt gaacgataat 6540
atctacggcc aggcagttga atatagcggt ctggtgcgtg ttggcgaaga tgtgtactat 6600
tttggtgaaa cgtacaccat tgaaaccggc tggatctatg atatggaaaa cgaaagcgat 6660
aaatactact tcgatccgga aacgaaaaaa gcgtacaaag gcatcaacgt tatcgatgat 6720
atcaaatact acttcgatga aaacggtatt atgcgcaccg gcctgatcac gttcgaagat 6780
aaccattact acttcaacga agatggtatc atgcagtacg gctacctgaa catcgaagac 6840
aaaacgttct acttctctga agacggtatc atgcagattg gcgtgttcaa taccccggat 6900
ggttttaaat atttcgccca ccagaatacg ctggatgaaa acttcgaagg tgaaagcatc 6960
aactacaccg gctggctgga tctggatgaa aaacgctact atttcaccga tgaatatatc 7020
gcagcgacgg gtagtgtgat tatcgatggc gaagaatact attttgatcc ggataccgca 7080
cagctggtta ttagcgaata a 7101

<210> SEQ ID NO 2
<211> LENGTH: 7101
<212> TYPE: DNA
<213> ORGANISM: Clostridium difficile
<220> FEATURE:
<221> NAME/KEY: gene
<222> LOCATION: (1)..(7101)

<400> SEQUENCE: 2
atgagtttag ttaatagaaa acagttagaa aaaatggcaa atgtaagatt tcgtgttcag 60
gaagatgaat atgtagcaat attggatgct ttagaagaat atcataatat gtcagagaat 120
actgtagtcg aaaaatattt aaaattaaaa gatataaata gtttaacaga tatttatata 180
gatacatata aaaagtctgg tagaaataaa gccttaaaaa aatttaagga atacctagtt 240
acagaagtat tagagctaaa gaataataat ttaactccag ttgagaaaaa tttacatttt 300
gtttggattg gaggtcaaat aaatgacact gctattaatt atataaatca atggaaagat 360
gtaaatagtg attataatgt taatgttttt tatgatagta atgcattttt gataaacaca 420
ttgaaaaaaa ctatagtaga atcagcaaca aatgatacac ttgaatcatt tagagaaaac 480
ttaaatgacc ctagatttga ctataataaa ttttacagaa aacgtatgga gataatctat 540
gataagcaga aaaatttcat aaattactat aaaactcaaa gagaagaaaa tcctgacctt 600
ataattgatg atattgtaaa gatatatctt tcaaacgagt attcaaagga tatagatgaa 660
cttaattcct atattgaaga gtcattaaat aaagttacag aaaatagtgg gaatgatgtt 720
agaaactttg aagaatttaa aggtggagag tcattcaaat tatatgaaca agagttggta 780

-continued

```
gaaagatgga atttggcagc tgcttctgac atattaagaa tatctgcctt aaaagaagtt    840
ggtggtgtat atttagatgt tgatatgtta ccaggaatac aaccagacct atttgagtct    900
atagagaaac ctagttcagt aacagtggat ttttgggaaa tggtaaaatt agaagctata    960
atgaaataca aagaatacat accaggatat acttcagagc attttgatat gttggatgaa   1020
gaagttcaaa gtagttttga atctgttcta gcttctaagt cagataagtc agaaatattc   1080
tcatcacttg gcgatatgga ggcatcacca ctagaagtta aaattgcatt taatagtaaa   1140
ggtattataa atcaaggact aatttctgtg aaagactcat attgtagcaa tttaatagta   1200
aaacaaatcg agaacagata taagatattg aataatagtt taaatccagc tattagcgag   1260
gataacgatt tcaatactac aacgaatgct tttattgata gtataatggc tgaagctaat   1320
gcagataatg gtagatttat gatggaacta ggaaagtatt taagagttgg tttcttccca   1380
gatgttaaaa ctactattaa cttaagtggc cctgaagcat atgcggcagc ttatcaagat   1440
ttattaatgt ttaaagaagg tagtatgaat atccatttga tagaagctga cttaagaaac   1500
tttgaaatct ctaaaactaa tatttctcaa tcaactgaac aagaaatggc tagcttatgg   1560
tcatttgacg atgcaagagc taaagctcaa tttgaagaat acaaaaaaaa ttactttgaa   1620
ggttctcttg gagaagatga caatcttgac ttttctcaaa atacagtagt tgacaaggag   1680
tatcttttag aaaaaatatc ttcattagca agaagttcag agagaggata tatacactat   1740
attgttcagt tacaaggaga taaaattagt tatgaagcag catgtaactt atttgcaaag   1800
actccttatg atagtgtact gtttcagaaa aatatagaag attcagaaat tgcatattat   1860
tataatcctg gagatggtga aatacaagaa atagacaagt ataaaattcc aagtataatt   1920
tctgatagac ctaagattaa attaacattt attggtcatg gtaaagatga atttaatact   1980
gatatatttg caggtcttga tgtagattca ttatccacag aaatagaaac agcaatagat   2040
ttagctaaag aggatatttc tcctaagtca atagaaataa acttactggg atgtaacatg   2100
tttagctatt ctgtaaatgt agaggagact tatcctggga aattattact tagagttaaa   2160
gataaagtat cagaattaat gccatctata agtcaagact ctattatagt aagtgcaaat   2220
caatatgaag ttagaataaa tagtgaagga agaagagaat tattggatca ttctggtgaa   2280
tggataaata aagaagaaag tattataaag gatatttcat caaaagaata tatatcattt   2340
aatcctaaag aaaataaaat tatagtaaaa tctaaaaatt tacctgaatt atctacatta   2400
ttacaagaaa ttagaaacaa ttctaattca agtgatattg aactagaaga aaaagtaatg   2460
ttagcagaat gtgagataaa tgttatttca aatatagata cacaagtggt agaaggaagg   2520
attgaagaag ctaaaagctt aacttctgac tctattaatt atataaagaa tgaatttaaa   2580
ctaatagaat ctatttctga tgcactatac gatttaaaac aacagaatga attagaagag   2640
tctcatttta tatcttttga ggatatattg gagactgatg aaggctttag tataagattt   2700
attgataaag aaactggaga atctatattt gtagaaactg aaaaggcaat attctctgaa   2760
tatgctaatc atataactga agagatttct aagataaaag gtactatatt tgatactgta   2820
aatggtaagt tagtaaaaaa agtaaattta gatgctacac atgaagtgaa tactttaaat   2880
gctgcatttt ttatacaatc attaatagaa tataatagtt ctaaagaatc tcttagtaat   2940
ttaagtgtag caatgaaagt tcaagtttat gctcaattat ttagtactgg tttaaatact   3000
attacagatg cagccaaagt tgttgaatta gtatcaactg cattagatga aactatagat   3060
ttacttccta cattatctga aggattacct gtaattgcaa ctatcataga tggtgtaagt   3120
ttaggtgcag caatcaaaga gctaagtgaa acaagtgacc cattattaag acaagaaata   3180
```

-continued gaagctaaga taggtataat ggcagtaaat ttaacagcag ctacaactgc aatcattact 3240
tcatctttag gaatagctag tggatttagt atacttttag ttcctttagc aggaatttca 3300
gcaggtatac caagtttagt aaacaatgag cttatcctaa gagataaagc aacaaaagtt 3360
gtagattatt ttagtcatat atcattagct gagtctgaag gagcatttac ttcattagat 3420
gataaaataa tgatgccaca agatgattta gtaatatctg agatagactt taataacaat 3480
tcaataactt taggtaaatg tgaaatctgg agaatggaag gtggctcagg tcatactgta 3540
actgatgata tagatcactt cttttcagca ccatcaataa catatagaga gccacactta 3600
tctatatatg acgtattgga agtacaaaaa gaagaacttg atttgtcaaa agatttaatg 3660
gtattaccta atgctccaaa tagagtattt gcttgggaaa caggatggac accaggttta 3720
agaagcttag aaaatgatgg cacaaaactg ttagaccgta taagagataa ctatgaaggt 3780
gagttttatt ggagatattt tgcttttata gctgatgctt taataacaac attaaaacca 3840
agatatgaag atactaatat aagaataaat ttagatagta atactagaag ctttatagtc 3900
ccagtgataa ctacagaata tataagagag aaattatcat attcttttta tggttctgga 3960
ggaacttatg cattatctct ttctcaatac aatatgaata taaacataga attaaatgaa 4020
aatgatactt gggttataga tgtcgacaat gtcgtaagag atgtcactat agaatctgat 4080
aaaattaaaa aaggagattt aatagagaat attttatcta aattaagtat tgaagacaat 4140
aaaattattt tagataatca tgaaattaat ttctctggaa cattaaatgg aggtaatgga 4200
tttgtatctt taacattctc aatcttagaa ggaataaatg cagttataga agttgattta 4260
ttatctaaat catataaagt tcttatttct ggtgaactaa aacattgat ggcaaattca 4320 aattctgttc aacagaaaat agattatata ggattgaaca gcgaattaca aaaaaatata 4380
ccttatagtt ttatggatga taaaggaaaa gaaaatggat ttattaattg ttctacaaaa 4440
gaaggtttat ttgtatctga attatctgat gtagttctta taagtaaagt ttatatggac 4500
aatagtaaac ctctatttgg atattgtagt aatgatttga aagatgttaa agtcataact 4560
aaagatgacg ttattatatt aacaggatat tatttaaaag atgatataaa aatctctctt 4620
tcttttacta tacaagatga aaatactata aaattaaatg gagtatattt agatgaaaat 4680
ggagtagctg aaatattgaa atttatgaat aaaaaaggta gtacaaatac ttcagattct 4740
ttaatgagct ttttagaaag tatgaatata aaaagtattt tcataaattc cttacaatct 4800
aatactaagc ttatattaga tactaatttt ataataagtg gtactacttc tattggtcaa 4860
tttgagttta tttgtgataa agataataat atacaaccat atttcattaa gtttaataca 4920
ctagaaacta aatatactct atatgtaggt aatagacaaa atatgatagt agaaccaaat 4980
tatgatttag atgattctgg agatatatct tcaactgtca ttaatttttc tcagaaatac 5040
ctttatggaa tagacagttg tgttaataaa gttataattt cgccaaatat atatacagat 5100
gaaataaaca taacacctat atatgaagca aataatactt atccagaagt gattgtatta 5160
gatacaaatt atataagtga aaaaatcaat attaatatca atgatttatc tatacgatat 5220
gtatggagta atgatggaag tgattttatt cttatgtcaa ctgatgaaga gaacaaggta 5280
tcacaagtta aaataagatt tactaatgtt tttaaaggta atactatatc agataagata 5340
tcttttaatt ttagtgataa gcaagatgta tctataaata aagttatttc aacatttaca 5400
ccttcatatt atgtggaagg attacttaat tatgatttag gtctgatttc tttatacaat 5460
gagaaatttt atattaataa ctttggaatg atggtgtctg gattagtata tattaatgat 5520
tcattatatt atttcaagcc accaataaag aacttgataa ctggatttac aactataggt 5580

-continued

```
gatgataaat actactttaa tccagataat ggtggagctg cttcagtcgg agaaacaata   5640

attgatggca aaaactacta cttcagccaa aatggagtgt tacaaacagg tgtatttagt   5700

acagaagatg gatttaaata ttttgctcca gcagatacac ttgatgaaaa tctagagggg   5760

gaagcaattg attttactgg caaactaact attgatgaaa atgtttatta ttttggagat   5820

aattatagag cagctataga atggcaaaca ttagatgatg aagtgtacta ttttagtaca   5880

gatacaggta gagcttttaa agggctaaat caaataggtg atgataaatt ctatttcaac   5940

tctgatggta ttatgcaaaa aggatttgtt aatataaatg ataagacatt ctattttgat   6000

gattctggtg tgatgaagtc aggatatact gaaatagatg gaaaatattt ttactttgct   6060

gagaatggag aaatgcaaat aggagtattt aatacagcag atggatttaa atattttgct   6120

catcatgatg aagatttagg aaatgaagaa ggtgaagcac tttcatattc tggtatactt   6180

aattttaaca ataagattta ttattttgat gattcattta cagcagtagt tggatggaag   6240

gatttagaag atggttcaaa atattacttt gatgaagata cagcagaagc atatataggt   6300

atctcaataa ttaatgatgg taaatattat tttaatgatt ctggaatcat gcaaattgga   6360

tttgtcacaa taaataatga agtattttat ttctctgatt ctggaatagt agaatctgga   6420

atgcaaaata tagatgataa ttatttctat atagacgaaa atggtctagt tcaaattggt   6480

gtatttgaca cttcagatgg atataaatac tttgcaccag ctaatactgt aaatgataat   6540

atctatggac aagcagttga atatagtggt ttagttagag ttggtgaaga tgtatattat   6600

tttggagaaa catatacaat tgagactggt tggatatatg atatggaaaa tgaaagtgat   6660

aaatattatt tcgatccaga aactaaaaaa gcatataaag gtattaatgt aattgatgat   6720

ataaaatact attttgatga gaatggaata atgagaacag gtcttataac atttgaagat   6780

aatcattact attttaatga agatggtatt atgcaatatg gttatctaaa tatagaagat   6840

aagacgttct actttagtga agatggtatt atgcagattg gagtatttaa tacaccagat   6900

ggatttaaat attttgcaca tcaaaatact ttagatgaga attttgaggg agaatcaata   6960

aactatactg gttggttaga tttagatgaa aagagatatt attttacaga tgaatatatt   7020

gcagcaactg gttcagttat tattgatggt gaggagtatt attttgatcc tgatacagct   7080

caattagtga ttagtgaata g                                              7101
```

<210> SEQ ID NO 3
<211> LENGTH: 2166
<212> TYPE: DNA
<213> ORGANISM: Clostridium difficile
<220> FEATURE:
<221> NAME/KEY: gene
<222> LOCATION: (1)..(2166)

<400> SEQUENCE: 3

```
atgctgtatg tgggtaaccg tcagaatatg attgttgaac cgaactatga tctggatgat     60

agtggtgata ttagctctac cgtgatcaat tttagccaga aatacctgta tggcatcgat    120

tcttgtgtga acaaagttat catcagtccg aacatctaca ccgatgaaat caacatcacg    180

ccgatctacg aagcgaacaa tacctatccg gaagtgattg ttctggatac gaactacatc    240

tctgaaaaaa tcaacatcaa catcaacgat ctgagtattc gttatgtgtg gtctaacgat    300

ggcagtgatt ttatcctgat gagcaccgat gaagaaaaca aagtgtctca ggttaaaatc    360

cgcttcacca acgttttcaa gggtaacacg atcagcgata aaatctcttt caacttcagt    420

gataaacagg atgtgagcat caacaaagtt atctctacgt tcaccccgag ttactatgtg    480
```

-continued

```
gaaggtctgc tgaactacga tctgggcctg attagcctgt acaacgaaaa attctacatc    540

aacaacttcg gcatgatggt gtctggtctg gtttacatca acgatagcct gtactacttc    600

aaaccgccga ttaaaaatct gatcaccggc ttcacgacca tcggtgatga taaatactac    660

ttcaacccgg ataatggcgg tgccgcaagc gtgggtgaaa ccatcatcga tggcaaaaac    720

tactacttca gccagaacgg cgtgctgcag accggtgtgt ttagcacgga agatggcttt    780

aaatatttcg cgccggccga taccctggat gaaaatctgg aaggtgaagc gatcgatttc    840

accggcaaac tgacgattga tgaaaacgtg tactacttcg gtgataacta tcgtgcggcc    900

attgaatggc agaccctgga tgatgaagtt tactacttct ctacggatac cggccgcgcc    960

ttcaaaggtc tgaaccagat cggcgatgat aaattctact tcaacagcga tggtatcatg   1020

cagaaaggct tcgtgaacat caacgataaa accttctact tcgatgatag cggtgttatg   1080

aaatctggct atacggaaat cgatggcaaa tacttttatt tcgcggaaaa cggtgaaatg   1140

cagattggcg tgtttaatac cgccgatggt tttaaatact tcgcacatca cgatgaagat   1200

ctgggcaacg aagaaggtga agccctgagc tactctggca ttctgaactt caacaacaaa   1260

atctactact tcgatgatag tttcaccgca gtggttggtt ggaaagatct ggaagatggc   1320

agcaaatact attttgatga agatacggca gaagcgtata tcggtatctc tatcatcaac   1380

gatggcaaat actacttcaa cgatagtggt atcatgcaga tcggcttcgt gaccatcaac   1440

aacgaagtgt tttatttcag tgatagcggt atcgtggaaa gcggcatgca gaacatcgat   1500

gacaactact tctacatcga tgaaaacggt ctggtgcaga ttggcgtttt cgatacctct   1560

gatggttaca aatacttcgc cccggcaaat acggtgaacg ataatatcta cggccaggca   1620

gttgaatata gcggtctggt gcgtgttggc gaagatgtgt actattttgg tgaaacgtac   1680

accattgaaa ccggctggat ctatgatatg gaaaacgaaa gcgataaata ctacttcgat   1740

ccggaaacga aaaaagcgta caaaggcatc aacgttatcg atgatatcaa atactacttc   1800

gatgaaaacg gtattatgcg caccggcctg atcacgttcg aagataacca ttactacttc   1860

aacgaagatg gtatcatgca gtacggctac ctgaacatcg aagacaaaac gttctacttc   1920

tctgaagacg gtatcatgca gattggcgtg ttcaataccc cggatggttt taaatatttc   1980

gcccaccaga atacgctgga tgaaaacttc gaaggtgaaa gcatcaacta caccggctgg   2040

ctggatctgg atgaaaaacg ctactatttc accgatgaat atatcgcagc gacgggtagt   2100

gtgattatcg atggcgaaga atactatttt gatccggata ccgcacagct ggttattagc   2160

gaataa                                                              2166
```

<210> SEQ ID NO 4
<211> LENGTH: 2166
<212> TYPE: DNA
<213> ORGANISM: Clostridium difficile
<220> FEATURE:
<221> NAME/KEY: gene
<222> LOCATION: (1)..(2166)

<400> SEQUENCE: 4

```
actctatatg taggtaatag acaaaatatg atagtagaac caaattatga tttagatgat     60

tctggagata tatcttcaac tgtcattaat ttttctcaga aataccttta tggaatagac    120

agttgtgtta ataaagttat aatttcgcca aatatatata cagatgaaat aaacataaca    180

cctatatatg aagcaaataa tacttatcca gaagtgattg tattagatac aaattatata    240

agtgaaaaaa tcaatattaa tatcaatgat ttatctatac gatatgtatg gagtaatgat    300

ggaagtgatt ttattcttat gtcaactgat gaagagaaca aggtatcaca agttaaaata    360
```

-continued agatttacta atgtttttaa aggtaatact atatcagata agatatcttt taattttagt 420
gataagcaag atgtatctat aaataaagtt atttcaacat ttacaccttc atattatgtg 480
gaaggattac ttaattatga tttaggtctg atttctttat acaatgagaa attttatatt 540
aataactttg gaatgatggt gtctggatta gtatatatta atgattcatt atattatttc 600
aagccaccaa taaagaactt gataactgga tttacaacta taggtgatga taaatactac 660
tttaatccag ataatggtgg agctgcttca gtcggagaaa caataattga tggcaaaaac 720
tactacttca gccaaaatgg agtgttacaa acaggtgtat ttagtacaga agatggattt 780
aaatattttg ctccagcaga tacacttgat gaaaatctag agggggaagc aattgatttt 840
actggcaaac taactattga tgaaaatgtt tattattttg gagataatta tagagcagct 900
atagaatggc aaacattaga tgatgaagtg tactatttta gtacagatac aggtagagct 960
tttaaagggc taaatcaaat aggtgatgat aaattctatt tcaactctga tggtattatg 1020
caaaaaggat ttgttaatat aaatgataag acattctatt ttgatgattc tggtgtgatg 1080
aagtcaggat atactgaaat agatggaaaa tatttttact ttgctgagaa tggagaaatg 1140
caaataggag tatttaatac agcagatgga tttaaatatt ttgctcatca tgatgaagat 1200
ttaggaaatg aagaaggtga agcactttca tattctggta tacttaattt taacaataag 1260
atttattatt ttgatgattc atttacagca gtagttggat ggaaggattt agaagatggt 1320
tcaaaatatt actttgatga agatacagca gaagcatata taggtatctc aataattaat 1380
gatggtaaat attattttaa tgattctgga atcatgcaaa ttggatttgt cacaataaat 1440
aatgaagtat tttatttctc tgattctgga atagtagaat ctggaatgca aaatatagat 1500
gataattatt tctatataga cgaaaatggt ctagttcaaa ttggtgtatt tgacacttca 1560
gatggatata aatactttgc accagctaat actgtaaatg ataatatcta tggacaagca 1620
gttgaatata gtggtttagt tagagttggt gaagatgtat attattttgg agaaacatat 1680
acaattgaga ctggttggat atatgatatg gaaaatgaaa gtgataaata ttatttcgat 1740
ccagaaacta aaaaagcata taaaggtatt aatgtaattg atgatataaa atactatttt 1800
gatgagaatg gaataatgag aacaggtctt ataacatttg aagataatca ttactatttt 1860
aatgaagatg gtattatgca atatggttat ctaaatatag aagataagac gttctacttt 1920
agtgaagatg gtattatgca gattggagta tttaatacac cagatggatt taaatatttt 1980
gcacatcaaa atactttaga tgagaatttt gagggagaat caataaacta tactggttgg 2040
ttagatttag atgaaaagag atattatttt acagatgaat atattgcagc aactggttca 2100
gttattattg atggtgagga gtattatttt gatcctgata cagctcaatt agtgattagt 2160
gaatag 2166

<210> SEQ ID NO 5
<211> LENGTH: 7101
<212> TYPE: DNA
<213> ORGANISM: Clostridium difficile
<220> FEATURE:
<221> NAME/KEY: gene
<222> LOCATION: (1)..(7101)

<400> SEQUENCE: 5
atgagcctgg tgaaccgtaa acagctggaa aaaatggcga acgtgcgttt tcgtacccag 60
gaagatgaat atgtggcgat tctggatgcg ctggaagaat atcataacat gagcgaaaac 120
accgtggtgg aaaaatacct gaaactgaaa gatatcaaca gcctgaccga tatctacatc 180

-continued

```
gatacctaca agaaaagcgg ccgtaacaaa gcgctgaaaa aatttaaaga atatctggtg    240
accgaagtgc tggaactgaa aaacaacaac ctgaccccgg tggaaaagaa cctgcatttt    300
gtgtggattg gcggccagat taacgatacc gcgattaact atattaacca gtggaaagat    360
gtgaacagcg attataacgt gaacgtgttt tatgatagca acgcgtttct gattaacacc    420
ctgaagaaaa ccgtggtgga aagcgcgatt aacgataccc tggaaagctt tcgtgaaaac    480
ctgaacgatc cgcgtttcga ttacaacaaa tttttccgta aacgtatgga aatcatctac    540
gataaacaga aaaactttat taactattat aaagcgcagc gtgaagaaaa cccggaactg    600
atcatcgatg atatcgtgaa aacctacctg agcaacgaat acagcaaaga aatcgatgaa    660
ctgaacacct acatcgaaga aagcctgaac aaaatcaccc agaacagcgg caacgatgtg    720
cgtaactttg aagaatttaa aaacggcgaa agctttaacc tgtatgaaca ggaactggtg    780
gaacgttgga acctggcggc ggcgagcgat attctgcgta ttagcgcgct gaaagaaatt    840
ggcggcatgt atctggatgt ggatatgctg ccgggcattc agccggatct gtttgaaagc    900
attgaaaaac cgagcagcgt gaccgtggat ttttgggaaa tgaccaaact ggaagcgatc    960
atgaaataca aagaatacat cccggaatac accagcgaac atttcgatat gctggatgaa   1020
gaagtgcaga gcagctttga aagcgtgctg gcgagcaaaa gcgataaaag cgaaattttt   1080
agcagcctgg gcgatatgga agcgagcccg ctggaagtga aaattgcgtt taacagcaaa   1140
ggcattatta accagggcct gattagcgtg aaagatagct attgcagcaa cctgattgtg   1200
aaacagattg aaaaccgtta taaaattctg aacaacagcc tgaacccggc gattagcgaa   1260
gataacgatt ttaacaccac caccaacacc tttattgata gcattatggc ggaagcgaac   1320
gcggataacg gccgttttat gatggaactg ggcaaatatc tgcgtgtggg tttctttccg   1380
gatgtgaaaa ccaccattaa cctgagcggc ccggaagcgt atgcggcggc gtatcaggat   1440
ctgctgatgt ttaaagaagg cagcatgaac attcatctga ttgaagcgga tctgcgtaac   1500
tttgaaatta gcaaaaccaa cattagccag agcaccgaac aggaaatggc gagcctgtgg   1560
agctttgatg atgcgcgtgc gaaagcgcag tttgaagaat ataaacgtaa ctattttgaa   1620
ggcagcctgg gcgaagatga taacctggat tttagccaga acattgtggt ggataaagaa   1680
tatctgctgg aaaaaattag cagcctggcg cgtagcagcg aacgtggcta tattcattat   1740
attgtgcagc tgcagggcga taaaattagc tatgaagcgg cgtgcaacct gtttgcgaaa   1800
accccgtatg atagcgtgct gtttcagaaa aacattgaag atagcgaaat tgcgtattat   1860
tataacccgg gcgatggcga aatccaggaa atcgataaat acaaaatccc gagcatcatc   1920
agcgatcgtc cgaaaatcaa actgaccttt attggccatg gcaaagatga atttaacacc   1980
gatatttttg cgggctttga tgtggatagc ctgagcaccg aaatcgaagc ggcgattgat   2040
ctggcgaaag aagatattag cccgaaaagc attgaaatta acctgctggg ctgcaacatg   2100
tttagctata gcattaacgt ggaagaaacc tatccgggca aactgctgct gaaagtgaaa   2160
gataaaatta gcgaactgat gccgagcatt agccaggata gcattattgt gagcgcgaac   2220
cagtatgaag tgcgtattaa cagcgaaggc cgtcgtgaac tgctggatca tagcggcgaa   2280
tggatcaaca aagaagaaag catcatcaaa gatatcagca gcaaagaata catcagcttc   2340
aacccgaaag aaaacaaaat caccgtgaaa agcaaaaacc tgccggaact gagcaccctg   2400
ctgcaggaaa ttcgtaacaa cagcaacagc agcgatattg aactggaaga aaaagtgatg   2460
ctgaccgaat gcgaaattaa cgtgattagc aacattgata cccagattgt ggaagaacgt   2520
attgaagaag cgaaaaacct gaccagcgat agcattaact atattaaaga tgaatttaaa   2580
```

-continued

```
ctgattgaaa gcattagcga tgcgctgtgc gatctgaaac agcagaacga actggaagac   2640
agccatttta ttagctttga agatattagc gaaaccgatg aaggctttag cattcgtttt   2700
attaacaaag aaaccggcga aagcattttt gtggaaaccg aaaaaaccat ttttagcgaa   2760
tacgcgaacc atatcaccga agaaatcagc aaaatcaaag gcaccatttt tgataccgtg   2820
aacggcaaac tggtgaaaaa agtgaacctg gataccaccc atgaagtgaa caccctgaac   2880
gcggcatttt tcattcagag cctgattgaa tataacagca gcaaagaaag cctgagcaac   2940
ctgagcgtgg cgatgaaagt gcaggtgtat gcgcagctgt ttagcaccgg cctgaacacc   3000
attaccgacg cggcgaaagt ggtggaactg gttagcaccg cgctggatga aaccattgat   3060
ctgctgccga ccctgagcga aggcctgccg attattgcga ccattattga tggcgtgagc   3120
ctgggcgcgg cgattaaaga actgagcgaa accagcgatc cgctgctgcg tcaggaaatt   3180
gaagcgaaaa ttggcattat ggcggtgaac ctgaccaccg cgaccaccgc gattattacc   3240
agcagcctgg gcattgcgag cggctttagc attctgctgg tgccgctggc gggcattagc   3300
gcgggcattc cgagcctggt gaacaacgaa ctggtgctgc gtgataaagc gaccaaagtg   3360
gtggattatt ttaaacatgt gagcctggtg gaaaccgaag gcgtgtttac cctgctggat   3420
gataaaatta tgatgccgca ggatgatctg gtgattagcg aaattgattt taacaacaac   3480
agcattgtgc tgggcaaatg cgaaatttgg cgtatggaag gcggcagcgg ccataccgtg   3540
accgatgata ttgatcattt ctttagcgcg ccgagcatta cctatcgtga accgcatctg   3600
agcatttatg atgtgctgga agtgcagaaa gaagaactgg atctgagcaa agatctgatg   3660
gtgctgccga acgcaccgaa ccgtgtgttt gcatgggaaa ccggttggac cccgggtctg   3720
cgtagcctgg aaaacgatgg caccaaactg ctggatcgta ttcgtgataa ctatgaaggc   3780
gaattttatt ggcgttattt tgcgtttatt gcggatgcgc tgattaccac cctgaaaccg   3840
cgttatgaag ataccaacat tcgtattaac ctggatagca acacccgtag ctttattgtg   3900
ccgattatta ccaccgaata tattcgtgaa aaactgagct atagctttta tggcagcggc   3960
ggcacctatg cgctgagcct gagccagtat aacatgggca ttaacattga actgagcgaa   4020
agcgatgtgt ggattattga tgtggataac gtggtgcgtg atgtgaccat tgaaagcgat   4080
aaaattaaaa aaggcgatct gattgaaggc attctgagca ccctgagcat tgaagaaaac   4140
aaaattattc tgaacagcca tgaaattaac tttagcggcg aagtgaacgg cagcaacggc   4200
tttgtgagcc tgacctttag cattctggaa ggcattaacg cgattattga agtggatctg   4260
ctgagcaaaa gctataaact gctgattagc ggcgaactga aaattctgat gctgaacagc   4320
aaccatattc agcagaaaat tgattatatt ggctttaaca gcgaactgca gaaaaacatt   4380
ccgtatagct ttgtggatag cgaaggcaaa gaaaacggct ttattaacgg cagcaccaaa   4440
gaaggcctgt ttgtgagcga actgccggat gtggtgctga ttagcaaagt gtatatggat   4500
gatagcaaac cgagctttgg ctattatagc aacaacctga aagatgtgaa agtgattacc   4560
aaagataacg tgaacattct gaccggctat tatctgaaag atgatattaa aattagcctg   4620
agcctgaccc tgcaggatga aaaaaccatt aaactgaaca gcgtgcatct ggatgaaagc   4680
ggcgtggcgg aaattctgaa atttatgaac cgtaaaggca acaccaacac cagcgatagc   4740
ctgatgagct ttctggaaag catgaacatc aaaagcatct tcgtgaactt tctgcagagc   4800
aacatcaaat tcatcctgga tgcgaacttc atcatcagcg gcaccaccag cattggccag   4860
ttcgaattta tttgcgatga aaacgataac atccagccgt acttcatcaa attcaacacc   4920
ctggaaacca actataccct gtatgtgggc aaccgtcaga acatgattgt ggaaccgaac   4980
```

-continued tatgatctgg atgatagcgg cgatattagc agcaccgtga ttaactttag ccagaaatat 5040
ctgtatggca ttgatagctg cgtgaacaaa gtggtgatta gcccgaacat ttataccgat 5100
gaaattaaca ttaccccggt gtatgaaacc aacaacacct atccggaagt gattgtgctg 5160
gatgcgaact atattaacga aaaaattaac gtgaacatta acgatctgag cattcgttat 5220
gtgtggagca acgatggcaa cgattttatt ctgatgagca ccagcgaaga aaacaaagtg 5280
agccaggtga aaattcgttt tgtgaacgtg tttaaagata aaaccctggc gaacaaactg 5340
agctttaact ttagcgataa acaggatgtg cctgtgagcg aaattattct gagctttacc 5400
ccgagctatt atgaagatgg cctgattggc tatgatctgg gcctggttag cctgtataac 5460
gaaaaatttt atattaacaa ctttggcatg atggttagcg gcctgattta tattaacgat 5520
agcctgtatt attttaaacc gccggtgaac aacctgatta ccggctttgt gaccgtgggc 5580
gatgataaat attattttaa cccgattaac ggcggcgcgg cgagcattgg cgaaaccatt 5640
attgatgata aaaactatta ttttaaccag agcggcgtgc tgcagaccgg cgtgtttagc 5700
accgaagatg gctttaaata ttttgcgccg gcgaacaccc tggatgaaaa cctggaaggc 5760
gaagcgatcg atttcaccgg caaactgatc atcgatgaaa acatctacta cttcgatgat 5820
aactaccgtg gcgcggtgga atggaaagaa ctggatggcg aaatgcatta ttttagcccg 5880
gaaaccggca aagcgtttaa aggcctgaac cagattggcg attataaata ttattttaac 5940
agcgatggcg tgatgcagaa aggctttgtg agcattaacg ataacaaaca ttattttgat 6000
gatagcggcg tgatgaaagt gggctatacc gaaattgatg gcaaacattt ttattttgcg 6060
gaaaacggcg aaatgcagat tggcgtgttt aatacggaag acggttttaa atattttgcg 6120
catcataacg aagatctggg caacgaagaa ggcgaagaaa tcagctacag cggcattctg 6180
aactttaaca acaaaattta ttacttcgat gatagcttta ccgcggtggt gggctggaaa 6240
gatctggaag atggcagcaa atattatttt gatgaagata ccgcggaagc gtatattggc 6300
ctgagcctga ttaacgatgg ccagtattat tttaacgatg atggcattat gcaagtgggc 6360
tttgtgacca ttaacgataa agtgttttat tttagcgata gcggcattat tgaaagcggc 6420
gtgcagaaca ttgatgataa ctatttttat attgatgata acggcattgt gcagattggc 6480
gtgtttgata ccagcgatgg ctacaaatac ttcgccccgg cgaacaccgt gaacgataac 6540
atttatggcc aggcggtgga atatagcggc ctggtgcgtg tgggcgaaga tgtgtattat 6600
tttggcgaaa cctataccat tgaaaccggc tggatctacg atatggaaaa cgaaagcgat 6660
aaatactact tcaacccgga aaccaaaaaa gcgtgcaaag gcatcaacct gatcgatgat 6720
atcaaatact acttcgatga aaaaggcatc atgcgtaccg gcctgattag ctttgaaaac 6780
aacaattact acttcaacga aaatggtgaa atgcagttcg gctacatcaa catcgaagat 6840
aaaatgtttt attttggcga agatggcgtg atgcaaatcg gcgtgtttaa caccccggac 6900
ggtttcaaat attttgcgca tcaaaatacc ctggatgaaa actttgaagg cgaaagcatt 6960
aactataccg gctggctgga tctggatgaa aaacgttatt attttaccga tgaatatatt 7020
gcggcgaccg gcagcgtgat tattgatggc gaagaatatt attttgatcc ggataccgcg 7080
cagctggtga ttagcgaata a 7101

<210> SEQ ID NO 6
<211> LENGTH: 2166
<212> TYPE: DNA
<213> ORGANISM: Clostridium difficile
<220> FEATURE:
<221> NAME/KEY: gene
<222> LOCATION: (1)..(2166)

<400> SEQUENCE: 6
atgctgtatg tgggcaaccg tcagaacatg attgtggaac cgaactatga tctggatgat 60
agcggcgata ttagcagcac cgtgattaac tttagccaga aatatctgta tggcattgat 120
agctgcgtga acaaagtggt gattagcccg aacatttata ccgatgaaat taacattacc 180
ccggtgtatg aaaccaacaa cacctatccg gaagtgattg tgctggatgc gaactatatt 240
aacgaaaaaa ttaacgtgaa cattaacgat ctgagcattc gttatgtgtg gagcaacgat 300
ggcaacgatt ttattctgat gagcaccagc gaagaaaaca aagtgagcca ggtgaaaatt 360
cgttttgtga acgtgtttaa agataaaacc ctggcgaaca aactgagctt taactttagc 420
gataaacagg atgtgcctgt gagcgaaatt attctgagct ttaccccgag ctattatgaa 480
gatggcctga ttggctatga tctgggcctg gttagcctgt ataacgaaaa attttatatt 540
aacaactttg gcatgatggt tagcggcctg atttatatta acgatagcct gtattatttt 600
aaaccgccgg tgaacaacct gattaccggc tttgtgaccg tgggcgatga taaatattat 660
tttaacccga ttaacggcgg cgcggcgagc attggcgaaa ccattattga tgataaaaac 720
tattatttta accagagcgg cgtgctgcag accggcgtgt ttagcaccga agatggcttt 780
aaatattttg cgccggcgaa caccctggat gaaaacctgg aaggcgaagc gatcgatttc 840
accggcaaac tgatcatcga tgaaaacatc tactacttcg atgataacta ccgtggcgcg 900
gtggaatgga aagaactgga tggcgaaatg cattatttta gcccggaaac cggcaaagcg 960
tttaaaggcc tgaaccagat tggcgattat aaatattatt ttaacagcga tggcgtgatg 1020
cagaaaggct ttgtgagcat taacgataac aaacattatt ttgatgatag cggcgtgatg 1080
aaagtgggct ataccgaaat tgatggcaaa catttttatt ttgcggaaaa cggcgaaatg 1140
cagattggcg tgtttaatac ggaagacggt tttaaatatt ttgcgcatca taacgaagat 1200
ctgggcaacg aagaaggcga agaaatcagc tacagcggca ttctgaactt taacaacaaa 1260
atttattact tcgatgatag ctttaccgcg gtggtgggct ggaaagatct ggaagatggc 1320
agcaaatatt attttgatga agataccgcg gaagcgtata ttggcctgag cctgattaac 1380
gatggccagt attattttaa cgatgatggc attatgcaag tgggctttgt gaccattaac 1440
gataaagtgt tttattttag cgatagcggc attattgaaa gcggcgtgca gaacattgat 1500
gataactatt tttatattga tgataacggc attgtgcaga ttggcgtgtt tgataccagc 1560
gatggctaca aatacttcgc cccggcgaac accgtgaacg ataacattta tggccaggcg 1620
gtggaatata gcggcctggt gcgtgtgggc gaagatgtgt attattttgg cgaaacctat 1680
accattgaaa ccggctggat ctacgatatg gaaaacgaaa gcgataaata ctacttcaac 1740
ccggaaacca aaaaagcgtg caaaggcatc aacctgatcg atgatatcaa atactacttc 1800
gatgaaaaag gcatcatgcg taccggcctg attagctttg aaaacaacaa ttactacttc 1860
aacgaaaatg gtgaaatgca gttcggctac atcaacatcg aagataaaat gttttatttt 1920
ggcgaagatg gcgtgatgca aatcggcgtg tttaacaccc cggacggttt caaatatttt 1980
gcgcatcaaa ataccctgga tgaaaacttt gaaggcgaaa gcattaacta taccggctgg 2040
ctggatctgg atgaaaaacg ttattatttt accgatgaat atattgcggc gaccggcagc 2100
gtgattattg atggcgaaga atattatttt gatccggata ccgcgcagct ggtgattagc 2160
gaataa 2166

<210> SEQ ID NO 7
<211> LENGTH: 7101

<212> TYPE: DNA
<213> ORGANISM: Clostridium difficile
<220> FEATURE:
<221> NAME/KEY: gene
<222> LOCATION: (1)..(7101)

<400> SEQUENCE: 7
atgagcctgg tgaaccgtaa acagctggaa aaaatggcga acgtgcgttt tcgtacccag 60
gaagatgaat atgtggcgat tctggatgcg ctggaagaat atcataacat gagcgaaaac 120
accgtggtgg aaaaatacct gaaactgaaa gatatcaaca gcctgaccga tatctacatc 180
gatacctaca agaaaagcgg ccgtaacaaa gcgctgaaaa aatttaaaga atatctggtg 240
accgaagtgc tggaactgaa aaacaacaac ctgaccccgg tggaaaagaa cctgcatttt 300
gtggcgattg gcggccagat taacgatacc gcgattaact atattaacca gtggaaagat 360
gtgaacagcg attataacgt gaacgtgttt tatgatagca acgcgtttct gattaacacc 420
ctgaagaaaa ccgtggtgga aagcgcgatt aacgataccc tggaaagctt tcgtgaaaac 480
ctgaacgatc cgcgtttcga ttacaacaaa tttttccgta aacgtatgga aatcatctac 540
gataaacaga aaaactttat taactattat aaagcgcagc gtgaagaaaa cccggaactg 600
atcatcgatg atatcgtgaa aacctacctg agcaacgaat acagcaaaga aatcgatgaa 660
ctgaacacct acatcgaaga aagcctgaac aaaatcaccc agaacagcgg caacgatgtg 720
cgtaactttg aagaatttaa aaacggcgaa agctttaacc tgtatgaaca ggaactggtg 780
gaacgttgga acctggcggc ggcgagcgat attctgcgta ttagcgcgct gaaagaaatt 840
ggcggcatgt atctggatgt ggatatgctg ccgggcattc agccggatct gtttgaaagc 900
attgaaaaac cgagcagcgt gaccgtggat ttttgggaaa tgaccaaact ggaagcgatc 960
atgaaataca aagaatacat cccggaatac accagcgaac atttcgatat gctggatgaa 1020
gaagtgcaga gcagctttga aagcgtgctg gcgagcaaaa gcgataaaag cgaaattttt 1080
agcagcctgg gcgatatgga agcgagcccg ctggaagtga aaattgcgtt taacagcaaa 1140
ggcattatta accagggcct gattagcgtg aaagatagct attgcagcaa cctgattgtg 1200
aaacagattg aaaaccgtta taaaattctg aacaacagcc tgaacccggc gattagcgaa 1260
gataacgatt ttaacaccac caccaacacc tttattgata gcattatggc ggaagcgaac 1320
gcggataacg gccgttttat gatggaactg ggcaaatatc tgcgtgtggg tttctttccg 1380
gatgtgaaaa ccaccattaa cctgagcggc ccggaagcgt atgcggcggc gtatcaggat 1440
ctgctgatgt ttaaagaagg cagcatgaac attcatctga ttgaagcgga tctgcgtaac 1500
tttgaaatta gcaaaaccaa cattagccag agcaccgaac aggaaatggc gagcctgtgg 1560
agctttgatg atgcgcgtgc gaaagcgcag tttgaagaat ataaacgtaa ctattttgaa 1620
ggcagcctgg gcgaagatga taacctggat tttagccaga acattgtggt ggataaagaa 1680
tatctgctgg aaaaaattag cagcctggcg cgtagcagcg aacgtggcta tattcattat 1740
attgtgcagc tgcagggcga taaaattagc tatgaagcgg cgtgcaacct gtttgcgaaa 1800
accccgtatg atagcgtgct gtttcagaaa aacattgaag atagcgaaat tgcgtattat 1860
tataacccgg gcgatggcga aatccaggaa atcgataaat acaaaatccc gagcatcatc 1920
agcgatcgtc cgaaaatcaa actgaccttt attggccatg gcaaagatga atttaacacc 1980
gatatttttg cgggctttga tgtggatagc ctgagcaccg aaatcgaagc ggcgattgat 2040
ctggcgaaag aagatattag cccgaaaagc attgaaatta acctgctggg ctgcaacatg 2100
tttagctata gcattaacgt ggaagaaacc tatccgggca aactgctgct gaaagtgaaa 2160

-continued

```
gataaaatta gcgaactgat gccgagcatt agccaggata gcattattgt gagcgcgaac   2220
cagtatgaag tgcgtattaa cagcgaaggc cgtcgtgaac tgctggatca tagcggcgaa   2280
tggatcaaca aagaagaaag catcatcaaa gatatcagca gcaaagaata catcagcttc   2340
aacccgaaag aaaacaaaat caccgtgaaa agcaaaaacc tgccggaact gagcaccctg   2400
ctgcaggaaa ttcgtaacaa cagcaacagc agcgatattg aactggaaga aaaagtgatg   2460
ctgaccgaat gcgaaattaa cgtgattagc aacattgata cccagattgt ggaagaacgt   2520
attgaagaag cgaaaaacct gaccagcgat agcattaact atattaaaga tgaatttaaa   2580
ctgattgaaa gcattagcga tgcgctgtgc gatctgaaac agcagaacga actggaagac   2640
agccatttta ttagctttga agatattagc gaaaccgatg aaggctttag cattcgtttt   2700
attaacaaag aaaccggcga aagcattttt gtggaaaccg aaaaaaccat ttttagcgaa   2760
tacgcgaacc atatcaccga agaaatcagc aaaatcaaag gcaccatttt tgataccgtg   2820
aacggcaaac tggtgaaaaa agtgaacctg gataccaccc atgaagtgaa caccctgaac   2880
gcggcatttt tcattcagag cctgattgaa tataacagca gcaaagaaag cctgagcaac   2940
ctgagcgtgg cgatgaaagt gcaggtgtat gcgcagctgt ttagcaccgg cctgaacacc   3000
attaccgacg cggcgaaagt ggtggaactg gttagcaccg cgctggatga aaccattgat   3060
ctgctgccga ccctgagcga aggcctgccg attattgcga ccattattga tggcgtgagc   3120
ctgggcgcgg cgattaaaga actgagcgaa accagcgatc cgctgctgcg tcaggaaatt   3180
gaagcgaaaa ttggcattat ggcggtgaac ctgaccaccg cgaccaccgc gattattacc   3240
agcagcctgg gcattgcgag cggctttagc attctgctgg tgccgctggc gggcattagc   3300
gcgggcattc cgagcctggt gaacaacgaa ctggtgctgc gtgataaagc gaccaaagtg   3360
gtggattatt ttaaacatgt gagcctggtg gaaaccgaag gcgtgtttac cctgctggat   3420
gataaaatta tgatgccgca ggatgatctg gtgattagcg aaattgattt taacaacaac   3480
agcattgtgc tgggcaaatg cgaaatttgg cgtatggaag gcggcagcgg ccataccgtg   3540
accgatgata ttgatcattt ctttagcgcg ccgagcatta cctatcgtga accgcatctg   3600
agcatttatg atgtgctgga agtgcagaaa gaagaactgg atctgagcaa agatctgatg   3660
gtgctgccga acgcaccgaa ccgtgtgttt gcatgggaaa ccggttggac cccgggtctg   3720
cgtagcctgg aaaacgatgg caccaaactg ctggatcgta ttcgtgataa ctatgaaggc   3780
gaattttatt ggcgttattt tgcgtttatt gcggatgcgc tgattaccac cctgaaaccg   3840
cgttatgaag ataccaacat tcgtattaac ctggatagca acacccgtag ctttattgtg   3900
ccgattatta ccaccgaata tattcgtgaa aaactgagct atagctttta tggcagcggc   3960
ggcacctatg cgctgagcct gagccagtat aacatgggca ttaacattga actgagcgaa   4020
agcgatgtgt ggattattga tgtggataac gtggtgcgtg atgtgaccat tgaaagcgat   4080
aaaattaaaa aaggcgatct gattgaaggc attctgagca ccctgagcat tgaagaaaac   4140
aaaattattc tgaacagcca tgaaattaac tttagcggcg aagtgaacgg cagcaacggc   4200
tttgtgagcc tgacctttag cattctggaa ggcattaacg cgattattga agtggatctg   4260
ctgagcaaaa gctataaact gctgattagc ggcgaactga aaattctgat gctgaacagc   4320
aaccatattc agcagaaaat tgattatatt ggctttaaca gcgaactgca gaaaaacatt   4380
ccgtatagct ttgtggatag cgaaggcaaa gaaaacggct ttattaacgg cagcaccaaa   4440
gaaggcctgt ttgtgagcga actgccggat gtggtgctga ttagcaaagt gtatatggat   4500
gatagcaaac cgagctttgg ctattatagc aacaacctga aagatgtgaa agtgattacc   4560
```

-continued

```
aaagataacg tgaacattct gaccggctat tatctgaaag atgatattaa aattagcctg   4620
agcctgaccc tgcaggatga aaaaaccatt aaactgaaca gcgtgcatct ggatgaaagc   4680
ggcgtggcgg aaattctgaa atttatgaac cgtaaaggca acaccaacac cagcgatagc   4740
ctgatgagct ttctggaaag catgaacatc aaaagcatct tcgtgaactt tctgcagagc   4800
aacatcaaat tcatcctgga tgcgaacttc atcatcagcg gcaccaccag cattggccag   4860
ttcgaattta tttgcgatga aaacgataac atccagccgt acttcatcaa attcaacacc   4920
ctggaaacca actatacccct gtatgtgggc aaccgtcaga acatgattgt ggaaccgaac   4980
tatgatctgg atgatagcgg cgatattagc agcaccgtga ttaactttag ccagaaatat   5040
ctgtatggca ttgatagctg cgtgaacaaa gtggtgatta gcccgaacat ttataccgat   5100
gaaattaaca ttaccccggt gtatgaaacc aacaacacct atccggaagt gattgtgctg   5160
gatgcgaact atattaacga aaaaattaac gtgaacatta acgatctgag cattcgttat   5220
gtgtggagca acgatggcaa cgatttttatt ctgatgagca ccagcgaaga aaacaaagtg   5280
agccaggtga aaattcgttt tgtgaacgtg tttaaagata aaccctggc gaacaaactg   5340
agctttaact ttagcgataa acaggatgtg cctgtgagcg aaattattct gagctttacc   5400
ccgagctatt atgaagatgg cctgattggc tatgatctgg gcctggttag cctgtataac   5460
gaaaaatttt atattaacaa ctttggcatg atggttagcg gcctgattta tattaacgat   5520
agcctgtatt attttaaacc gccggtgaac aacctgatta ccggctttgt gaccgtgggc   5580
gatgataaat attattttaa cccgattaac ggcggcgcgg cgagcattgg cgaaaccatt   5640
attgatgata aaaactatta ttttaaccag agcggcgtgc tgcagaccgg cgtgtttagc   5700
accgaagatg gctttaaata ttttgcgccg gcgaacaccc tggatgaaaa cctggaaggc   5760
gaagcgatcg atttcaccgg caaactgatc atcgatgaaa acatctacta cttcgatgat   5820
aactaccgtg gcgcggtgga atggaaagaa ctggatggcg aaatgcatta ttttagcccg   5880
gaaaccggca aagcgtttaa aggcctgaac cagattggcg attataaata ttattttaac   5940
agcgatggcg tgatgcagaa aggctttgtg agcattaacg ataacaaaca ttattttgat   6000
gatagcggcg tgatgaaagt gggctatacc gaaattgatg gcaaacattt ttattttgcg   6060
gaaaacggcg aaatgcagat tggcgtgttt aatacggaag acggttttaa atattttgcg   6120
catcataacg aagatctggg caacgaagaa ggcgaagaaa tcagctacag cggcattctg   6180
aactttaaca acaaaattta ttacttcgat gatagcttta ccgcggtggt gggctggaaa   6240
gatctggaag atggcagcaa atattatttt gatgaagata ccgcggaagc gtatattggc   6300
ctgagcctga ttaacgatgg ccagtattat tttaacgatg atggcattat gcaagtgggc   6360
tttgtgacca ttaacgataa agtgttttat tttagcgata gcggcattat tgaaagcggc   6420
gtgcagaaca ttgatgataa ctatttttat attgatgata acggcattgt gcagattggc   6480
gtgtttgata ccagcgatgg ctacaaatac ttcgccccgg cgaacaccgt gaacgataac   6540
atttatggcc aggcggtgga atatagcggc ctggtgcgtg tgggcgaaga tgtgtattat   6600
tttggcgaaa cctataccat tgaaaccggc tggatctacg atatggaaaa cgaaagcgat   6660
aaatactact tcaacccgga aaccaaaaaa gcgtgcaaag gcatcaacct gatcgatgat   6720
atcaaatact acttcgatga aaaaggcatc atgcgtaccg gcctgattag ctttgaaaac   6780
aacaattact acttcaacga aaatggtgaa atgcagttcg gctacatcaa catcgaagat   6840
aaaatgtttt attttggcga agatggcgtg atgcaaatcg gcgtgtttaa caccccggac   6900
ggtttcaaat attttgcgca tcaaaatacc ctggatgaaa actttgaagg cgaaagcatt   6960
```

```
aactataccg gctggctgga tctggatgaa aaacgttatt attttaccga tgaatatatt   7020

gcggcgaccg gcagcgtgat tattgatggc gaagaatatt attttgatcc ggataccgcg   7080

cagctggtga ttagcgaata a                                              7101


<210> SEQ ID NO 8
<211> LENGTH: 7101
<212> TYPE: DNA
<213> ORGANISM: Clostridium difficile
<220> FEATURE:
<221> NAME/KEY: gene
<222> LOCATION: (1)..(7101)

<400> SEQUENCE: 8

atgagcctgg tgaaccgtaa acagctggaa aaaatggcga acgtgcgttt tcgtacccag     60

gaagatgaat atgtggcgat tctggatgcg ctggaagaat atcataacat gagcgaaaac    120

accgtggtgg aaaaatacct gaaactgaaa gatatcaaca gcctgaccga tatctacatc    180

gatacctaca agaaaagcgg ccgtaacaaa gcgctgaaaa aatttaaaga atatctggtg    240

accgaagtgc tggaactgaa aaacaacaac ctgaccccgg tggaaaagaa cctgcatttt    300

gtgtggattg gcggccagat taacgatacc gcgattaact atattaacca gtggaaagat    360

gtgaacagcg attataacgt gaacgtgttt tatgatagca acgcgtttct gattaacacc    420

ctgaagaaaa ccgtggtgga aagcgcgatt aacgataccc tggaaagctt tcgtgaaaac    480

ctgaacgatc cgcgtttcga ttacaacaaa tttttccgta aacgtatgga aatcatctac    540

gataaacaga aaaactttat taactattat aaagcgcagc gtgaagaaaa cccggaactg    600

atcatcgatg atatcgtgaa aacctacctg agcaacgaat acagcaaaga aatcgatgaa    660

ctgaacacct acatcgaaga aagcctgaac aaaatcaccc agaacagcgg caacgatgtg    720

cgtaactttg aagaatttaa aaacggcgaa agctttaacc tgtatgaaca ggaactggtg    780

gaacgttgga acctggcggc ggcgagcgat attctgcgta ttagcgcgct gaaagaaatt    840

ggcggcatgt atctgggtgt gggtatgctg ccgggcattc agccggatct gtttgaaagc    900

attgaaaaac cgagcagcgt gaccgtggat ttttgggaaa tgaccaaact ggaagcgatc    960

atgaaataca aagaatacat cccggaatac accagcgaac atttcgatat gctggatgaa   1020

gaagtgcaga gcagctttga aagcgtgctg gcgagcaaaa gcgataaaag cgaaattttt   1080

agcagcctgg gcgatatgga agcgagcccg ctggaagtga aaattgcgtt taacagcaaa   1140

ggcattatta accagggcct gattagcgtg aaagatagct attgcagcaa cctgattgtg   1200

aaacagattg aaaaccgtta taaaattctg aacaacagcc tgaacccggc gattagcgaa   1260

gataacgatt ttaacaccac caccaacacc tttattgata gcattatggc ggaagcgaac   1320

gcggataacg gccgttttat gatggaactg ggcaaatatc tgcgtgtggg tttctttccg   1380

gatgtgaaaa ccaccattaa cctgagcggc ccggaagcgt atgcggcggc gtatcaggat   1440

ctgctgatgt ttaaagaagg cagcatgaac attcatctga ttgaagcgga tctgcgtaac   1500

tttgaaatta gcaaaaccaa cattagccag agcaccgaac aggaaatggc gagcctgtgg   1560

agctttgatg atgcgcgtgc gaaagcgcag tttgaagaat ataaacgtaa ctattttgaa   1620

ggcagcctgg gcgaagatga taacctggat tttagccaga acattgtggt ggataaagaa   1680

tatctgctgg aaaaaattag cagcctggcg cgtagcagcg aacgtggcta tattcattat   1740

attgtgcagc tgcagggcga taaaattagc tatgaagcgg cgtgcaacct gtttgcgaaa   1800

accccgtatg atagcgtgct gtttcagaaa aacattgaag atagcgaaat tgcgtattat   1860

tataacccgg gcgatggcga aatccaggaa atcgataaat acaaaatccc gagcatcatc   1920
```

```
agcgatcgtc cgaaaatcaa actgaccttt attggccatg gcaaagatga atttaacacc   1980
gatatttttg cgggctttga tgtggatagc ctgagcaccg aaatcgaagc ggcgattgat   2040
ctggcgaaag aagatattag cccgaaaagc attgaaatta acctgctggg ctgcaacatg   2100
tttagctata gcattaacgt ggaagaaacc tatccgggca aactgctgct gaaagtgaaa   2160
gataaaatta gcgaactgat gccgagcatt agccaggata gcattattgt gagcgcgaac   2220
cagtatgaag tgcgtattaa cagcgaaggc cgtcgtgaac tgctggatca tagcggcgaa   2280
tggatcaaca aagaagaaag catcatcaaa gatatcagca gcaaagaata catcagcttc   2340
aacccgaaag aaaacaaaat caccgtgaaa agcaaaaacc tgccggaact gagcaccctg   2400
ctgcaggaaa ttcgtaacaa cagcaacagc agcgatattg aactggaaga aaaagtgatg   2460
ctgaccgaat gcgaaattaa cgtgattagc aacattgata cccagattgt ggaagaacgt   2520
attgaagaag cgaaaaacct gaccagcgat agcattaact atattaaaga tgaatttaaa   2580
ctgattgaaa gcattagcga tgcgctgtgc gatctgaaac agcagaacga actggaagac   2640
agccatttta ttagctttga agatattagc gaaaccgatg aaggctttag cattcgtttt   2700
attaacaaag aaaccggcga aagcattttt gtggaaaccg aaaaaaccat ttttagcgaa   2760
tacgcgaacc atatcaccga agaaatcagc aaaatcaaag gcaccatttt tgataccgtg   2820
aacggcaaac tggtgaaaaa agtgaacctg gataccaccc atgaagtgaa caccctgaac   2880
gcggcatttt tcattcagag cctgattgaa tataacagca gcaaagaaag cctgagcaac   2940
ctgagcgtgg cgatgaaagt gcaggtgtat gcgcagctgt ttagcaccgg cctgaacacc   3000
attaccgacg cggcgaaagt ggtggaactg gttagcaccg cgctggatga aaccattgat   3060
ctgctgccga ccctgagcga aggcctgccg attattgcga ccattattga tggcgtgagc   3120
ctgggcgcgg cgattaaaga actgagcgaa accagcgatc cgctgctgcg tcaggaaatt   3180
gaagcgaaaa ttggcattat ggcggtgaac ctgaccaccg cgaccaccgc gattattacc   3240
agcagcctgg gcattgcgag cggctttagc attctgctgg tgccgctggc gggcattagc   3300
gcgggcattc cgagcctggt gaacaacgaa ctggtgctgc gtgataaagc gaccaaagtg   3360
gtggattatt ttaaacatgt gagcctggtg gaaaccgaag gcgtgtttac cctgctggat   3420
gataaaatta tgatgccgca ggatgatctg gtgattagcg aaattgattt taacaacaac   3480
agcattgtgc tgggcaaatg cgaaatttgg cgtatggaag gcggcagcgg ccataccgtg   3540
accgatgata ttgatcattt ctttagcgcg ccgagcatta cctatcgtga accgcatctg   3600
agcatttatg atgtgctgga agtgcagaaa gaagaactgg atctgagcaa agatctgatg   3660
gtgctgccga acgcaccgaa ccgtgtgttt gcatgggaaa ccggttggac cccgggtctg   3720
cgtagcctgg aaaacgatgg caccaaactg ctggatcgta ttcgtgataa ctatgaaggc   3780
gaattttatt ggcgttattt tgcgtttatt gcggatgcgc tgattaccac cctgaaaccg   3840
cgttatgaag ataccaacat tcgtattaac ctggatagca acacccgtag ctttattgtg   3900
ccgattatta ccaccgaata tattcgtgaa aaactgagct atagctttta tggcagcggc   3960
ggcacctatg cgctgagcct gagccagtat aacatgggca ttaacattga actgagcgaa   4020
agcgatgtgt ggattattga tgtggataac gtggtgcgtg atgtgaccat tgaaagcgat   4080
aaaattaaaa aaggcgatct gattgaaggc attctgagca ccctgagcat tgaagaaaac   4140
aaaattattc tgaacagcca tgaaattaac tttagcggcg aagtgaacgg cagcaacggc   4200
tttgtgagcc tgacctttag cattctggaa ggcattaacg cgattattga agtggatctg   4260
ctgagcaaaa gctataaact gctgattagc ggcgaactga aaattctgat gctgaacagc   4320
```

-continued

```
aaccatattc agcagaaaat tgattatatt ggctttaaca gcgaactgca gaaaaacatt   4380
ccgtatagct ttgtggatag cgaaggcaaa gaaaacggct ttattaacgg cagcaccaaa   4440
gaaggcctgt ttgtgagcga actgccggat gtggtgctga ttagcaaagt gtatatggat   4500
gatagcaaac cgagctttgg ctattatagc aacaacctga aagatgtgaa agtgattacc   4560
aaagataacg tgaacattct gaccggctat tatctgaaag atgatattaa aattagcctg   4620
agcctgaccc tgcaggatga aaaaaccatt aaactgaaca gcgtgcatct ggatgaaagc   4680
ggcgtggcgg aaattctgaa atttatgaac cgtaaaggca acaccaacac cagcgatagc   4740
ctgatgagct ttctggaaag catgaacatc aaaagcatct tcgtgaactt tctgcagagc   4800
aacatcaaat tcatcctgga tgcgaacttc atcatcagcg gcaccaccag cattggccag   4860
ttcgaattta tttgcgatga aaacgataac atccagccgt acttcatcaa attcaacacc   4920
ctggaaacca actataccct gtatgtgggc aaccgtcaga acatgattgt ggaaccgaac   4980
tatgatctgg atgatagcgg cgatattagc agcaccgtga ttaactttag ccagaaatat   5040
ctgtatggca ttgatagctg cgtgaacaaa gtggtgatta gcccgaacat ttataccgat   5100
gaaattaaca ttaccccggt gtatgaaacc aacaacacct atccggaagt gattgtgctg   5160
gatgcgaact atattaacga aaaaattaac gtgaacatta acgatctgag cattcgttat   5220
gtgtggagca acgatggcaa cgattttatt ctgatgagca ccagcgaaga aaacaaagtg   5280
agccaggtga aaattcgttt tgtgaacgtg tttaaagata aaaccctggc gaacaaactg   5340
agctttaact ttagcgataa acaggatgtg cctgtgagcg aaattattct gagctttacc   5400
ccgagctatt atgaagatgg cctgattggc tatgatctgg gcctggttag cctgtataac   5460
gaaaaatttt atattaacaa ctttggcatg atggttagcg gcctgattta tattaacgat   5520
agcctgtatt attttaaacc gccggtgaac aacctgatta ccggctttgt gaccgtgggc   5580
gatgataaat attattttaa cccgattaac ggcggcgcgg cgagcattgg cgaaaccatt   5640
attgatgata aaaactatta ttttaaccag agcggcgtgc tgcagaccgg cgtgtttagc   5700
accgaagatg gctttaaata ttttgcgccg gcgaacaccc tggatgaaaa cctggaaggc   5760
gaagcgatcg atttcaccgg caaactgatc atcgatgaaa acatctacta cttcgatgat   5820
aactaccgtg gcgcggtgga atggaaagaa ctggatggcg aaatgcatta ttttagcccg   5880
gaaaccggca aagcgtttaa aggcctgaac cagattggcg attataaata ttattttaac   5940
agcgatggcg tgatgcagaa aggctttgtg agcattaacg ataacaaaca ttattttgat   6000
gatagcggcg tgatgaaagt gggctatacc gaaattgatg gcaaacattt ttattttgcg   6060
gaaaacggcg aaatgcagat tggcgtgttt aatacggaag acggttttaa atattttgcg   6120
catcataacg aagatctggg caacgaagaa ggcgaagaaa tcagctacag cggcattctg   6180
aactttaaca acaaaattta ttacttcgat gatagcttta ccgcggtggt gggctggaaa   6240
gatctggaag atggcagcaa atattatttt gatgaagata ccgcggaagc gtatattggc   6300
ctgagcctga ttaacgatgg ccagtattat tttaacgatg atggcattat gcaagtgggc   6360
tttgtgacca ttaacgataa agtgttttat tttagcgata gcggcattat tgaaagcggc   6420
gtgcagaaca ttgatgataa ctatttttat attgatgata acggcattgt gcagattggc   6480
gtgtttgata ccagcgatgg ctacaaatac ttcgccccgg cgaacaccgt gaacgataac   6540
atttatggcc aggcggtgga atatagcggc ctggtgcgtg tgggcgaaga tgtgtattat   6600
tttggcgaaa cctataccat tgaaaccggc tggatctacg atatggaaaa cgaaagcgat   6660
aaatactact tcaacccgga aaccaaaaaa gcgtgcaaag gcatcaacct gatcgatgat   6720
```

-continued atcaaatact acttcgatga aaaaggcatc atgcgtaccg gcctgattag ctttgaaaac 6780
aacaattact acttcaacga aaatggtgaa atgcagttcg gctacatcaa catcgaagat 6840
aaaatgtttt attttggcga agatggcgtg atgcaaatcg gcgtgtttaa caccccggac 6900
ggtttcaaat attttgcgca tcaaaatacc ctggatgaaa actttgaagg cgaaagcatt 6960
aactataccg gctggctgga tctggatgaa aaacgttatt attttaccga tgaatatatt 7020
gcggcgaccg gcagcgtgat tattgatggc gaagaatatt attttgatcc ggataccgcg 7080
cagctggtga ttagcgaata a 7101

<210> SEQ ID NO 9
<211> LENGTH: 7101
<212> TYPE: DNA
<213> ORGANISM: Clostridium difficile
<220> FEATURE:
<221> NAME/KEY: gene
<222> LOCATION: (1)..(7101)

<400> SEQUENCE: 9
atgagcctgg tgaaccgtaa acagctggaa aaaatggcga acgtgcgttt tcgtacccag 60
gaagatgaat atgtggcgat tctggatgcg ctggaagaat atcataacat gagcgaaaac 120
accgtggtgg aaaaatacct gaaactgaaa gatatcaaca gcctgaccga tatctacatc 180
gatacctaca agaaaagcgg ccgtaacaaa gcgctgaaaa aatttaaaga atatctggtg 240
accgaagtgc tggaactgaa aaacaacaac ctgaccccgg tggaaaagaa cctgcatttt 300
gtggcgattg gcggccagat taacgatacc gcgattaact atattaacca gtggaaagat 360
gtgaacagcg attataacgt gaacgtgttt tatgatagca acgcgtttct gattaacacc 420
ctgaagaaaa ccgtggtgga aagcgcgatt aacgataccc tggaaagctt tcgtgaaaac 480
ctgaacgatc cgcgtttcga ttacaacaaa tttttccgta aacgtatgga aatcatctac 540
gataaacaga aaaactttat taactattat aaagcgcagc gtgaagaaaa cccggaactg 600
atcatcgatg atatcgtgaa aacctacctg agcaacgaat acagcaaaga aatcgatgaa 660
ctgaacacct acatcgaaga aagcctgaac aaaatcaccc agaacagcgg caacgatgtg 720
cgtaactttg aagaatttaa aaacggcgaa agctttaacc tgtatgaaca ggaactggtg 780
gaacgttgga acctggcggc ggcgagcgat attctgcgta ttagcgcgct gaaagaaatt 840
ggcggcatgt atctggatgt ggatatgctg ccgggcattc agccggatct gtttgaaagc 900
attgaaaaac cgagcagcgt gaccgtggat ttttgggaaa tgaccaaact ggaagcgatc 960
atgaaataca aagaatacat cccggaatac accagcgaac atttcgatat gctggatgaa 1020
gaagtgcaga gcagctttga aagcgtgctg gcgagcaaaa gcgataaaag cgaaattttt 1080
agcagcctgg gcgatatgga agcgagcccg ctggaagtga aaattgcgtt taacagcaaa 1140
ggcattatta accagggcct gattagcgtg aaagatagct attgcagcaa cctgattgtg 1200
aaacagattg aaaaccgtta taaaattctg aacaacagcc tgaacccggc gattagcgaa 1260
gataacgatt ttaacaccac caccaacacc tttattgata gcattatggc ggaagcgaac 1320
gcggataacg gccgttttat gatggaactg ggcaaatatc tgcgtgtggg tttctttccg 1380
gatgtgaaaa ccaccattaa cctgagcggc ccggaagcgt atgcggcggc gtatcaggat 1440
ctgctgatgt ttaaagaagg cagcatgaac attcatctga ttgaagcgga tctgcgtaac 1500
tttgaaatta gcaaaaccaa cattagccag agcaccgaac aggaaatggc gagcctgtgg 1560
agctttgatg atgcgcgtgc gaaagcgcag tttgaagaat ataaacgtaa ctattttgaa 1620

-continued

```
ggcagcctgg gcgaagatga taacctggat tttagccaga acattgtggt ggataaagaa   1680
tatctgctgg aaaaaattag cagcctggcg cgtagcagcg aacgtggcta tattcattat   1740
attgtgcagc tgcagggcga taaaattagc tatgaagcgg cgtgcaacct gtttgcgaaa   1800
accccgtatg atagcgtgct gtttcagaaa aacattgaag atagcgaaat tgcgtattat   1860
tataacccgg gcgatggcga aatccaggaa atcgataaat acaaaatccc gagcatcatc   1920
agcgatcgtc cgaaaatcaa actgaccttt attggccatg gcaaagatga atttaacacc   1980
gatatttttg cgggctttga tgtggatagc ctgagcaccg aaatcgaagc ggcgattgat   2040
ctggcgaaag aagatattag cccgaaaagc attgaaatta acctgctggg ctgcaacatg   2100
tttagctata gcattaacgt ggaagaaacc tatccgggca aactgctgct gaaagtgaaa   2160
gataaaatta gcgaactgat gccgagcatt agccaggata gcattattgt gagcgcgaac   2220
cagtatgaag tgcgtattaa cagcgaaggc cgtcgtgaac tgctggatca tagcggcgaa   2280
tggatcaaca aagaagaaag catcatcaaa gatatcagca gcaaagaata catcagcttc   2340
aacccgaaag aaaacaaaat caccgtgaaa agcaaaaacc tgccggaact gagcaccctg   2400
ctgcaggaaa ttcgtaacaa cagcaacagc agcgatattg aactggaaga aaaagtgatg   2460
ctgaccgaat gcgaaattaa cgtgattagc aacattgata cccagattgt ggaagaacgt   2520
attgaagaag cgaaaaacct gaccagcgat agcattaact atattaaaga tgaatttaaa   2580
ctgattgaaa gcattagcga tgcgctgtgc gatctgaaac agcagaacga actggaagac   2640
agccatttta ttagctttga agatattagc gaaaccgatg aaggctttag cattcgtttt   2700
attaacaaag aaaccggcga aagcattttt gtggaaaccg aaaaaaccat ttttagcgaa   2760
tacgcgaacc atatcaccga agaaatcagc aaaatcaaag gcaccatttt tgataccgtg   2820
aacggcaaac tggtgaaaaa agtgaacctg gataccaccc atgaagtgaa caccctgaac   2880
gcggcatttt tcattcagag cctgattgaa tataacagca gcaaagaaag cctgagcaac   2940
ctgagcgtgg cgatgaaagt gcaggtgtat gcgcagctgt ttagcaccgg cctgaacacc   3000
attaccgacg cggcgaaagt ggtggaactg gttagcaccg cgctggatga aaccattgat   3060
ctgctgccga ccctgagcga aggcctgccg attattgcga ccattattga tggcgtgagc   3120
ctgggcgcgg cgattaaaga actgagcgaa accagcgatc cgctgctgcg tcaggaaatt   3180
gaagcgaaaa ttggcattat ggcggtgaac ctgaccaccg cgaccaccgc gattattacc   3240
agcagcctgg gcattgcgag cggctttagc attctgctgg tgccgctggc gggcattagc   3300
gcgggcattc cgagcctggt gaacaacgaa ctggtgctgc gtgataaagc gaccaaagtg   3360
gtggattatt ttaaacatgt gagcctggtg gaaaccgaag gcgtgtttac cctgctggat   3420
gataaaatta tgatgccgca ggatgatctg gtgattagcg aaattgattt taacaacaac   3480
agcattgtgc tgggcaaatg cgaaatttgg cgtatggaag gcggcagcgg ccataccgtg   3540
accgatgata ttgatcattt ctttagcgcg ccgagcatta cctatcgtga accgcatctg   3600
agcatttatg atgtgctgga agtgcagaaa gaagaactgg atctgagcaa agatctgatg   3660
gtgctgccga acgcaccgaa ccgtgtgttt gcatgggaaa ccggttggac cccgggtctg   3720
cgtagcctgg aaaacgatgg caccaaactg ctggatcgta ttcgtgataa ctatgaaggc   3780
gaattttatt ggcgttattt tgcgtttatt gcggatgcgc tgattaccac cctgaaaccg   3840
cgttatgaag ataccaacat tcgtattaac ctggatagca acacccgtag ctttattgtg   3900
ccgattatta ccaccgaata tattcgtgaa aaactgagct atagctttta tggcagcggc   3960
ggcacctatg cgctgagcct gagccagtat aacatgggca ttaacattga actgagcgaa   4020
```

-continued agcgatgtgt ggattattga tgtggataac gtggtgcgtg atgtgaccat tgaaagcgat 4080
aaaattaaaa aaggcgatct gattgaaggc attctgagca ccctgagcat tgaagaaaac 4140
aaaattattc tgaacagcca tgaaattaac tttagcggcg aagtgaacgg cagcaacggc 4200
tttgtgagcc tgacctttag cattctggaa ggcattaacg cgattattga agtggatctg 4260
ctgagcaaaa gctataaact gctgattagc ggcgaactga aaattctgat gctgaacagc 4320
aaccatattc agcagaaaat tgattatatt ggctttaaca gcgaactgca gaaaaacatt 4380
ccgtatagct ttgtggatag cgaaggcaaa gaaaacggct ttattaacgg cagcaccaaa 4440
gaaggcctgt ttgtgagcga actgccggat gtggtgctga ttagcaaagt gtatatggat 4500
gatagcaaac cgagctttgg ctattatagc aacaacctga aagatgtgaa agtgattacc 4560
aaagataacg tgaacattct gaccggctat tatctgaaag atgatattaa aattagcctg 4620
agcctgaccc tgcaggatga aaaaaccatt aaactgaaca gcgtgcatct ggatgaaagc 4680
ggcgtggcgg aaattctgaa atttatgaac cgtaaaggca acaccaacac cagcgatagc 4740
ctgatgagct ttctggaaag catgaacatc aaaagcatct tcgtgaactt tctgcagagc 4800
aacatcaaat tcatcctgga tgcgaacttc atcatcagcg gcaccaccag cattggccag 4860
ttcgaattta tttgcgatga aaacgataac atccagccgt acttcatcaa attcaacacc 4920
ctggaaacca actataccct gtatgtgggc aaccgtcaga acatgattgt ggaaccgaac 4980
tatgatctgg atgatagcgg cgatattagc agcaccgtga ttaactttag ccagaaatat 5040
ctgtatggca ttgatagctg cgtgaacaaa gtggtgatta gcccgaacat ttataccgat 5100
gaaattaaca ttaccccggt gtatgaaacc aacaacacct atccggaagt gattgtgctg 5160
gatgcgaact atattaacga aaaaattaac gtgaacatta acgatctgag cattcgttat 5220
gtgtggagca acgatggcaa cgattttatt ctgatgagca ccagcgaaga aaacaaagtg 5280
agccaggtga aaattcgttt tgtgaacgtg tttaaagata aaaccctggc gaacaaactg 5340
agctttaact ttagcgataa acaggatgtg cctgtgagcg aaattattct gagctttacc 5400
ccgagctatt atgaagatgg cctgattggc tatgatctgg gcctggttag cctgtataac 5460
gaaaaatttt atattaacaa ctttggcatg atggttagcg gcctgattta tattaacgat 5520
agcctgtatt attttaaacc gccggtgaac aacctgatta ccggctttgt gaccgtgggc 5580
gatgataaat attattttaa cccgattaac ggcggcgcgg cgagcattgg cgaaaccatt 5640
attgatgata aaaactatta ttttaaccag agcggcgtgc tgcagaccgg cgtgtttagc 5700
accgaagatg gctttaaata ttttgcgccg gcgaacaccc tggatgaaaa cctggaaggc 5760
gaagcgatcg atttcaccgg caaactgatc atcgatgaaa acatctacta cttcgatgat 5820
aactaccgtg gcgcggtgga atggaaagaa ctggatggcg aaatgcatta ttttagcccg 5880
gaaaccggca aagcgtttaa aggcctgaac cagattggcg attataaata ttattttaac 5940
agcgatggcg tgatgcagaa aggctttgtg agcattaacg ataacaaaca ttattttgat 6000
gatagcggcg tgatgaaagt gggctatacc gaaattgatg gcaaacattt ttattttgcg 6060
gaaaacggcg aaatgcagat tggcgtgttt aatacggaag acggttttaa atattttgcg 6120
catcataacg aagatctggg caacgaagaa ggcgaagaaa tcagctacag cggcattctg 6180
aactttaaca acaaaattta ttacttcgat gatagcttta ccgcggtggt gggctggaaa 6240
gatctggaag atggcagcaa atattatttt gatgaagata ccgcggaagc gtatattggc 6300
ctgagcctga ttaacgatgg ccagtattat tttaacgatg atggcattat gcaagtgggc 6360
tttgtgacca ttaacgataa agtgttttat tttagcgata gcggcattat tgaaagcggc 6420

-continued gtgcagaaca ttgatgataa ctatttttat attgatgata acggcattgt gcagattggc 6480
gtgtttgata ccagcgatgg ctacaaatac ttcgccccgg cgaacaccgt gaacgataac 6540
atttatggcc aggcggtgga atatagcggc ctggtgcgtg tgggcgaaga tgtgtattat 6600
tttggcgaaa cctataccat tgaaaccggc tggatctacg atatggaaaa cgaaagcgat 6660
aaatactact tcaacccgga aaccaaaaaa gcgtgcaaag gcatcaacct gatcgatgat 6720
atcaaatact acttcgatga aaaaggcatc atgcgtaccg gcctgattag ctttgaaaac 6780
aacaattact acttcaacga aaatggtgaa atgcagttcg gctacatcaa catcgaagat 6840
aaaatgtttt attttggcga agatggcgtg atgcaaatcg gcgtgtttaa caccccggac 6900
ggtttcaaat attttgcgca tcaaaatacc ctggatgaaa actttgaagg cgaaagcatt 6960
aactataccg gctggctgga tctggatgaa aaacgttatt attttaccga tgaatatatt 7020
gcggcgaccg gcagcgtgat tattgatggc gaagaatatt attttgatcc ggataccgcg 7080
cagctggtga ttagcgaata a 7101

<210> SEQ ID NO 10
<211> LENGTH: 7101
<212> TYPE: DNA
<213> ORGANISM: Clostridium difficile
<220> FEATURE:
<221> NAME/KEY: gene
<222> LOCATION: (1)..(7101)

<400> SEQUENCE: 10
atgagcctgg tgaaccgtaa acagctggaa aaaatggcga acgtgcgttt tcgtacccag 60
gaagatgaat atgtggcgat tctggatgcg ctggaagaat atcataacat gagcgaaaac 120
accgtggtgg aaaaatacct gaaactgaaa gatatcaaca gcctgaccga tatctacatc 180
gatacctaca agaaaagcgg ccgtaacaaa gcgctgaaaa aatttaaaga atatctggtg 240
accgaagtgc tggaactgaa aaacaacaac ctgaccccgg tggaaaagaa cctgcatttt 300
gtgtggattg gcggccagat taacgatacc gcgattaact atattaacca gtggaaagat 360
gtgaacagcg attataacgt gaacgtgttt tatgatagca acgcgtttct gattaacacc 420
ctgaagaaaa ccgtggtgga aagcgcgatt aacgataccc tggaaagctt tcgtgaaaac 480
ctgaacgatc cgcgtttcga ttacaacaaa tttttccgta aacgtatgga aatcatctac 540
gataaacaga aaaactttat taactattat aaagcgcagc gtgaagaaaa cccggaactg 600
atcatcgatg atatcgtgaa aacctacctg agcaacgaat acagcaaaga aatcgatgaa 660
ctgaacacct acatcgaaga aagcctgaac aaaatcaccc agaacagcgg caacgatgtg 720
cgtaactttg aagaatttaa aaacggcgaa agctttaacc tgtatgaaca ggaactggtg 780
gaacgttgga acctggcggc ggcgagcgat attctgcgta ttagcgcgct gaaagaaatt 840
ggcggcatgt atctgggtgt gggtatgctg ccgggcattc agccggatct gtttgaaagc 900
attgaaaaac cgagcagcgt gaccgtggat ttttgggaaa tgaccaaact ggaagcgatc 960
atgaaataca aagaatacat cccggaatac accagcgaac atttcgatat gctggatgaa 1020
gaagtgcaga gcagctttga aagcgtgctg gcgagcaaaa gcgataaaag cgaaattttt 1080
agcagcctgg gcgatatgga agcgagcccg ctggaagtga aaattgcgtt taacagcaaa 1140
ggcattatta accagggcct gattagcgtg aaagatagct attgcagcaa cctgattgtg 1200
aaacagattg aaaaccgtta taaaattctg aacaacagcc tgaacccggc gattagcgaa 1260
gataacgatt ttaacaccac caccaacacc tttattgata gcattatggc ggaagcgaac 1320
gcggataacg gccgttttat gatggaactg ggcaaatatc tgcgtgtggg tttctttccg 1380

-continued

```
gatgtgaaaa ccaccattaa cctgagcggc ccggaagcgt atgcggcggc gtatcaggat   1440
ctgctgatgt ttaaagaagg cagcatgaac attcatctga ttgaagcgga tctgcgtaac   1500
tttgaaatta gcaaaaccaa cattagccag agcaccgaac aggaaatggc gagcctgtgg   1560
agctttgatg atgcgcgtgc gaaagcgcag tttgaagaat ataaacgtaa ctattttgaa   1620
ggcagcctgg gcgaagatga taacctggat tttagccaga acattgtggt ggataaagaa   1680
tatctgctgg aaaaaattag cagcctggcg cgtagcagcg aacgtggcta tattcattat   1740
attgtgcagc tgcagggcga taaaattagc tatgaagcgg cgtgcaacct gtttgcgaaa   1800
accccgtatg atagcgtgct gtttcagaaa aacattgaag atagcgaaat tgcgtattat   1860
tataacccgg gcgatggcga aatccaggaa atcgataaat acaaaatccc gagcatcatc   1920
agcgatcgtc cgaaaatcaa actgaccttt attggccatg gcaaagatga atttaacacc   1980
gatatttttg cgggctttga tgtggatagc ctgagcaccg aaatcgaagc ggcgattgat   2040
ctggcgaaag aagatattag cccgaaaagc attgaaatta acctgctggg ctgcaacatg   2100
tttagctata gcattaacgt ggaagaaacc tatccgggca aactgctgct gaaagtgaaa   2160
gataaaatta gcgaactgat gccgagcatt agccaggata gcattattgt gagcgcgaac   2220
cagtatgaag tgcgtattaa cagcgaaggc cgtcgtgaac tgctggatca tagcggcgaa   2280
tggatcaaca aagaagaaag catcatcaaa gatatcagca gcaaagaata catcagcttc   2340
aacccgaaag aaaacaaaat caccgtgaaa agcaaaaacc tgccggaact gagcaccctg   2400
ctgcaggaaa ttcgtaacaa cagcaacagc agcgatattg aactggaaga aaaagtgatg   2460
ctgaccgaat gcgaaattaa cgtgattagc aacattgata cccagattgt ggaagaacgt   2520
attgaagaag cgaaaaacct gaccagcgat agcattaact atattaaaga tgaatttaaa   2580
ctgattgaaa gcattagcga tgcgctgtgc gatctgaaac agcagaacga actggaagac   2640
agccatttta ttagctttga agatattagc gaaaccgatg aaggctttag cattcgtttt   2700
attaacaaag aaaccggcga aagcattttt gtggaaaccg aaaaaaccat ttttagcgaa   2760
tacgcgaacc atatcaccga agaaatcagc aaaatcaaag gcaccatttt tgataccgtg   2820
aacggcaaac tggtgaaaaa agtgaacctg gataccaccc atgaagtgaa caccctgaac   2880
gcggcatttt tcattcagag cctgattgaa tataacagca gcaaagaaag cctgagcaac   2940
ctgagcgtgg cgatgaaagt gcaggtgtat gcgcagctgt ttagcaccgg cctgaacacc   3000
attaccgacg cggcgaaagt ggtggaactg gttagcaccg cgctggatga aaccattgat   3060
ctgctgccga ccctgagcga aggcctgccg attattgcga ccattattga tggcgtgagc   3120
ctgggcgcgg cgattaaaga actgagcgaa accagcgatc cgctgctgcg tcaggaaatt   3180
gaagcgaaaa ttggcattat ggcggtgaac ctgaccaccg cgaccaccgc gattattacc   3240
agcagcctgg gcattgcgag cggctttagc attctgctgg tgccgctggc gggcattagc   3300
gcgggcattc cgagcctggt gaacaacgaa ctggtgctgc gtgataaagc gaccaaagtg   3360
gtggattatt ttaaacatgt gagcctggtg gaaaccgaag gcgtgtttac cctgctggat   3420
gataaaatta tgatgccgca ggatgatctg gtgattagcg aaattgattt taacaacaac   3480
agcattgtgc tgggcaaatg cgaaatttgg cgtatggaag gcggcagcgg ccataccgtg   3540
accgatgata ttgatcattt ctttagcgcg ccgagcatta cctatcgtga accgcatctg   3600
agcatttatg atgtgctgga agtgcagaaa gaagaactgg atctgagcaa agatctgatg   3660
gtgctgccga acgcaccgaa ccgtgtgttt gcatgggaaa ccggttggac cccgggtctg   3720
cgtagcctgg aaaacgatgg caccaaactg ctggatcgta ttcgtgataa ctatgaaggc   3780
```

```
gaattttatt ggcgttattt tgcgtttatt gcggatgcgc tgattaccac cctgaaaccg   3840
cgttatgaag ataccaacat tcgtattaac ctggatagca acacccgtag ctttattgtg   3900
ccgattatta ccaccgaata tattcgtgaa aaactgagct atagctttta tggcagcggc   3960
ggcacctatg cgctgagcct gagccagtat aacatgggca ttaacattga actgagcgaa   4020
agcgatgtgt ggattattga tgtggataac gtggtgcgtg atgtgaccat tgaaagcgat   4080
aaaattaaaa aaggcgatct gattgaaggc attctgagca ccctgagcat tgaagaaaac   4140
aaaattattc tgaacagcca tgaaattaac tttagcggcg aagtgaacgg cagcaacggc   4200
tttgtgagcc tgacctttag cattctggaa ggcattaacg cgattattga agtggatctg   4260
ctgagcaaaa gctataaact gctgattagc ggcgaactga aaattctgat gctgaacagc   4320
aaccatattc agcagaaaat tgattatatt ggctttaaca gcgaactgca gaaaaacatt   4380
ccgtatagct ttgtggatag cgaaggcaaa gaaaacggct ttattaacgg cagcaccaaa   4440
gaaggcctgt ttgtgagcga actgccggat gtggtgctga ttagcaaagt gtatatggat   4500
gatagcaaac cgagctttgg ctattatagc aacaacctga aagatgtgaa agtgattacc   4560
aaagataacg tgaacattct gaccggctat tatctgaaag atgatattaa aattagcctg   4620
agcctgaccc tgcaggatga aaaaaccatt aaactgaaca gcgtgcatct ggatgaaagc   4680
ggcgtggcgg aaattctgaa atttatgaac cgtaaaggca acaccaacac cagcgatagc   4740
ctgatgagct ttctggaaag catgaacatc aaaagcatct tcgtgaactt tctgcagagc   4800
aacatcaaat tcatcctgga tgcgaacttc atcatcagcg gcaccaccag cattggccag   4860
ttcgaattta tttgcgatga aaacgataac atccagccgt acttcatcaa attcaacacc   4920
ctggaaacca actataccct gtatgtgggc aaccgtcaga acatgattgt ggaaccgaac   4980
tatgatctgg atgatagcgg cgatattagc agcaccgtga ttaactttag ccagaaatat   5040
ctgtatggca ttgatagctg cgtgaacaaa gtggtgatta gcccgaacat ttataccgat   5100
gaaattaaca ttaccccggt gtatgaaacc aacaacacct atccggaagt gattgtgctg   5160
gatgcgaact atattaacga aaaaattaac gtgaacatta acgatctgag cattcgttat   5220
gtgtggagca acgatggcaa cgattttatt ctgatgagca ccagcgaaga aaacaaagtg   5280
agccaggtga aaattcgttt tgtgaacgtg tttaaagata aaccctggc gaacaaactg   5340
agctttaact ttagcgataa acaggatgtg cctgtgagcg aaattattct gagctttacc   5400
ccgagctatt atgaagatgg cctgattggc tatgatctgg gcctggttag cctgtataac   5460
gaaaaatttt atattaacaa ctttggcatg atggttagcg gcctgattta tattaacgat   5520
agcctgtatt attttaaacc gccggtgaac aacctgatta ccggctttgt gaccgtgggc   5580
gatgataaat attattttaa cccgattaac ggcggcgcgg cgagcattgg cgaaaccatt   5640
attgatgata aaaactatta ttttaaccag agcggcgtgc tgcagaccgg cgtgtttagc   5700
accgaagatg gctttaaata ttttgcgccg gcgaacaccc tggatgaaaa cctggaaggc   5760
gaagcgatcg atttcaccgg caaactgatc atcgatgaaa acatctacta cttcgatgat   5820
aactaccgtg gcgcggtgga atggaaagaa ctggatggcg aaatgcatta ttttagcccg   5880
gaaaccggca aagcgtttaa aggcctgaac cagattggcg attataaata ttattttaac   5940
agcgatggcg tgatgcagaa aggctttgtg agcattaacg ataacaaaca ttattttgat   6000
gatagcggcg tgatgaaagt gggctatacc gaaattgatg gcaaacattt ttattttgcg   6060
gaaaacggcg aaatgcagat tggcgtgttt aatacggaag acggttttaa atattttgcg   6120
catcataacg aagatctggg caacgaagaa ggcgaagaaa tcagctacag cggcattctg   6180
```

aactttaaca acaaaattta ttacttcgat gatagcttta ccgcggtggt gggctggaaa 6240
gatctggaag atggcagcaa atattatttt gatgaagata ccgcggaagc gtatattggc 6300
ctgagcctga ttaacgatgg ccagtattat tttaacgatg atggcattat gcaagtgggc 6360
tttgtgacca ttaacgataa agtgttttat tttagcgata gcggcattat tgaaagcggc 6420
gtgcagaaca ttgatgataa ctatttttat attgatgata acggcattgt gcagattggc 6480
gtgtttgata ccagcgatgg ctacaaatac ttcgccccgg cgaacaccgt gaacgataac 6540
atttatggcc aggcggtgga atatagcggc ctggtgcgtg tgggcgaaga tgtgtattat 6600
tttggcgaaa cctataccat tgaaaccggc tggatctacg atatggaaaa cgaaagcgat 6660
aaatactact tcaacccgga aaccaaaaaa gcgtgcaaag gcatcaacct gatcgatgat 6720
atcaaatact acttcgatga aaaaggcatc atgcgtaccg gcctgattag ctttgaaaac 6780
aacaattact acttcaacga aaatggtgaa atgcagttcg gctacatcaa catcgaagat 6840
aaaatgtttt attttggcga agatggcgtg atgcaaatcg gcgtgtttaa caccccggac 6900
ggtttcaaat attttgcgca tcaaaatacc ctggatgaaa actttgaagg cgaaagcatt 6960
aactataccg gctggctgga tctggatgaa aaacgttatt attttaccga tgaatatatt 7020
gcggcgaccg gcagcgtgat tattgatggc gaagaatatt attttgatcc ggataccgcg 7080
cagctggtga ttagcgaata a 7101

<210> SEQ ID NO 11
<211> LENGTH: 7121
<212> TYPE: DNA
<213> ORGANISM: Clostridium difficile
<220> FEATURE:
<221> NAME/KEY: gene
<222> LOCATION: (11)..(7111)

<400> SEQUENCE: 11
cggcagccat atgagcctgg tgaaccgtaa acagctggaa aaaatggcga atgtgcgttt 60
tcgcgttcag gaagatgaat acgttgcgat tctggatgcc ctggaagaat atcataacat 120
gagcgaaaat accgtggttg aaaaatacct gaaactgaaa gatatcaaca gtctgaccga 180
tatctacatc gatacgtaca aaaaatctgg ccgcaacaaa gccctgaaaa aattcaaaga 240
atacctggtg accgaagttc tggaactgaa aaacaataac ctgacgccgg tggagaaaaa 300
cctgcacttt gtttggatcg gcggtcagat caacgatacc gcaatcaatt acatcaacca 360
gtggaaagat gtgaactctg attacaacgt gaacgtgttt tatgatagta atgcgttcct 420
gattaacacc ctgaagaaaa ccatcgttga aagcgccacg aacgataccc tggaatcttt 480
ccgtgaaaac ctgaatgatc cgcgcttcga ttacaacaaa ttctaccgta aacgcatgga 540
aatcatctac gataaacaga aaaacttcat caactactac aaaacccagc gtgaagaaaa 600
cccggatctg atcatcgatg atatcgtgaa aatctacctg agtaacgaat acagcaaaga 660
tatcgatgaa ctgaacagct atatcgaaga atctctgaat aaagtgaccg aaaactctgg 720
caatgatgtt cgcaactttg aagaattcaa aggcggtgaa agttttaaac tgtacgaaca 780
ggaactggtg gaacgttgga atctggcggc cgcaagtgat atcctgcgca ttagcgcgct 840
gaaagaagtg ggcggtgttt atctggatgt tgatatgctg ccgggtattc agccggatct 900
gttcgaaagc atcgaaaaac cgagctctgt gaccgttgat ttttgggaaa tggtgaaact 960
ggaagcaatc atgaaataca aagaatacat cccgggctat acgagcgaac acttcgatat 1020
gctggatgaa gaagtgcaga gtagctttga atctgttctg gcgagtaaaa gcgataaaag 1080

-continued

```
tgaaatttc tctagtctgg gtgatatgga agcgagcccg ctggaagtta aaatcgcctt   1140
caactctaaa ggcatcatca accagggtct gatcagtgtg aaagattctt actgcagtaa   1200
cctgatcgtt aaacagatcg aaaaccgtta caaaatcctg aataactctc tgaacccggc   1260
cattagtgaa gataacgatt ttaataccac gaccaatgca ttcatcgata gcattatggc   1320
cgaagcaaac gcggataatg gccgttttat gatggaactg ggtaaatatc tgcgcgtggg   1380
ctttttcccg gatgttaaaa cgaccattaa cctgagcggt ccggaagcgt acgcggcagc   1440
atatcaggat ctgctgatgt tcaaagaagg cagtatgaat atccacctga ttgaagcgga   1500
tctgcgtaac ttcgaaatca gcaaaaccaa catctctcag agtacggaac aggaaatggc   1560
cagcctgtgg tctttcgatg atgcccgcgc aaaagcgcag ttcgaagaat acaagaaaaa   1620
ctacttcgaa ggcagcctgg gtgaagatga taatctggat ttttctcaga acaccgtggt   1680
tgataaagaa tacctgctgg aaaaaatcag ctctctggcg cgtagtagcg aacgcggtta   1740
catccattat attgtgcagc tgcagggcga taaaatcagc tacgaagcgg cctgcaatct   1800
gtttgcaaaa accccgtatg atagtgttct gttccagaaa aacattgaag atagcgaaat   1860
cgcgtattac tataatccgg gcgatggtga aatccaggaa atcgataaat acaaaatccc   1920
gagtatcatc agcgatcgcc cgaaaattaa actgaccttt atcggccacg gtaaagatga   1980
atttaacacg gatattttcg cgggcctgga tgtggatagc ctgtctaccg aaatcgaaac   2040
ggcaattgat ctggcgaaag aagatatctc tccgaaaagt atcgaaatca atctgctggg   2100
ttgtaacatg tttagttaca gcgtgaatgt tgaagaaacc tatccgggca aactgctgct   2160
gcgtgtgaaa gataaagttt ctgaactgat gccgtctatc agtcaggatt ctattatcgt   2220
gagtgccaat cagtatgaag ttcgcattaa cagcgaaggt cgtcgcgaac tgctggatca   2280
tagcggcgaa tggatcaaca aagaagaatc tatcatcaaa gatatctcta gtaaagaata   2340
catcagcttc aacccgaaag aaaacaaaat catcgtgaaa agtaaaaacc tgccggaact   2400
gagcaccctg ctgcaggaaa tccgtaataa cagcaatagc tctgatattg aactggaaga   2460
aaaagtgatg ctggcagaat gcgaaatcaa cgttatctct aacatcgata cccaggtggt   2520
tgaaggtcgc attgaagaag cgaaaagtct gacgagcgat tctatcaact acatcaaaaa   2580
cgaattcaaa ctgattgaaa gtatcagcga tgcgctgtat gatctgaaac agcagaacga   2640
actggaagaa agccacttta tttctttcga agatatcctg gaaaccgatg aaggtttctc   2700
tatccgtttc atcgataaag aaaccggcga aagtattttt gtggaaacgg aaaaagcaat   2760
cttcagcgaa tacgcgaacc atatcaccga agaaatctct aaaatcaaag gtaccatctt   2820
tgatacggtg aacggcaaac tggtgaaaaa agttaatctg gatgccaccc acgaagttaa   2880
cacgctgaat gcagcgtttt tcatccagag cctgattgaa tacaacagta gcaaagaatc   2940
tctgagtaat ctgagcgtgg caatgaaagt gcaggtttat gcgcagctgt tttctaccgg   3000
cctgaacacg attaccgatg ccgcaaaagt ggttgaactg gttagcaccg ccctggatga   3060
aacgattgat ctgctgccga ccctgagcga aggtctgccg gtgatcgcaa cgattatcga   3120
tggcgtttct ctgggtgcgg ccattaaaga actgagcgaa acctctgatc cgctgctgcg   3180
tcaggaaatt gaagccaaaa ttggcatcat ggcagtgaat ctgaccgcag cgacgaccgc   3240
aattatcacg tctagtctgg gcattgcgag tggttttagc atcctgctgg tgccgctggc   3300
aggtatcagt gcaggtattc cgagcctggt taataacgaa ctgatcctgc gcgataaagc   3360
gaccaaagtg gttgattact tctctcatat cagtctggcg gaaagcgaag gtgcctttac   3420
gtctctggat gataaaatta tgatgccgca ggatgatctg gtgatcagtg aaatcgattt   3480
```

-continued

```
caacaacaac agcattaccc tgggtaaatg tgaaatctgg cgtatggaag gcggtagcgg   3540

ccatacggtt accgatgata tcgatcactt tttcagcgcc ccgtctatta cctaccgcga   3600

accgcacctg agcatctatg atgtgctgga agttcagaaa gaagaactgg atctgtctaa   3660

agatctgatg gtgctgccga acgcgccgaa tcgtgttttc gcctgggaaa cgggttggac   3720

cccgggtctg cgtagcctgg aaaacgatgg taccaaactg ctggatcgta ttcgcgataa   3780

ttacgaaggc gaattttact ggcgttattt tgcgttcatt gccgatgcac tgatcacgac   3840

cctgaaaccg cgttatgaag ataccaacat tcgcatcaat ctggatagta acacgcgtag   3900

cttcatcgtg ccggttatta cgaccgaata tattcgcgaa aaactgagct actcttttta   3960

tggcagcggc ggtacctacg ccctgagtct gagccagtac aacatgaaca tcaacatcga   4020

actgaacgaa aacgatacct gggtgattga tgttgataac gtggttcgcg atgtgacgat   4080

cgaaagcgat aaaatcaaaa aaggtgatct gatcgaaaac atcctgagta aactgagcat   4140

cgaagataac aaaatcatcc tggataacca tgaaatcaac tttagcggta ccctgaacgg   4200

cggtaatggc tttgtttctc tgacgttcag tatcctggaa ggtattaatg cggtgatcga   4260

agttgatctg ctgtctaaaa gttataaagt gctgattagc ggcgaactga aaaccctgat   4320

ggccaatagc aactctgttc agcagaaaat tgattacatc ggtctgaata gtgaactgca   4380

gaaaaacatc ccgtatagct ttatggatga taaaggcaaa gaaaacggtt tcatcaactg   4440

cagcaccaaa gaaggcctgt ttgtgtctga actgagtgat gtggttctga tctctaaagt   4500

ttacatggat aacagtaaac cgctgtttgg ctattgtagc aatgatctga aagatgtgaa   4560

agttatcacc aaagatgatg tgatcatcct gacgggttac tacctgaaag atgatatcaa   4620

aatcagtctg agcttcacca ttcaggatga aaatacgatc aaactgaacg gtgtgtatct   4680

ggatgaaaac ggcgttgcgg aaatcctgaa attcatgaac aaaaaaggca gcacgaacac   4740

ctctgatagt ctgatgagct tcctggaatc tatgaacatc aaatctatct tcatcaatag   4800

cctgcagtct aacaccaaac tgatcctgga tacgaatttc atcatcagtg gcacgaccag   4860

cattggccag ttcgaattca tctgcgataa agataacaac atccagccgt acttcatcaa   4920

attcaacacg ctggaaacca aatacacgct gtatgtgggt aaccgtcaga atatgattgt   4980

tgaaccgaac tatgatctgg atgatagtgg tgatattagc tctaccgtga tcaattttag   5040

ccagaaatac ctgtatggca tcgattcttg tgtgaacaaa gttatcatca gtccgaacat   5100

ctacaccgat gaaatcaaca tcacgccgat ctacgaagcg aacaatacct atccggaagt   5160

gattgttctg gatacgaact acatctctga aaaaatcaac atcaacatca acgatctgag   5220

tattcgttat gtgtggtcta acgatggcag tgattttatc ctgatgagca ccgatgaaga   5280

aaacaaagtg tctcaggtta aaatccgctt caccaacgtt ttcaagggta acacgatcag   5340

cgataaaatc tctttcaact tcagtgataa acaggatgtg agcatcaaca aagttatctc   5400

tacgttcacc ccgagttact atgtggaagg tctgctgaac tacgatctgg gcctgattag   5460

cctgtacaac gaaaaattct acatcaacaa cttcggcatg atggtgtctg gtctggttta   5520

catcaacgat agcctgtact acttcaaacc gccgattaaa aatctgatca ccggcttcac   5580

gaccatcggt gatgataaat actacttcaa cccggataat ggcggtgccg caagcgtggg   5640

tgaaaccatc atcgatggca aaaactacta cttcagccag aacggcgtgc tgcagaccgg   5700

tgtgtttagc acggaagatg gctttaaata tttcgcgccg gccgataccc tggatgaaaa   5760

tctggaaggt gaagcgatcg atttcaccgg caaactgacg attgatgaaa acgtgtacta   5820

cttcggtgat aactatcgtg cggccattga atggcagacc ctggatgatg aagtttacta   5880
```

-continued

```
cttctctacg gataccggcc gcgccttcaa aggtctgaac cagatcggcg atgataaatt   5940

ctacttcaac agcgatggta tcatgcagaa aggcttcgtg aacatcaacg ataaaacctt   6000

ctacttcgat gatagcggtg ttatgaaatc tggctatacg gaaatcgatg gcaaatactt   6060

ttatttcgcg gaaaacggtg aaatgcagat tggcgtgttt aataccgccg atggttttaa   6120

atacttcgca catcacgatg aagatctggg caacgaagaa ggtgaagccc tgagctactc   6180

tggcattctg aacttcaaca acaaaatcta ctacttcgat gatagtttca ccgcagtggt   6240

tggttggaaa gatctggaag atggcagcaa atactatttt gatgaagata cggcagaagc   6300

gtatatcggt atctctatca tcaacgatgg caaatactac ttcaacgata gtggtatcat   6360

gcagatcggc ttcgtgacca tcaacaacga agtgttttat ttcagtgata gcggtatcgt   6420

ggaaagcggc atgcagaaca tcgatgacaa ctacttctac atcgatgaaa acggtctggt   6480

gcagattggc gttttcgata cctctgatgg ttacaaatac ttcgccccgg caaatacggt   6540

gaacgataat atctacggcc aggcagttga atatagcggt ctggtgcgtg ttggcgaaga   6600

tgtgtactat tttggtgaaa cgtacaccat tgaaaccggc tggatctatg atatggaaaa   6660

cgaaagcgat aaatactact tcgatccgga aacgaaaaaa gcgtacaaag gcatcaacgt   6720

tatcgatgat atcaaatact acttcgatga aaacggtatt atgcgcaccg gcctgatcac   6780

gttcgaagat aaccattact acttcaacga agatggtatc atgcagtacg gctacctgaa   6840

catcgaagac aaaacgttct acttctctga agacggtatc atgcagattg gcgtgttcaa   6900

taccccggat ggttttaaat atttcgccca ccagaatacg ctggatgaaa acttcgaagg   6960

tgaaagcatc aactacaccg gctggctgga tctggatgaa aaacgctact atttcaccga   7020

tgaatatatc gcagcgacgg gtagtgtgat tatcgatggc gaagaatact attttgatcc   7080

ggataccgca cagctggtta ttagcgaata aggatccggc t                        7121
```

<210> SEQ ID NO 12
<211> LENGTH: 2366
<212> TYPE: PRT
<213> ORGANISM: Clostridium difficile
<220> FEATURE:
<221> NAME/KEY: PEPTIDE
<222> LOCATION: (1)..(2366)

<400> SEQUENCE: 12

```
Met Ser Leu Val Asn Arg Lys Gln Leu Glu Lys Met Ala Asn Val Arg
1               5                   10                  15

Phe Arg Val Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Ala Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140
```

-continued

```
Ile Val Glu Ser Ala Thr Asn Asp Thr Leu Glu Ser Phe Arg Glu Asn
145                 150                 155                 160

Leu Asn Asp Pro Arg Phe Asp Tyr Asn Lys Phe Tyr Arg Lys Arg Met
                165                 170                 175

Glu Ile Ile Tyr Asp Lys Gln Lys Asn Phe Ile Asn Tyr Tyr Lys Thr
            180                 185                 190

Gln Arg Glu Glu Asn Pro Asp Leu Ile Ile Asp Asp Ile Val Lys Ile
        195                 200                 205

Tyr Leu Ser Asn Glu Tyr Ser Lys Asp Ile Asp Glu Leu Asn Ser Tyr
    210                 215                 220

Ile Glu Glu Ser Leu Asn Lys Val Thr Glu Asn Ser Gly Asn Asp Val
225                 230                 235                 240

Arg Asn Phe Glu Glu Phe Lys Gly Gly Glu Ser Phe Lys Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Val Gly Gly Val Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Val Lys Leu Glu Ala Ile
305                 310                 315                 320

Met Lys Tyr Lys Glu Tyr Ile Pro Gly Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Ala Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Lys Asn Tyr Phe Glu Gly Ser Leu Gly
    530                 535                 540

Glu Asp Asp Asn Leu Asp Phe Ser Gln Asn Thr Val Val Asp Lys Glu
545                 550                 555                 560

Tyr Leu Leu Glu Lys Ile Ser Ser Leu Ala Arg Ser Ser Glu Arg Gly
                565                 570                 575
```

```
Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Leu Asp Val Asp Ser Leu Ser
            660                 665                 670

Thr Glu Ile Glu Thr Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
    690                 695                 700

Val Asn Val Glu Glu Thr Tyr Pro Gly Lys Leu Leu Leu Arg Val Lys
705                 710                 715                 720

Asp Lys Val Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser Ile
        755                 760                 765

Ile Lys Asp Ile Ser Ser Lys Glu Tyr Ile Ser Phe Asn Pro Lys Glu
    770                 775                 780

Asn Lys Ile Ile Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Ala Glu Cys Glu Ile Asn Val Ile Ser Asn Ile
            820                 825                 830

Asp Thr Gln Val Val Glu Gly Arg Ile Glu Glu Ala Lys Ser Leu Thr
        835                 840                 845

Ser Asp Ser Ile Asn Tyr Ile Lys Asn Glu Phe Lys Leu Ile Glu Ser
    850                 855                 860

Ile Ser Asp Ala Leu Tyr Asp Leu Lys Gln Gln Asn Glu Leu Glu Glu
865                 870                 875                 880

Ser His Phe Ile Ser Phe Glu Asp Ile Leu Glu Thr Asp Glu Gly Phe
                885                 890                 895

Ser Ile Arg Phe Ile Asp Lys Glu Thr Gly Glu Ser Ile Phe Val Glu
            900                 905                 910

Thr Glu Lys Ala Ile Phe Ser Glu Tyr Ala Asn His Ile Thr Glu Glu
        915                 920                 925

Ile Ser Lys Ile Lys Gly Thr Ile Phe Asp Thr Val Asn Gly Lys Leu
    930                 935                 940

Val Lys Lys Val Asn Leu Asp Ala Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr  Ile Thr Asp Ala Ala  Lys Val Val
```

-continued

```
        995                 1000                1005

Glu Leu  Val Ser Thr Ala Leu  Asp Glu Thr Ile Asp  Leu Leu Pro
    1010                 1015                 1020

Thr Leu  Ser Glu Gly Leu Pro  Val Ile Ala Thr Ile  Ile Asp Gly
    1025                 1030                 1035

Val Ser  Leu Gly Ala Ala Ile  Lys Glu Leu Ser Glu  Thr Ser Asp
    1040                 1045                 1050

Pro Leu  Leu Arg Gln Glu Ile  Glu Ala Lys Ile Gly  Ile Met Ala
    1055                 1060                 1065

Val Asn  Leu Thr Ala Ala Thr  Thr Ala Ile Ile Thr  Ser Ser Leu
    1070                 1075                 1080

Gly Ile  Ala Ser Gly Phe Ser  Ile Leu Leu Val Pro  Leu Ala Gly
    1085                 1090                 1095

Ile Ser  Ala Gly Ile Pro Ser  Leu Val Asn Asn Glu  Leu Ile Leu
    1100                 1105                 1110

Arg Asp  Lys Ala Thr Lys Val  Val Asp Tyr Phe Ser  His Ile Ser
    1115                 1120                 1125

Leu Ala  Glu Ser Glu Gly Ala  Phe Thr Ser Leu Asp  Asp Lys Ile
    1130                 1135                 1140

Met Met  Pro Gln Asp Asp Leu  Val Ile Ser Glu Ile  Asp Phe Asn
    1145                 1150                 1155

Asn Asn  Ser Ile Thr Leu Gly  Lys Cys Glu Ile Trp  Arg Met Glu
    1160                 1165                 1170

Gly Gly  Ser Gly His Thr Val  Thr Asp Asp Ile Asp  His Phe Phe
    1175                 1180                 1185

Ser Ala  Pro Ser Ile Thr Tyr  Arg Glu Pro His Leu  Ser Ile Tyr
    1190                 1195                 1200

Asp Val  Leu Glu Val Gln Lys  Glu Glu Leu Asp Leu  Ser Lys Asp
    1205                 1210                 1215

Leu Met  Val Leu Pro Asn Ala  Pro Asn Arg Val Phe  Ala Trp Glu
    1220                 1225                 1230

Thr Gly  Trp Thr Pro Gly Leu  Arg Ser Leu Glu Asn  Asp Gly Thr
    1235                 1240                 1245

Lys Leu  Leu Asp Arg Ile Arg  Asp Asn Tyr Glu Gly  Glu Phe Tyr
    1250                 1255                 1260

Trp Arg  Tyr Phe Ala Phe Ile  Ala Asp Ala Leu Ile  Thr Thr Leu
    1265                 1270                 1275

Lys Pro  Arg Tyr Glu Asp Thr  Asn Ile Arg Ile Asn  Leu Asp Ser
    1280                 1285                 1290

Asn Thr  Arg Ser Phe Ile Val  Pro Val Ile Thr Thr  Glu Tyr Ile
    1295                 1300                 1305

Arg Glu  Lys Leu Ser Tyr Ser  Phe Tyr Gly Ser Gly  Gly Thr Tyr
    1310                 1315                 1320

Ala Leu  Ser Leu Ser Gln Tyr  Asn Met Asn Ile Asn  Ile Glu Leu
    1325                 1330                 1335

Asn Glu  Asn Asp Thr Trp Val  Ile Asp Val Asp Asn  Val Val Arg
    1340                 1345                 1350

Asp Val  Thr Ile Glu Ser Asp  Lys Ile Lys Lys Gly  Asp Leu Ile
    1355                 1360                 1365

Glu Asn  Ile Leu Ser Lys Leu  Ser Ile Glu Asp Asn  Lys Ile Ile
    1370                 1375                 1380

Leu Asp  Asn His Glu Ile Asn  Phe Ser Gly Thr Leu  Asn Gly Gly
    1385                 1390                 1395
```

-continued

```
Asn Gly Phe Val Ser Leu Thr Phe Ser Ile Leu Glu Gly Ile Asn
    1400                1405                1410

Ala Val Ile Glu Val Asp Leu Leu Ser Lys Ser Tyr Lys Val Leu
    1415                1420                1425

Ile Ser Gly Glu Leu Lys Thr Leu Met Ala Asn Ser Asn Ser Val
    1430                1435                1440

Gln Gln Lys Ile Asp Tyr Ile Gly Leu Asn Ser Glu Leu Gln Lys
    1445                1450                1455

Asn Ile Pro Tyr Ser Phe Met Asp Asp Lys Gly Lys Glu Asn Gly
    1460                1465                1470

Phe Ile Asn Cys Ser Thr Lys Glu Gly Leu Phe Val Ser Glu Leu
    1475                1480                1485

Ser Asp Val Val Leu Ile Ser Lys Val Tyr Met Asp Asn Ser Lys
    1490                1495                1500

Pro Leu Phe Gly Tyr Cys Ser Asn Asp Leu Lys Asp Val Lys Val
    1505                1510                1515

Ile Thr Lys Asp Asp Val Ile Ile Leu Thr Gly Tyr Tyr Leu Lys
    1520                1525                1530

Asp Asp Ile Lys Ile Ser Leu Ser Phe Thr Ile Gln Asp Glu Asn
    1535                1540                1545

Thr Ile Lys Leu Asn Gly Val Tyr Leu Asp Glu Asn Gly Val Ala
    1550                1555                1560

Glu Ile Leu Lys Phe Met Asn Lys Lys Gly Ser Thr Asn Thr Ser
    1565                1570                1575

Asp Ser Leu Met Ser Phe Leu Glu Ser Met Asn Ile Lys Ser Ile
    1580                1585                1590

Phe Ile Asn Ser Leu Gln Ser Asn Thr Lys Leu Ile Leu Asp Thr
    1595                1600                1605

Asn Phe Ile Ile Ser Gly Thr Thr Ser Ile Gly Gln Phe Glu Phe
    1610                1615                1620

Ile Cys Asp Lys Asp Asn Asn Ile Gln Pro Tyr Phe Ile Lys Phe
    1625                1630                1635

Asn Thr Leu Glu Thr Lys Tyr Thr Leu Tyr Val Gly Asn Arg Gln
    1640                1645                1650

Asn Met Ile Val Glu Pro Asn Tyr Asp Leu Asp Asp Ser Gly Asp
    1655                1660                1665

Ile Ser Ser Thr Val Ile Asn Phe Ser Gln Lys Tyr Leu Tyr Gly
    1670                1675                1680

Ile Asp Ser Cys Val Asn Lys Val Ile Ile Ser Pro Asn Ile Tyr
    1685                1690                1695

Thr Asp Glu Ile Asn Ile Thr Pro Ile Tyr Glu Ala Asn Asn Thr
    1700                1705                1710

Tyr Pro Glu Val Ile Val Leu Asp Thr Asn Tyr Ile Ser Glu Lys
    1715                1720                1725

Ile Asn Ile Asn Ile Asn Asp Leu Ser Ile Arg Tyr Val Trp Ser
    1730                1735                1740

Asn Asp Gly Ser Asp Phe Ile Leu Met Ser Thr Asp Glu Glu Asn
    1745                1750                1755

Lys Val Ser Gln Val Lys Ile Arg Phe Thr Asn Val Phe Lys Gly
    1760                1765                1770

Asn Thr Ile Ser Asp Lys Ile Ser Phe Asn Phe Ser Asp Lys Gln
    1775                1780                1785

Asp Val Ser Ile Asn Lys Val Ile Ser Thr Phe Thr Pro Ser Tyr
    1790                1795                1800
```

```
Tyr Val  Glu Gly Leu Leu Asn  Tyr Asp Leu Gly Leu  Ile Ser Leu
    1805                 1810                 1815

Tyr Asn  Glu Lys Phe Tyr Ile  Asn Asn Phe Gly Met  Met Val Ser
    1820                 1825                 1830

Gly Leu  Val Tyr Ile Asn Asp  Ser Leu Tyr Tyr Phe  Lys Pro Pro
    1835                 1840                 1845

Ile Lys  Asn Leu Ile Thr Gly  Phe Thr Thr Ile Gly  Asp Asp Lys
    1850                 1855                 1860

Tyr Tyr  Phe Asn Pro Asp Asn  Gly Gly Ala Ala Ser  Val Gly Glu
    1865                 1870                 1875

Thr Ile  Ile Asp Gly Lys Asn  Tyr Tyr Phe Ser Gln  Asn Gly Val
    1880                 1885                 1890

Leu Gln  Thr Gly Val Phe Ser  Thr Glu Asp Gly Phe  Lys Tyr Phe
    1895                 1900                 1905

Ala Pro  Ala Asp Thr Leu Asp  Glu Asn Leu Glu Gly  Glu Ala Ile
    1910                 1915                 1920

Asp Phe  Thr Gly Lys Leu Thr  Ile Asp Glu Asn Val  Tyr Tyr Phe
    1925                 1930                 1935

Gly Asp  Asn Tyr Arg Ala Ala  Ile Glu Trp Gln Thr  Leu Asp Asp
    1940                 1945                 1950

Glu Val  Tyr Tyr Phe Ser Thr  Asp Thr Gly Arg Ala  Phe Lys Gly
    1955                 1960                 1965

Leu Asn  Gln Ile Gly Asp Asp  Lys Phe Tyr Phe Asn  Ser Asp Gly
    1970                 1975                 1980

Ile Met  Gln Lys Gly Phe Val  Asn Ile Asn Asp Lys  Thr Phe Tyr
    1985                 1990                 1995

Phe Asp  Asp Ser Gly Val Met  Lys Ser Gly Tyr Thr  Glu Ile Asp
    2000                 2005                 2010

Gly Lys  Tyr Phe Tyr Phe Ala  Glu Asn Gly Glu Met  Gln Ile Gly
    2015                 2020                 2025

Val Phe  Asn Thr Ala Asp Gly  Phe Lys Tyr Phe Ala  His His Asp
    2030                 2035                 2040

Glu Asp  Leu Gly Asn Glu Glu  Gly Glu Ala Leu Ser  Tyr Ser Gly
    2045                 2050                 2055

Ile Leu  Asn Phe Asn Asn Lys  Ile Tyr Tyr Phe Asp  Asp Ser Phe
    2060                 2065                 2070

Thr Ala  Val Val Gly Trp Lys  Asp Leu Glu Asp Gly  Ser Lys Tyr
    2075                 2080                 2085

Tyr Phe  Asp Glu Asp Thr Ala  Glu Ala Tyr Ile Gly  Ile Ser Ile
    2090                 2095                 2100

Ile Asn  Asp Gly Lys Tyr Tyr  Phe Asn Asp Ser Gly  Ile Met Gln
    2105                 2110                 2115

Ile Gly  Phe Val Thr Ile Asn  Asn Glu Val Phe Tyr  Phe Ser Asp
    2120                 2125                 2130

Ser Gly  Ile Val Glu Ser Gly  Met Gln Asn Ile Asp  Asp Asn Tyr
    2135                 2140                 2145

Phe Tyr  Ile Asp Glu Asn Gly  Leu Val Gln Ile Gly  Val Phe Asp
    2150                 2155                 2160

Thr Ser  Asp Gly Tyr Lys Tyr  Phe Ala Pro Ala Asn  Thr Val Asn
    2165                 2170                 2175

Asp Asn  Ile Tyr Gly Gln Ala  Val Glu Tyr Ser Gly  Leu Val Arg
    2180                 2185                 2190

Val Gly  Glu Asp Val Tyr Tyr  Phe Gly Glu Thr Tyr  Thr Ile Glu
```

```
    2195                2200                2205

Thr Gly  Trp Ile Tyr Asp Met  Glu Asn Glu Ser Asp  Lys Tyr Tyr
    2210                2215                2220

Phe Asp  Pro Glu Thr Lys Lys  Ala Tyr Lys Gly Ile  Asn Val Ile
    2225                2230                2235

Asp Asp  Ile Lys Tyr Tyr Phe  Asp Glu Asn Gly Ile  Met Arg Thr
    2240                2245                2250

Gly Leu  Ile Thr Phe Glu Asp  Asn His Tyr Tyr Phe  Asn Glu Asp
    2255                2260                2265

Gly Ile  Met Gln Tyr Gly Tyr  Leu Asn Ile Glu Asp  Lys Thr Phe
    2270                2275                2280

Tyr Phe  Ser Glu Asp Gly Ile  Met Gln Ile Gly Val  Phe Asn Thr
    2285                2290                2295

Pro Asp  Gly Phe Lys Tyr Phe  Ala His Gln Asn Thr  Leu Asp Glu
    2300                2305                2310

Asn Phe  Glu Gly Glu Ser Ile  Asn Tyr Thr Gly Trp  Leu Asp Leu
    2315                2320                2325

Asp Glu  Lys Arg Tyr Tyr Phe  Thr Asp Glu Tyr Ile  Ala Ala Thr
    2330                2335                2340

Gly Ser  Val Ile Ile Asp Gly  Glu Glu Tyr Tyr Phe  Asp Pro Asp
    2345                2350                2355

Thr Ala  Gln Leu Val Ile Ser  Glu
    2360                2365


<210> SEQ ID NO 13
<211> LENGTH: 2366
<212> TYPE: PRT
<213> ORGANISM: Clostridium difficile
<220> FEATURE:
<221> NAME/KEY: PEPTIDE
<222> LOCATION: (1)..(2366)

<400> SEQUENCE: 13

Met Ser Leu Val Asn Arg Lys Gln Leu Glu Lys Met Ala Asn Val Arg
1               5                   10                  15

Phe Arg Val Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Ile Val Glu Ser Ala Thr Asn Asp Thr Leu Glu Ser Phe Arg Glu Asn
145                 150                 155                 160

Leu Asn Asp Pro Arg Phe Asp Tyr Asn Lys Phe Tyr Arg Lys Arg Met
                165                 170                 175

Glu Ile Ile Tyr Asp Lys Gln Lys Asn Phe Ile Asn Tyr Tyr Lys Thr
```

```
            180                 185                 190

Gln Arg Glu Glu Asn Pro Asp Leu Ile Ile Asp Asp Ile Val Lys Ile
        195                 200                 205

Tyr Leu Ser Asn Glu Tyr Ser Lys Asp Ile Asp Glu Leu Asn Ser Tyr
    210                 215                 220

Ile Glu Glu Ser Leu Asn Lys Val Thr Glu Asn Ser Gly Asn Asp Val
225                 230                 235                 240

Arg Asn Phe Glu Glu Phe Lys Gly Gly Glu Ser Phe Lys Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Val Gly Gly Val Tyr Leu Gly Val Gly
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Val Lys Leu Glu Ala Ile
305                 310                 315                 320

Met Lys Tyr Lys Glu Tyr Ile Pro Gly Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Ala Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Lys Asn Tyr Phe Glu Gly Ser Leu Gly
    530                 535                 540

Glu Asp Asp Asn Leu Asp Phe Ser Gln Asn Thr Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605
```

```
Gln Lys Asn Ile Glu Asp Ser Glu Ile Ala Tyr Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Leu Asp Val Asp Ser Leu Ser
            660                 665                 670

Thr Glu Ile Glu Thr Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
    690                 695                 700

Val Asn Val Glu Glu Thr Tyr Pro Gly Lys Leu Leu Leu Arg Val Lys
705                 710                 715                 720

Asp Lys Val Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser Ile
        755                 760                 765

Ile Lys Asp Ile Ser Ser Lys Glu Tyr Ile Ser Phe Asn Pro Lys Glu
    770                 775                 780

Asn Lys Ile Ile Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Ala Glu Cys Glu Ile Asn Val Ile Ser Asn Ile
            820                 825                 830

Asp Thr Gln Val Val Glu Gly Arg Ile Glu Glu Ala Lys Ser Leu Thr
        835                 840                 845

Ser Asp Ser Ile Asn Tyr Ile Lys Asn Glu Phe Lys Leu Ile Glu Ser
    850                 855                 860

Ile Ser Asp Ala Leu Tyr Asp Leu Lys Gln Gln Asn Glu Leu Glu Glu
865                 870                 875                 880

Ser His Phe Ile Ser Phe Glu Asp Ile Leu Glu Thr Asp Glu Gly Phe
                885                 890                 895

Ser Ile Arg Phe Ile Asp Lys Glu Thr Gly Glu Ser Ile Phe Val Glu
            900                 905                 910

Thr Glu Lys Ala Ile Phe Ser Glu Tyr Ala Asn His Ile Thr Glu Glu
        915                 920                 925

Ile Ser Lys Ile Lys Gly Thr Ile Phe Asp Thr Val Asn Gly Lys Leu
    930                 935                 940

Val Lys Lys Val Asn Leu Asp Ala Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr  Ile Thr Asp Ala Ala  Lys Val Val
        995                 1000                1005

Glu Leu  Val Ser Thr Ala Leu  Asp Glu Thr Ile Asp  Leu Leu Pro
    1010                 1015                 1020

Thr Leu  Ser Glu Gly Leu Pro  Val Ile Ala Thr Ile  Ile Asp Gly
    1025                 1030                 1035
```

-continued

```
Val Ser  Leu Gly Ala Ala Ile  Lys Glu Leu Ser Glu  Thr Ser Asp
    1040                 1045                 1050

Pro Leu  Leu Arg Gln Glu Ile  Glu Ala Lys Ile Gly  Ile Met Ala
    1055                 1060                 1065

Val Asn  Leu Thr Ala Ala Thr  Thr Ala Ile Ile Thr  Ser Ser Leu
    1070                 1075                 1080

Gly Ile  Ala Ser Gly Phe Ser  Ile Leu Leu Val Pro  Leu Ala Gly
    1085                 1090                 1095

Ile Ser  Ala Gly Ile Pro Ser  Leu Val Asn Asn Glu  Leu Ile Leu
    1100                 1105                 1110

Arg Asp  Lys Ala Thr Lys Val  Val Asp Tyr Phe Ser  His Ile Ser
    1115                 1120                 1125

Leu Ala  Glu Ser Glu Gly Ala  Phe Thr Ser Leu Asp  Asp Lys Ile
    1130                 1135                 1140

Met Met  Pro Gln Asp Asp Leu  Val Ile Ser Glu Ile  Asp Phe Asn
    1145                 1150                 1155

Asn Asn  Ser Ile Thr Leu Gly  Lys Cys Glu Ile Trp  Arg Met Glu
    1160                 1165                 1170

Gly Gly  Ser Gly His Thr Val  Thr Asp Asp Ile Asp  His Phe Phe
    1175                 1180                 1185

Ser Ala  Pro Ser Ile Thr Tyr  Arg Glu Pro His Leu  Ser Ile Tyr
    1190                 1195                 1200

Asp Val  Leu Glu Val Gln Lys  Glu Glu Leu Asp Leu  Ser Lys Asp
    1205                 1210                 1215

Leu Met  Val Leu Pro Asn Ala  Pro Asn Arg Val Phe  Ala Trp Glu
    1220                 1225                 1230

Thr Gly  Trp Thr Pro Gly Leu  Arg Ser Leu Glu Asn  Asp Gly Thr
    1235                 1240                 1245

Lys Leu  Leu Asp Arg Ile Arg  Asp Asn Tyr Glu Gly  Glu Phe Tyr
    1250                 1255                 1260

Trp Arg  Tyr Phe Ala Phe Ile  Ala Asp Ala Leu Ile  Thr Thr Leu
    1265                 1270                 1275

Lys Pro  Arg Tyr Glu Asp Thr  Asn Ile Arg Ile Asn  Leu Asp Ser
    1280                 1285                 1290

Asn Thr  Arg Ser Phe Ile Val  Pro Val Ile Thr Thr  Glu Tyr Ile
    1295                 1300                 1305

Arg Glu  Lys Leu Ser Tyr Ser  Phe Tyr Gly Ser Gly  Gly Thr Tyr
    1310                 1315                 1320

Ala Leu  Ser Leu Ser Gln Tyr  Asn Met Asn Ile Asn  Ile Glu Leu
    1325                 1330                 1335

Asn Glu  Asn Asp Thr Trp Val  Ile Asp Val Asp Asn  Val Val Arg
    1340                 1345                 1350

Asp Val  Thr Ile Glu Ser Asp  Lys Ile Lys Lys Gly  Asp Leu Ile
    1355                 1360                 1365

Glu Asn  Ile Leu Ser Lys Leu  Ser Ile Glu Asp Asn  Lys Ile Ile
    1370                 1375                 1380

Leu Asp  Asn His Glu Ile Asn  Phe Ser Gly Thr Leu  Asn Gly Gly
    1385                 1390                 1395

Asn Gly  Phe Val Ser Leu Thr  Phe Ser Ile Leu Glu  Gly Ile Asn
    1400                 1405                 1410

Ala Val  Ile Glu Val Asp Leu  Leu Ser Lys Ser Tyr  Lys Val Leu
    1415                 1420                 1425

Ile Ser  Gly Glu Leu Lys Thr  Leu Met Ala Asn Ser  Asn Ser Val
```

-continued

```
    1430                1435                1440

Gln Gln  Lys Ile Asp Tyr Ile  Gly Leu Asn Ser Glu  Leu Gln Lys
    1445                1450                1455

Asn Ile  Pro Tyr Ser Phe Met  Asp Asp Lys Gly Lys  Glu Asn Gly
    1460                1465                1470

Phe Ile  Asn Cys Ser Thr Lys  Glu Gly Leu Phe Val  Ser Glu Leu
    1475                1480                1485

Ser Asp  Val Val Leu Ile Ser  Lys Val Tyr Met Asp  Asn Ser Lys
    1490                1495                1500

Pro Leu  Phe Gly Tyr Cys Ser  Asn Asp Leu Lys Asp  Val Lys Val
    1505                1510                1515

Ile Thr  Lys Asp Asp Val Ile  Ile Leu Thr Gly Tyr  Tyr Leu Lys
    1520                1525                1530

Asp Asp  Ile Lys Ile Ser Leu  Ser Phe Thr Ile Gln  Asp Glu Asn
    1535                1540                1545

Thr Ile  Lys Leu Asn Gly Val  Tyr Leu Asp Glu Asn  Gly Val Ala
    1550                1555                1560

Glu Ile  Leu Lys Phe Met Asn  Lys Lys Gly Ser Thr  Asn Thr Ser
    1565                1570                1575

Asp Ser  Leu Met Ser Phe Leu  Glu Ser Met Asn Ile  Lys Ser Ile
    1580                1585                1590

Phe Ile  Asn Ser Leu Gln Ser  Asn Thr Lys Leu Ile  Leu Asp Thr
    1595                1600                1605

Asn Phe  Ile Ile Ser Gly Thr  Thr Ser Ile Gly Gln  Phe Glu Phe
    1610                1615                1620

Ile Cys  Asp Lys Asp Asn Asn  Ile Gln Pro Tyr Phe  Ile Lys Phe
    1625                1630                1635

Asn Thr  Leu Glu Thr Lys Tyr  Thr Leu Tyr Val Gly  Asn Arg Gln
    1640                1645                1650

Asn Met  Ile Val Glu Pro Asn  Tyr Asp Leu Asp Asp  Ser Gly Asp
    1655                1660                1665

Ile Ser  Ser Thr Val Ile Asn  Phe Ser Gln Lys Tyr  Leu Tyr Gly
    1670                1675                1680

Ile Asp  Ser Cys Val Asn Lys  Val Ile Ile Ser Pro  Asn Ile Tyr
    1685                1690                1695

Thr Asp  Glu Ile Asn Ile Thr  Pro Ile Tyr Glu Ala  Asn Asn Thr
    1700                1705                1710

Tyr Pro  Glu Val Ile Val Leu  Asp Thr Asn Tyr Ile  Ser Glu Lys
    1715                1720                1725

Ile Asn  Ile Asn Ile Asn Asp  Leu Ser Ile Arg Tyr  Val Trp Ser
    1730                1735                1740

Asn Asp  Gly Ser Asp Phe Ile  Leu Met Ser Thr Asp  Glu Glu Asn
    1745                1750                1755

Lys Val  Ser Gln Val Lys Ile  Arg Phe Thr Asn Val  Phe Lys Gly
    1760                1765                1770

Asn Thr  Ile Ser Asp Lys Ile  Ser Phe Asn Phe Ser  Asp Lys Gln
    1775                1780                1785

Asp Val  Ser Ile Asn Lys Val  Ile Ser Thr Phe Thr  Pro Ser Tyr
    1790                1795                1800

Tyr Val  Glu Gly Leu Leu Asn  Tyr Asp Leu Gly Leu  Ile Ser Leu
    1805                1810                1815

Tyr Asn  Glu Lys Phe Tyr Ile  Asn Asn Phe Gly Met  Met Val Ser
    1820                1825                1830
```

-continued

```
Gly Leu  Val Tyr Ile Asn Asp  Ser Leu Tyr Tyr Phe  Lys Pro Pro
    1835                 1840                 1845

Ile Lys  Asn Leu Ile Thr Gly  Phe Thr Thr Ile Gly  Asp Asp Lys
    1850                 1855                 1860

Tyr Tyr  Phe Asn Pro Asp Asn  Gly Gly Ala Ala Ser  Val Gly Glu
    1865                 1870                 1875

Thr Ile  Ile Asp Gly Lys Asn  Tyr Tyr Phe Ser Gln  Asn Gly Val
    1880                 1885                 1890

Leu Gln  Thr Gly Val Phe Ser  Thr Glu Asp Gly Phe  Lys Tyr Phe
    1895                 1900                 1905

Ala Pro  Ala Asp Thr Leu Asp  Glu Asn Leu Glu Gly  Glu Ala Ile
    1910                 1915                 1920

Asp Phe  Thr Gly Lys Leu Thr  Ile Asp Glu Asn Val  Tyr Tyr Phe
    1925                 1930                 1935

Gly Asp  Asn Tyr Arg Ala Ala  Ile Glu Trp Gln Thr  Leu Asp Asp
    1940                 1945                 1950

Glu Val  Tyr Tyr Phe Ser Thr  Asp Thr Gly Arg Ala  Phe Lys Gly
    1955                 1960                 1965

Leu Asn  Gln Ile Gly Asp Asp  Lys Phe Tyr Phe Asn  Ser Asp Gly
    1970                 1975                 1980

Ile Met  Gln Lys Gly Phe Val  Asn Ile Asn Asp Lys  Thr Phe Tyr
    1985                 1990                 1995

Phe Asp  Asp Ser Gly Val Met  Lys Ser Gly Tyr Thr  Glu Ile Asp
    2000                 2005                 2010

Gly Lys  Tyr Phe Tyr Phe Ala  Glu Asn Gly Glu Met  Gln Ile Gly
    2015                 2020                 2025

Val Phe  Asn Thr Ala Asp Gly  Phe Lys Tyr Phe Ala  His His Asp
    2030                 2035                 2040

Glu Asp  Leu Gly Asn Glu Glu  Gly Glu Ala Leu Ser  Tyr Ser Gly
    2045                 2050                 2055

Ile Leu  Asn Phe Asn Asn Lys  Ile Tyr Tyr Phe Asp  Asp Ser Phe
    2060                 2065                 2070

Thr Ala  Val Val Gly Trp Lys  Asp Leu Glu Asp Gly  Ser Lys Tyr
    2075                 2080                 2085

Tyr Phe  Asp Glu Asp Thr Ala  Glu Ala Tyr Ile Gly  Ile Ser Ile
    2090                 2095                 2100

Ile Asn  Asp Gly Lys Tyr Tyr  Phe Asn Asp Ser Gly  Ile Met Gln
    2105                 2110                 2115

Ile Gly  Phe Val Thr Ile Asn  Asn Glu Val Phe Tyr  Phe Ser Asp
    2120                 2125                 2130

Ser Gly  Ile Val Glu Ser Gly  Met Gln Asn Ile Asp  Asp Asn Tyr
    2135                 2140                 2145

Phe Tyr  Ile Asp Glu Asn Gly  Leu Val Gln Ile Gly  Val Phe Asp
    2150                 2155                 2160

Thr Ser  Asp Gly Tyr Lys Tyr  Phe Ala Pro Ala Asn  Thr Val Asn
    2165                 2170                 2175

Asp Asn  Ile Tyr Gly Gln Ala  Val Glu Tyr Ser Gly  Leu Val Arg
    2180                 2185                 2190

Val Gly  Glu Asp Val Tyr Tyr  Phe Gly Glu Thr Tyr  Thr Ile Glu
    2195                 2200                 2205

Thr Gly  Trp Ile Tyr Asp Met  Glu Asn Glu Ser Asp  Lys Tyr Tyr
    2210                 2215                 2220

Phe Asp  Pro Glu Thr Lys Lys  Ala Tyr Lys Gly Ile  Asn Val Ile
    2225                 2230                 2235
```

```
Asp Asp  Ile Lys Tyr Tyr Phe  Asp Glu Asn Gly Ile  Met Arg Thr
    2240                 2245                 2250

Gly Leu  Ile Thr Phe Glu Asp  Asn His Tyr Tyr Phe  Asn Glu Asp
    2255                 2260                 2265

Gly Ile  Met Gln Tyr Gly Tyr  Leu Asn Ile Glu Asp  Lys Thr Phe
    2270                 2275                 2280

Tyr Phe  Ser Glu Asp Gly Ile  Met Gln Ile Gly Val  Phe Asn Thr
    2285                 2290                 2295

Pro Asp  Gly Phe Lys Tyr Phe  Ala His Gln Asn Thr  Leu Asp Glu
    2300                 2305                 2310

Asn Phe  Glu Gly Glu Ser Ile  Asn Tyr Thr Gly Trp  Leu Asp Leu
    2315                 2320                 2325

Asp Glu  Lys Arg Tyr Tyr Phe  Thr Asp Glu Tyr Ile  Ala Ala Thr
    2330                 2335                 2340

Gly Ser  Val Ile Ile Asp Gly  Glu Glu Tyr Tyr Phe  Asp Pro Asp
    2345                 2350                 2355

Thr Ala  Gln Leu Val Ile Ser  Glu
    2360                 2365


<210> SEQ ID NO 14
<211> LENGTH: 2366
<212> TYPE: PRT
<213> ORGANISM: Clostridium difficile
<220> FEATURE:
<221> NAME/KEY: PEPTIDE
<222> LOCATION: (1)..(2366)

<400> SEQUENCE: 14

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Ala Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220
```

-continued

```
Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Glu Gly Ser Leu Gly
    530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
```

```
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
    690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser Ile
        755                 760                 765

Ile Lys Asp Ile Ser Ser Lys Glu Tyr Ile Ser Phe Asn Pro Lys Glu
    770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
        835                 840                 845

Ser Asp Ser Ile Asn Tyr Ile Lys Asp Glu Phe Lys Leu Ile Glu Ser
    850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
            900                 905                 910

Thr Glu Lys Thr Ile Phe Ser Glu Tyr Ala Asn His Ile Thr Glu Glu
        915                 920                 925

Ile Ser Lys Ile Lys Gly Thr Ile Phe Asp Thr Val Asn Gly Lys Leu
    930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr  Ile Thr Asp Ala Ala  Lys Val Val
        995                 1000                1005

Glu Leu  Val Ser Thr Ala Leu  Asp Glu Thr Ile Asp  Leu Leu Pro
    1010                1015                1020

Thr Leu  Ser Glu Gly Leu Pro  Ile Ile Ala Thr Ile  Ile Asp Gly
    1025                1030                1035

Val Ser  Leu Gly Ala Ala Ile  Lys Glu Leu Ser Glu  Thr Ser Asp
    1040                1045                1050

Pro Leu  Leu Arg Gln Glu Ile  Glu Ala Lys Ile Gly  Ile Met Ala
    1055                1060                1065
```

```
Val Asn  Leu Thr Thr Ala Thr  Thr Ala Ile Ile Thr  Ser Ser Leu
    1070                 1075                 1080

Gly Ile  Ala Ser Gly Phe Ser  Ile Leu Leu Val Pro  Leu Ala Gly
    1085                 1090                 1095

Ile Ser  Ala Gly Ile Pro Ser  Leu Val Asn Asn Glu  Leu Val Leu
    1100                 1105                 1110

Arg Asp  Lys Ala Thr Lys Val  Val Asp Tyr Phe Lys  His Val Ser
    1115                 1120                 1125

Leu Val  Glu Thr Glu Gly Val  Phe Thr Leu Leu Asp  Asp Lys Ile
    1130                 1135                 1140

Met Met  Pro Gln Asp Asp Leu  Val Ile Ser Glu Ile  Asp Phe Asn
    1145                 1150                 1155

Asn Asn  Ser Ile Val Leu Gly  Lys Cys Glu Ile Trp  Arg Met Glu
    1160                 1165                 1170

Gly Gly  Ser Gly His Thr Val  Thr Asp Asp Ile Asp  His Phe Phe
    1175                 1180                 1185

Ser Ala  Pro Ser Ile Thr Tyr  Arg Glu Pro His Leu  Ser Ile Tyr
    1190                 1195                 1200

Asp Val  Leu Glu Val Gln Lys  Glu Glu Leu Asp Leu  Ser Lys Asp
    1205                 1210                 1215

Leu Met  Val Leu Pro Asn Ala  Pro Asn Arg Val Phe  Ala Trp Glu
    1220                 1225                 1230

Thr Gly  Trp Thr Pro Gly Leu  Arg Ser Leu Glu Asn  Asp Gly Thr
    1235                 1240                 1245

Lys Leu  Leu Asp Arg Ile Arg  Asp Asn Tyr Glu Gly  Glu Phe Tyr
    1250                 1255                 1260

Trp Arg  Tyr Phe Ala Phe Ile  Ala Asp Ala Leu Ile  Thr Thr Leu
    1265                 1270                 1275

Lys Pro  Arg Tyr Glu Asp Thr  Asn Ile Arg Ile Asn  Leu Asp Ser
    1280                 1285                 1290

Asn Thr  Arg Ser Phe Ile Val  Pro Ile Ile Thr Thr  Glu Tyr Ile
    1295                 1300                 1305

Arg Glu  Lys Leu Ser Tyr Ser  Phe Tyr Gly Ser Gly  Gly Thr Tyr
    1310                 1315                 1320

Ala Leu  Ser Leu Ser Gln Tyr  Asn Met Gly Ile Asn  Ile Glu Leu
    1325                 1330                 1335

Ser Glu  Ser Asp Val Trp Ile  Ile Asp Val Asp Asn  Val Val Arg
    1340                 1345                 1350

Asp Val  Thr Ile Glu Ser Asp  Lys Ile Lys Lys Gly  Asp Leu Ile
    1355                 1360                 1365

Glu Gly  Ile Leu Ser Thr Leu  Ser Ile Glu Glu Asn  Lys Ile Ile
    1370                 1375                 1380

Leu Asn  Ser His Glu Ile Asn  Phe Ser Gly Glu Val  Asn Gly Ser
    1385                 1390                 1395

Asn Gly  Phe Val Ser Leu Thr  Phe Ser Ile Leu Glu  Gly Ile Asn
    1400                 1405                 1410

Ala Ile  Ile Glu Val Asp Leu  Leu Ser Lys Ser Tyr  Lys Leu Leu
    1415                 1420                 1425

Ile Ser  Gly Glu Leu Lys Ile  Leu Met Leu Asn Ser  Asn His Ile
    1430                 1435                 1440

Gln Gln  Lys Ile Asp Tyr Ile  Gly Phe Asn Ser Glu  Leu Gln Lys
    1445                 1450                 1455

Asn Ile  Pro Tyr Ser Phe Val  Asp Ser Glu Gly Lys  Glu Asn Gly
    1460                 1465                 1470
```

-continued

```
Phe Ile  Asn Gly Ser Thr Lys  Glu Gly Leu Phe Val  Ser Glu Leu
    1475                 1480                 1485

Pro Asp  Val Val Leu Ile Ser  Lys Val Tyr Met Asp  Asp Ser Lys
    1490                 1495                 1500

Pro Ser  Phe Gly Tyr Tyr Ser  Asn Asn Leu Lys Asp  Val Lys Val
    1505                 1510                 1515

Ile Thr  Lys Asp Asn Val Asn  Ile Leu Thr Gly Tyr  Tyr Leu Lys
    1520                 1525                 1530

Asp Asp  Ile Lys Ile Ser Leu  Ser Leu Thr Leu Gln  Asp Glu Lys
    1535                 1540                 1545

Thr Ile  Lys Leu Asn Ser Val  His Leu Asp Glu Ser  Gly Val Ala
    1550                 1555                 1560

Glu Ile  Leu Lys Phe Met Asn  Arg Lys Gly Asn Thr  Asn Thr Ser
    1565                 1570                 1575

Asp Ser  Leu Met Ser Phe Leu  Glu Ser Met Asn Ile  Lys Ser Ile
    1580                 1585                 1590

Phe Val  Asn Phe Leu Gln Ser  Asn Ile Lys Phe Ile  Leu Asp Ala
    1595                 1600                 1605

Asn Phe  Ile Ile Ser Gly Thr  Thr Ser Ile Gly Gln  Phe Glu Phe
    1610                 1615                 1620

Ile Cys  Asp Glu Asn Asp Asn  Ile Gln Pro Tyr Phe  Ile Lys Phe
    1625                 1630                 1635

Asn Thr  Leu Glu Thr Asn Tyr  Thr Leu Tyr Val Gly  Asn Arg Gln
    1640                 1645                 1650

Asn Met  Ile Val Glu Pro Asn  Tyr Asp Leu Asp Asp  Ser Gly Asp
    1655                 1660                 1665

Ile Ser  Ser Thr Val Ile Asn  Phe Ser Gln Lys Tyr  Leu Tyr Gly
    1670                 1675                 1680

Ile Asp  Ser Cys Val Asn Lys  Val Val Ile Ser Pro  Asn Ile Tyr
    1685                 1690                 1695

Thr Asp  Glu Ile Asn Ile Thr  Pro Val Tyr Glu Thr  Asn Asn Thr
    1700                 1705                 1710

Tyr Pro  Glu Val Ile Val Leu  Asp Ala Asn Tyr Ile  Asn Glu Lys
    1715                 1720                 1725

Ile Asn  Val Asn Ile Asn Asp  Leu Ser Ile Arg Tyr  Val Trp Ser
    1730                 1735                 1740

Asn Asp  Gly Asn Asp Phe Ile  Leu Met Ser Thr Ser  Glu Glu Asn
    1745                 1750                 1755

Lys Val  Ser Gln Val Lys Ile  Arg Phe Val Asn Val  Phe Lys Asp
    1760                 1765                 1770

Lys Thr  Leu Ala Asn Lys Leu  Ser Phe Asn Phe Ser  Asp Lys Gln
    1775                 1780                 1785

Asp Val  Pro Val Ser Glu Ile  Ile Leu Ser Phe Thr  Pro Ser Tyr
    1790                 1795                 1800

Tyr Glu  Asp Gly Leu Ile Gly  Tyr Asp Leu Gly Leu  Val Ser Leu
    1805                 1810                 1815

Tyr Asn  Glu Lys Phe Tyr Ile  Asn Asn Phe Gly Met  Met Val Ser
    1820                 1825                 1830

Gly Leu  Ile Tyr Ile Asn Asp  Ser Leu Tyr Tyr Phe  Lys Pro Pro
    1835                 1840                 1845

Val Asn  Asn Leu Ile Thr Gly  Phe Val Thr Val Gly  Asp Asp Lys
    1850                 1855                 1860

Tyr Tyr  Phe Asn Pro Ile Asn  Gly Gly Ala Ala Ser  Ile Gly Glu
```

-continued

```
    1865                1870                1875

Thr Ile  Ile Asp Asp Lys Asn  Tyr Tyr Phe Asn Gln  Ser Gly Val
    1880                1885                1890

Leu Gln  Thr Gly Val Phe Ser  Thr Glu Asp Gly Phe  Lys Tyr Phe
    1895                1900                1905

Ala Pro  Ala Asn Thr Leu Asp  Glu Asn Leu Glu Gly  Glu Ala Ile
    1910                1915                1920

Asp Phe  Thr Gly Lys Leu Ile  Ile Asp Glu Asn Ile  Tyr Tyr Phe
    1925                1930                1935

Asp Asp  Asn Tyr Arg Gly Ala  Val Glu Trp Lys Glu  Leu Asp Gly
    1940                1945                1950

Glu Met  His Tyr Phe Ser Pro  Glu Thr Gly Lys Ala  Phe Lys Gly
    1955                1960                1965

Leu Asn  Gln Ile Gly Asp Tyr  Lys Tyr Tyr Phe Asn  Ser Asp Gly
    1970                1975                1980

Val Met  Gln Lys Gly Phe Val  Ser Ile Asn Asp Asn  Lys His Tyr
    1985                1990                1995

Phe Asp  Asp Ser Gly Val Met  Lys Val Gly Tyr Thr  Glu Ile Asp
    2000                2005                2010

Gly Lys  His Phe Tyr Phe Ala  Glu Asn Gly Glu Met  Gln Ile Gly
    2015                2020                2025

Val Phe  Asn Thr Glu Asp Gly  Phe Lys Tyr Phe Ala  His His Asn
    2030                2035                2040

Glu Asp  Leu Gly Asn Glu Glu  Gly Glu Glu Ile Ser  Tyr Ser Gly
    2045                2050                2055

Ile Leu  Asn Phe Asn Asn Lys  Ile Tyr Tyr Phe Asp  Asp Ser Phe
    2060                2065                2070

Thr Ala  Val Val Gly Trp Lys  Asp Leu Glu Asp Gly  Ser Lys Tyr
    2075                2080                2085

Tyr Phe  Asp Glu Asp Thr Ala  Glu Ala Tyr Ile Gly  Leu Ser Leu
    2090                2095                2100

Ile Asn  Asp Gly Gln Tyr Tyr  Phe Asn Asp Asp Gly  Ile Met Gln
    2105                2110                2115

Val Gly  Phe Val Thr Ile Asn  Asp Lys Val Phe Tyr  Phe Ser Asp
    2120                2125                2130

Ser Gly  Ile Ile Glu Ser Gly  Val Gln Asn Ile Asp  Asp Asn Tyr
    2135                2140                2145

Phe Tyr  Ile Asp Asp Asn Gly  Ile Val Gln Ile Gly  Val Phe Asp
    2150                2155                2160

Thr Ser  Asp Gly Tyr Lys Tyr  Phe Ala Pro Ala Asn  Thr Val Asn
    2165                2170                2175

Asp Asn  Ile Tyr Gly Gln Ala  Val Glu Tyr Ser Gly  Leu Val Arg
    2180                2185                2190

Val Gly  Glu Asp Val Tyr Tyr  Phe Gly Glu Thr Tyr  Thr Ile Glu
    2195                2200                2205

Thr Gly  Trp Ile Tyr Asp Met  Glu Asn Glu Ser Asp  Lys Tyr Tyr
    2210                2215                2220

Phe Asn  Pro Glu Thr Lys Lys  Ala Cys Lys Gly Ile  Asn Leu Ile
    2225                2230                2235

Asp Asp  Ile Lys Tyr Tyr Phe  Asp Glu Lys Gly Ile  Met Arg Thr
    2240                2245                2250

Gly Leu  Ile Ser Phe Glu Asn  Asn Asn Tyr Tyr Phe  Asn Glu Asn
    2255                2260                2265
```

```
Gly Glu  Met Gln Phe Gly Tyr  Ile Asn Ile Glu Asp  Lys Met Phe
    2270                2275                2280

Tyr Phe  Gly Glu Asp Gly Val  Met Gln Ile Gly Val  Phe Asn Thr
    2285                2290                2295

Pro Asp  Gly Phe Lys Tyr Phe  Ala His Gln Asn Thr  Leu Asp Glu
    2300                2305                2310

Asn Phe  Glu Gly Glu Ser Ile  Asn Tyr Thr Gly Trp  Leu Asp Leu
    2315                2320                2325

Asp Glu  Lys Arg Tyr Tyr Phe  Thr Asp Glu Tyr Ile  Ala Ala Thr
    2330                2335                2340

Gly Ser  Val Ile Ile Asp Gly  Glu Glu Tyr Tyr Phe  Asp Pro Asp
    2345                2350                2355

Thr Ala  Gln Leu Val Ile Ser  Glu
    2360                2365


<210> SEQ ID NO 15
<211> LENGTH: 2366
<212> TYPE: PRT
<213> ORGANISM: Clostridium difficile
<220> FEATURE:
<221> NAME/KEY: PEPTIDE
<222> LOCATION: (1)..(2366)

<400> SEQUENCE: 15

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255
```

-continued

```
Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Gly Val Gly
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Glu Gly Ser Leu Gly
    530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
        675                 680                 685
```

```
Lys Ser Ile Glu Ile Asn Leu Leu Gly Cys Asn Met Phe Ser Tyr Ser
    690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser Ile
        755                 760                 765

Ile Lys Asp Ile Ser Ser Lys Glu Tyr Ile Ser Phe Asn Pro Lys Glu
    770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
        835                 840                 845

Ser Asp Ser Ile Asn Tyr Ile Lys Asp Glu Phe Lys Leu Ile Glu Ser
    850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
            900                 905                 910

Thr Glu Lys Thr Ile Phe Ser Glu Tyr Ala Asn His Ile Thr Glu Glu
        915                 920                 925

Ile Ser Lys Ile Lys Gly Thr Ile Phe Asp Thr Val Asn Gly Lys Leu
    930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr  Ile Thr Asp Ala Ala  Lys Val Val
        995                 1000                1005

Glu Leu  Val Ser Thr Ala Leu  Asp Glu Thr Ile Asp  Leu Leu Pro
    1010                 1015                 1020

Thr Leu  Ser Glu Gly Leu Pro  Ile Ile Ala Thr Ile  Ile Asp Gly
    1025                 1030                 1035

Val Ser  Leu Gly Ala Ala Ile  Lys Glu Leu Ser Glu  Thr Ser Asp
    1040                 1045                 1050

Pro Leu  Leu Arg Gln Glu Ile  Glu Ala Lys Ile Gly  Ile Met Ala
    1055                 1060                 1065

Val Asn  Leu Thr Thr Ala Thr  Thr Ala Ile Ile Thr  Ser Ser Leu
    1070                 1075                 1080

Gly Ile  Ala Ser Gly Phe Ser  Ile Leu Leu Val Pro  Leu Ala Gly
    1085                 1090                 1095

Ile Ser  Ala Gly Ile Pro Ser  Leu Val Asn Asn Glu  Leu Val Leu
```

-continued

```
    1100                1105                1110

Arg Asp  Lys Ala Thr Lys Val  Val Asp Tyr Phe Lys  His Val Ser
    1115                1120                1125

Leu Val  Glu Thr Glu Gly Val  Phe Thr Leu Leu Asp  Asp Lys Ile
    1130                1135                1140

Met Met  Pro Gln Asp Asp Leu  Val Ile Ser Glu Ile  Asp Phe Asn
    1145                1150                1155

Asn Asn  Ser Ile Val Leu Gly  Lys Cys Glu Ile Trp  Arg Met Glu
    1160                1165                1170

Gly Gly  Ser Gly His Thr Val  Thr Asp Asp Ile Asp  His Phe Phe
    1175                1180                1185

Ser Ala  Pro Ser Ile Thr Tyr  Arg Glu Pro His Leu  Ser Ile Tyr
    1190                1195                1200

Asp Val  Leu Glu Val Gln Lys  Glu Glu Leu Asp Leu  Ser Lys Asp
    1205                1210                1215

Leu Met  Val Leu Pro Asn Ala  Pro Asn Arg Val Phe  Ala Trp Glu
    1220                1225                1230

Thr Gly  Trp Thr Pro Gly Leu  Arg Ser Leu Glu Asn  Asp Gly Thr
    1235                1240                1245

Lys Leu  Leu Asp Arg Ile Arg  Asp Asn Tyr Glu Gly  Glu Phe Tyr
    1250                1255                1260

Trp Arg  Tyr Phe Ala Phe Ile  Ala Asp Ala Leu Ile  Thr Thr Leu
    1265                1270                1275

Lys Pro  Arg Tyr Glu Asp Thr  Asn Ile Arg Ile Asn  Leu Asp Ser
    1280                1285                1290

Asn Thr  Arg Ser Phe Ile Val  Pro Ile Ile Thr Thr  Glu Tyr Ile
    1295                1300                1305

Arg Glu  Lys Leu Ser Tyr Ser  Phe Tyr Gly Ser Gly  Gly Thr Tyr
    1310                1315                1320

Ala Leu  Ser Leu Ser Gln Tyr  Asn Met Gly Ile Asn  Ile Glu Leu
    1325                1330                1335

Ser Glu  Ser Asp Val Trp Ile  Ile Asp Val Asp Asn  Val Val Arg
    1340                1345                1350

Asp Val  Thr Ile Glu Ser Asp  Lys Ile Lys Lys Gly  Asp Leu Ile
    1355                1360                1365

Glu Gly  Ile Leu Ser Thr Leu  Ser Ile Glu Glu Asn  Lys Ile Ile
    1370                1375                1380

Leu Asn  Ser His Glu Ile Asn  Phe Ser Gly Glu Val  Asn Gly Ser
    1385                1390                1395

Asn Gly  Phe Val Ser Leu Thr  Phe Ser Ile Leu Glu  Gly Ile Asn
    1400                1405                1410

Ala Ile  Ile Glu Val Asp Leu  Leu Ser Lys Ser Tyr  Lys Leu Leu
    1415                1420                1425

Ile Ser  Gly Glu Leu Lys Ile  Leu Met Leu Asn Ser  Asn His Ile
    1430                1435                1440

Gln Gln  Lys Ile Asp Tyr Ile  Gly Phe Asn Ser Glu  Leu Gln Lys
    1445                1450                1455

Asn Ile  Pro Tyr Ser Phe Val  Asp Ser Glu Gly Lys  Glu Asn Gly
    1460                1465                1470

Phe Ile  Asn Gly Ser Thr Lys  Glu Gly Leu Phe Val  Ser Glu Leu
    1475                1480                1485

Pro Asp  Val Val Leu Ile Ser  Lys Val Tyr Met Asp  Asp Ser Lys
    1490                1495                1500
```

```
Pro Ser  Phe Gly Tyr Tyr Ser  Asn Asn Leu Lys Asp  Val Lys Val
    1505                 1510                 1515

Ile Thr  Lys Asp Asn Val Asn  Ile Leu Thr Gly Tyr  Tyr Leu Lys
    1520                 1525                 1530

Asp Asp  Ile Lys Ile Ser Leu  Ser Leu Thr Leu Gln  Asp Glu Lys
    1535                 1540                 1545

Thr Ile  Lys Leu Asn Ser Val  His Leu Asp Glu Ser  Gly Val Ala
    1550                 1555                 1560

Glu Ile  Leu Lys Phe Met Asn  Arg Lys Gly Asn Thr  Asn Thr Ser
    1565                 1570                 1575

Asp Ser  Leu Met Ser Phe Leu  Glu Ser Met Asn Ile  Lys Ser Ile
    1580                 1585                 1590

Phe Val  Asn Phe Leu Gln Ser  Asn Ile Lys Phe Ile  Leu Asp Ala
    1595                 1600                 1605

Asn Phe  Ile Ile Ser Gly Thr  Thr Ser Ile Gly Gln  Phe Glu Phe
    1610                 1615                 1620

Ile Cys  Asp Glu Asn Asp Asn  Ile Gln Pro Tyr Phe  Ile Lys Phe
    1625                 1630                 1635

Asn Thr  Leu Glu Thr Asn Tyr  Thr Leu Tyr Val Gly  Asn Arg Gln
    1640                 1645                 1650

Asn Met  Ile Val Glu Pro Asn  Tyr Asp Leu Asp Asp  Ser Gly Asp
    1655                 1660                 1665

Ile Ser  Ser Thr Val Ile Asn  Phe Ser Gln Lys Tyr  Leu Tyr Gly
    1670                 1675                 1680

Ile Asp  Ser Cys Val Asn Lys  Val Val Ile Ser Pro  Asn Ile Tyr
    1685                 1690                 1695

Thr Asp  Glu Ile Asn Ile Thr  Pro Val Tyr Glu Thr  Asn Asn Thr
    1700                 1705                 1710

Tyr Pro  Glu Val Ile Val Leu  Asp Ala Asn Tyr Ile  Asn Glu Lys
    1715                 1720                 1725

Ile Asn  Val Asn Ile Asn Asp  Leu Ser Ile Arg Tyr  Val Trp Ser
    1730                 1735                 1740

Asn Asp  Gly Asn Asp Phe Ile  Leu Met Ser Thr Ser  Glu Glu Asn
    1745                 1750                 1755

Lys Val  Ser Gln Val Lys Ile  Arg Phe Val Asn Val  Phe Lys Asp
    1760                 1765                 1770

Lys Thr  Leu Ala Asn Lys Leu  Ser Phe Asn Phe Ser  Asp Lys Gln
    1775                 1780                 1785

Asp Val  Pro Val Ser Glu Ile  Ile Leu Ser Phe Thr  Pro Ser Tyr
    1790                 1795                 1800

Tyr Glu  Asp Gly Leu Ile Gly  Tyr Asp Leu Gly Leu  Val Ser Leu
    1805                 1810                 1815

Tyr Asn  Glu Lys Phe Tyr Ile  Asn Asn Phe Gly Met  Met Val Ser
    1820                 1825                 1830

Gly Leu  Ile Tyr Ile Asn Asp  Ser Leu Tyr Tyr Phe  Lys Pro Pro
    1835                 1840                 1845

Val Asn  Asn Leu Ile Thr Gly  Phe Val Thr Val Gly  Asp Asp Lys
    1850                 1855                 1860

Tyr Tyr  Phe Asn Pro Ile Asn  Gly Gly Ala Ala Ser  Ile Gly Glu
    1865                 1870                 1875

Thr Ile  Ile Asp Asp Lys Asn  Tyr Tyr Phe Asn Gln  Ser Gly Val
    1880                 1885                 1890

Leu Gln  Thr Gly Val Phe Ser  Thr Glu Asp Gly Phe  Lys Tyr Phe
    1895                 1900                 1905
```

```
Ala Pro  Ala Asn Thr Leu Asp  Glu Asn Leu Glu Gly  Glu Ala Ile
    1910                 1915                 1920

Asp Phe  Thr Gly Lys Leu Ile  Ile Asp Glu Asn Ile  Tyr Tyr Phe
    1925                 1930                 1935

Asp Asp  Asn Tyr Arg Gly Ala  Val Glu Trp Lys Glu  Leu Asp Gly
    1940                 1945                 1950

Glu Met  His Tyr Phe Ser Pro  Glu Thr Gly Lys Ala  Phe Lys Gly
    1955                 1960                 1965

Leu Asn  Gln Ile Gly Asp Tyr  Lys Tyr Tyr Phe Asn  Ser Asp Gly
    1970                 1975                 1980

Val Met  Gln Lys Gly Phe Val  Ser Ile Asn Asp Asn  Lys His Tyr
    1985                 1990                 1995

Phe Asp  Asp Ser Gly Val Met  Lys Val Gly Tyr Thr  Glu Ile Asp
    2000                 2005                 2010

Gly Lys  His Phe Tyr Phe Ala  Glu Asn Gly Glu Met  Gln Ile Gly
    2015                 2020                 2025

Val Phe  Asn Thr Glu Asp Gly  Phe Lys Tyr Phe Ala  His His Asn
    2030                 2035                 2040

Glu Asp  Leu Gly Asn Glu Glu  Gly Glu Glu Ile Ser  Tyr Ser Gly
    2045                 2050                 2055

Ile Leu  Asn Phe Asn Asn Lys  Ile Tyr Tyr Phe Asp  Asp Ser Phe
    2060                 2065                 2070

Thr Ala  Val Val Gly Trp Lys  Asp Leu Glu Asp Gly  Ser Lys Tyr
    2075                 2080                 2085

Tyr Phe  Asp Glu Asp Thr Ala  Glu Ala Tyr Ile Gly  Leu Ser Leu
    2090                 2095                 2100

Ile Asn  Asp Gly Gln Tyr Tyr  Phe Asn Asp Asp Gly  Ile Met Gln
    2105                 2110                 2115

Val Gly  Phe Val Thr Ile Asn  Asp Lys Val Phe Tyr  Phe Ser Asp
    2120                 2125                 2130

Ser Gly  Ile Ile Glu Ser Gly  Val Gln Asn Ile Asp  Asp Asn Tyr
    2135                 2140                 2145

Phe Tyr  Ile Asp Asp Asn Gly  Ile Val Gln Ile Gly  Val Phe Asp
    2150                 2155                 2160

Thr Ser  Asp Gly Tyr Lys Tyr  Phe Ala Pro Ala Asn  Thr Val Asn
    2165                 2170                 2175

Asp Asn  Ile Tyr Gly Gln Ala  Val Glu Tyr Ser Gly  Leu Val Arg
    2180                 2185                 2190

Val Gly  Glu Asp Val Tyr Tyr  Phe Gly Glu Thr Tyr  Thr Ile Glu
    2195                 2200                 2205

Thr Gly  Trp Ile Tyr Asp Met  Glu Asn Glu Ser Asp  Lys Tyr Tyr
    2210                 2215                 2220

Phe Asn  Pro Glu Thr Lys Lys  Ala Cys Lys Gly Ile  Asn Leu Ile
    2225                 2230                 2235

Asp Asp  Ile Lys Tyr Tyr Phe  Asp Glu Lys Gly Ile  Met Arg Thr
    2240                 2245                 2250

Gly Leu  Ile Ser Phe Glu Asn  Asn Asn Tyr Tyr Phe  Asn Glu Asn
    2255                 2260                 2265

Gly Glu  Met Gln Phe Gly Tyr  Ile Asn Ile Glu Asp  Lys Met Phe
    2270                 2275                 2280

Tyr Phe  Gly Glu Asp Gly Val  Met Gln Ile Gly Val  Phe Asn Thr
    2285                 2290                 2295

Pro Asp  Gly Phe Lys Tyr Phe  Ala His Gln Asn Thr  Leu Asp Glu
```

```
    2300                2305                2310

Asn Phe  Glu Gly Glu Ser Ile  Asn Tyr Thr Gly Trp  Leu Asp Leu
    2315                2320                2325

Asp Glu  Lys Arg Tyr Tyr Phe  Thr Asp Glu Tyr Ile  Ala Ala Thr
    2330                2335                2340

Gly Ser  Val Ile Ile Asp Gly  Glu Glu Tyr Tyr Phe  Asp Pro Asp
    2345                2350                2355

Thr Ala  Gln Leu Val Ile Ser  Glu
    2360                2365


<210> SEQ ID NO 16
<211> LENGTH: 721
<212> TYPE: PRT
<213> ORGANISM: Clostridium difficile
<220> FEATURE:
<221> NAME/KEY: PEPTIDE
<222> LOCATION: (1)..(721)

<400> SEQUENCE: 16

Met Leu Tyr Val Gly Asn Arg Gln Asn Met Ile Val Glu Pro Asn Tyr
1               5                   10                  15

Asp Leu Asp Asp Ser Gly Asp Ile Ser Ser Thr Val Ile Asn Phe Ser
            20                  25                  30

Gln Lys Tyr Leu Tyr Gly Ile Asp Ser Cys Val Asn Lys Val Ile Ile
        35                  40                  45

Ser Pro Asn Ile Tyr Thr Asp Glu Ile Asn Ile Thr Pro Ile Tyr Glu
    50                  55                  60

Ala Asn Asn Thr Tyr Pro Glu Val Ile Val Leu Asp Thr Asn Tyr Ile
65                  70                  75                  80

Ser Glu Lys Ile Asn Ile Asn Ile Asn Asp Leu Ser Ile Arg Tyr Val
                85                  90                  95

Trp Ser Asn Asp Gly Ser Asp Phe Ile Leu Met Ser Thr Asp Glu Glu
            100                 105                 110

Asn Lys Val Ser Gln Val Lys Ile Arg Phe Thr Asn Val Phe Lys Gly
        115                 120                 125

Asn Thr Ile Ser Asp Lys Ile Ser Phe Asn Phe Ser Asp Lys Gln Asp
    130                 135                 140

Val Ser Ile Asn Lys Val Ile Ser Thr Phe Thr Pro Ser Tyr Tyr Val
145                 150                 155                 160

Glu Gly Leu Leu Asn Tyr Asp Leu Gly Leu Ile Ser Leu Tyr Asn Glu
                165                 170                 175

Lys Phe Tyr Ile Asn Asn Phe Gly Met Met Val Ser Gly Leu Val Tyr
            180                 185                 190

Ile Asn Asp Ser Leu Tyr Tyr Phe Lys Pro Pro Ile Lys Asn Leu Ile
        195                 200                 205

Thr Gly Phe Thr Thr Ile Gly Asp Asp Lys Tyr Tyr Phe Asn Pro Asp
    210                 215                 220

Asn Gly Gly Ala Ala Ser Val Gly Glu Thr Ile Ile Asp Gly Lys Asn
225                 230                 235                 240

Tyr Tyr Phe Ser Gln Asn Gly Val Leu Gln Thr Gly Val Phe Ser Thr
                245                 250                 255

Glu Asp Gly Phe Lys Tyr Phe Ala Pro Ala Asp Thr Leu Asp Glu Asn
            260                 265                 270

Leu Glu Gly Glu Ala Ile Asp Phe Thr Gly Lys Leu Thr Ile Asp Glu
        275                 280                 285

Asn Val Tyr Tyr Phe Gly Asp Asn Tyr Arg Ala Ala Ile Glu Trp Gln
```

-continued

```
    290                 295                 300

Thr Leu Asp Asp Glu Val Tyr Tyr Phe Ser Thr Asp Thr Gly Arg Ala
305                 310                 315                 320

Phe Lys Gly Leu Asn Gln Ile Gly Asp Asp Lys Phe Tyr Phe Asn Ser
                325                 330                 335

Asp Gly Ile Met Gln Lys Gly Phe Val Asn Ile Asn Asp Lys Thr Phe
            340                 345                 350

Tyr Phe Asp Asp Ser Gly Val Met Lys Ser Gly Tyr Thr Glu Ile Asp
        355                 360                 365

Gly Lys Tyr Phe Tyr Phe Ala Glu Asn Gly Glu Met Gln Ile Gly Val
    370                 375                 380

Phe Asn Thr Ala Asp Gly Phe Lys Tyr Phe Ala His His Asp Glu Asp
385                 390                 395                 400

Leu Gly Asn Glu Glu Gly Glu Ala Leu Ser Tyr Ser Gly Ile Leu Asn
                405                 410                 415

Phe Asn Asn Lys Ile Tyr Tyr Phe Asp Asp Ser Phe Thr Ala Val Val
            420                 425                 430

Gly Trp Lys Asp Leu Glu Asp Gly Ser Lys Tyr Tyr Phe Asp Glu Asp
        435                 440                 445

Thr Ala Glu Ala Tyr Ile Gly Ile Ser Ile Ile Asn Asp Gly Lys Tyr
    450                 455                 460

Tyr Phe Asn Asp Ser Gly Ile Met Gln Ile Gly Phe Val Thr Ile Asn
465                 470                 475                 480

Asn Glu Val Phe Tyr Phe Ser Asp Ser Gly Ile Val Glu Ser Gly Met
                485                 490                 495

Gln Asn Ile Asp Asp Asn Tyr Phe Tyr Ile Asp Glu Asn Gly Leu Val
            500                 505                 510

Gln Ile Gly Val Phe Asp Thr Ser Asp Gly Tyr Lys Tyr Phe Ala Pro
        515                 520                 525

Ala Asn Thr Val Asn Asp Asn Ile Tyr Gly Gln Ala Val Glu Tyr Ser
    530                 535                 540

Gly Leu Val Arg Val Gly Glu Asp Val Tyr Tyr Phe Gly Glu Thr Tyr
545                 550                 555                 560

Thr Ile Glu Thr Gly Trp Ile Tyr Asp Met Glu Asn Glu Ser Asp Lys
                565                 570                 575

Tyr Tyr Phe Asp Pro Glu Thr Lys Lys Ala Tyr Lys Gly Ile Asn Val
            580                 585                 590

Ile Asp Asp Ile Lys Tyr Tyr Phe Asp Glu Asn Gly Ile Met Arg Thr
        595                 600                 605

Gly Leu Ile Thr Phe Glu Asp Asn His Tyr Tyr Phe Asn Glu Asp Gly
    610                 615                 620

Ile Met Gln Tyr Gly Tyr Leu Asn Ile Glu Asp Lys Thr Phe Tyr Phe
625                 630                 635                 640

Ser Glu Asp Gly Ile Met Gln Ile Gly Val Phe Asn Thr Pro Asp Gly
                645                 650                 655

Phe Lys Tyr Phe Ala His Gln Asn Thr Leu Asp Glu Asn Phe Glu Gly
            660                 665                 670

Glu Ser Ile Asn Tyr Thr Gly Trp Leu Asp Leu Asp Glu Lys Arg Tyr
        675                 680                 685

Tyr Phe Thr Asp Glu Tyr Ile Ala Ala Thr Gly Ser Val Ile Ile Asp
    690                 695                 700

Gly Glu Glu Tyr Tyr Phe Asp Pro Asp Thr Ala Gln Leu Val Ile Ser
705                 710                 715                 720
```

Glu

<210> SEQ ID NO 17
<211> LENGTH: 721
<212> TYPE: PRT
<213> ORGANISM: Clostridium difficile
<220> FEATURE:
<221> NAME/KEY: PEPTIDE
<222> LOCATION: (1)..(721)

<400> SEQUENCE: 17

```
Met Leu Tyr Val Gly Asn Arg Gln Asn Met Ile Val Glu Pro Asn Tyr
1               5                   10                  15

Asp Leu Asp Asp Ser Gly Asp Ile Ser Ser Thr Val Ile Asn Phe Ser
            20                  25                  30

Gln Lys Tyr Leu Tyr Gly Ile Asp Ser Cys Val Asn Lys Val Val Ile
        35                  40                  45

Ser Pro Asn Ile Tyr Thr Asp Glu Ile Asn Ile Thr Pro Val Tyr Glu
    50                  55                  60

Thr Asn Asn Thr Tyr Pro Glu Val Ile Val Leu Asp Ala Asn Tyr Ile
65                  70                  75                  80

Asn Glu Lys Ile Asn Val Asn Ile Asn Asp Leu Ser Ile Arg Tyr Val
                85                  90                  95

Trp Ser Asn Asp Gly Asn Asp Phe Ile Leu Met Ser Thr Ser Glu Glu
            100                 105                 110

Asn Lys Val Ser Gln Val Lys Ile Arg Phe Val Asn Val Phe Lys Asp
        115                 120                 125

Lys Thr Leu Ala Asn Lys Leu Ser Phe Asn Phe Ser Asp Lys Gln Asp
    130                 135                 140

Val Pro Val Ser Glu Ile Ile Leu Ser Phe Thr Pro Ser Tyr Tyr Glu
145                 150                 155                 160

Asp Gly Leu Ile Gly Tyr Asp Leu Gly Leu Val Ser Leu Tyr Asn Glu
                165                 170                 175

Lys Phe Tyr Ile Asn Asn Phe Gly Met Met Val Ser Gly Leu Ile Tyr
            180                 185                 190

Ile Asn Asp Ser Leu Tyr Tyr Phe Lys Pro Pro Val Asn Asn Leu Ile
        195                 200                 205

Thr Gly Phe Val Thr Val Gly Asp Asp Lys Tyr Tyr Phe Asn Pro Ile
    210                 215                 220

Asn Gly Gly Ala Ala Ser Ile Gly Glu Thr Ile Ile Asp Asp Lys Asn
225                 230                 235                 240

Tyr Tyr Phe Asn Gln Ser Gly Val Leu Gln Thr Gly Val Phe Ser Thr
                245                 250                 255

Glu Asp Gly Phe Lys Tyr Phe Ala Pro Ala Asn Thr Leu Asp Glu Asn
            260                 265                 270

Leu Glu Gly Glu Ala Ile Asp Phe Thr Gly Lys Leu Ile Ile Asp Glu
        275                 280                 285

Asn Ile Tyr Tyr Phe Asp Asp Asn Tyr Arg Gly Ala Val Glu Trp Lys
    290                 295                 300

Glu Leu Asp Gly Glu Met His Tyr Phe Ser Pro Glu Thr Gly Lys Ala
305                 310                 315                 320

Phe Lys Gly Leu Asn Gln Ile Gly Asp Tyr Lys Tyr Tyr Phe Asn Ser
                325                 330                 335

Asp Gly Val Met Gln Lys Gly Phe Val Ser Ile Asn Asp Asn Lys His
            340                 345                 350
```

-continued

```
Tyr Phe Asp Asp Ser Gly Val Met Lys Val Gly Tyr Thr Glu Ile Asp
        355                 360                 365

Gly Lys His Phe Tyr Phe Ala Glu Asn Gly Glu Met Gln Ile Gly Val
    370                 375                 380

Phe Asn Thr Glu Asp Gly Phe Lys Tyr Phe Ala His His Asn Glu Asp
385                 390                 395                 400

Leu Gly Asn Glu Glu Gly Glu Glu Ile Ser Tyr Ser Gly Ile Leu Asn
                405                 410                 415

Phe Asn Asn Lys Ile Tyr Tyr Phe Asp Asp Ser Phe Thr Ala Val Val
            420                 425                 430

Gly Trp Lys Asp Leu Glu Asp Gly Ser Lys Tyr Tyr Phe Asp Glu Asp
        435                 440                 445

Thr Ala Glu Ala Tyr Ile Gly Leu Ser Leu Ile Asn Asp Gly Gln Tyr
    450                 455                 460

Tyr Phe Asn Asp Asp Gly Ile Met Gln Val Gly Phe Val Thr Ile Asn
465                 470                 475                 480

Asp Lys Val Phe Tyr Phe Ser Asp Ser Gly Ile Ile Glu Ser Gly Val
                485                 490                 495

Gln Asn Ile Asp Asp Asn Tyr Phe Tyr Ile Asp Asp Asn Gly Ile Val
            500                 505                 510

Gln Ile Gly Val Phe Asp Thr Ser Asp Gly Tyr Lys Tyr Phe Ala Pro
        515                 520                 525

Ala Asn Thr Val Asn Asp Asn Ile Tyr Gly Gln Ala Val Glu Tyr Ser
    530                 535                 540

Gly Leu Val Arg Val Gly Glu Asp Val Tyr Tyr Phe Gly Glu Thr Tyr
545                 550                 555                 560

Thr Ile Glu Thr Gly Trp Ile Tyr Asp Met Glu Asn Glu Ser Asp Lys
                565                 570                 575

Tyr Tyr Phe Asn Pro Glu Thr Lys Lys Ala Cys Lys Gly Ile Asn Leu
            580                 585                 590

Ile Asp Asp Ile Lys Tyr Tyr Phe Asp Glu Lys Gly Ile Met Arg Thr
        595                 600                 605

Gly Leu Ile Ser Phe Glu Asn Asn Asn Tyr Tyr Phe Asn Glu Asn Gly
    610                 615                 620

Glu Met Gln Phe Gly Tyr Ile Asn Ile Glu Asp Lys Met Phe Tyr Phe
625                 630                 635                 640

Gly Glu Asp Gly Val Met Gln Ile Gly Val Phe Asn Thr Pro Asp Gly
                645                 650                 655

Phe Lys Tyr Phe Ala His Gln Asn Thr Leu Asp Glu Asn Phe Glu Gly
            660                 665                 670

Glu Ser Ile Asn Tyr Thr Gly Trp Leu Asp Leu Asp Glu Lys Arg Tyr
        675                 680                 685

Tyr Phe Thr Asp Glu Tyr Ile Ala Ala Thr Gly Ser Val Ile Ile Asp
    690                 695                 700

Gly Glu Glu Tyr Tyr Phe Asp Pro Asp Thr Ala Gln Leu Val Ile Ser
705                 710                 715                 720

Glu
```